US009908843B2

United States Patent
Selwood

(10) Patent No.: US 9,908,843 B2
(45) Date of Patent: Mar. 6, 2018

(54) BENZAMIDE DERIVATIVES USEFUL IN THE TREATMENT OF MUSCULAR DISORDERS AND PAIN AND FOR CONTROLLING SPASTICITY AND TREMORS

(71) Applicant: Canbex Therapeutics Limited, London, Greater London (GB)

(72) Inventor: David Selwood, Hertfordshire (GB)

(73) Assignee: CANBEX THERAPEUTICS LIMITED, London, Greater London (GB)

( * ) Notice: Subject to any disclaimer, the term of this patent is extended or adjusted under 35 U.S.C. 154(b) by 0 days.

(21) Appl. No.: 15/101,582

(22) PCT Filed: Dec. 5, 2014

(86) PCT No.: PCT/GB2014/053626
§ 371 (c)(1),
(2) Date: Jun. 3, 2016

(87) PCT Pub. No.: WO2015/082938
PCT Pub. Date: Jun. 11, 2015

(65) Prior Publication Data
US 2016/0304441 A1    Oct. 20, 2016

(30) Foreign Application Priority Data
Dec. 6, 2013  (GB) .................................. 1321601.5

(51) Int. Cl.
*C07C 233/83*  (2006.01)
*C07C 231/12*  (2006.01)
(Continued)

(52) U.S. Cl.
CPC .......... *C07C 233/83* (2013.01); *C07C 231/12* (2013.01); *C07C 233/87* (2013.01);
(Continued)

(58) Field of Classification Search
CPC ... C07C 231/12; C07C 233/83; C07C 233/87; C07C 253/30; C07C 255/41;
(Continued)

(56) References Cited

U.S. PATENT DOCUMENTS

2004/0138244 A1   7/2004  Dalton et al.
2011/0224244 A1   9/2011  Polisetti et al.

FOREIGN PATENT DOCUMENTS

WO   2005080316 A2   9/2005
WO   2010116116 A1  10/2010

OTHER PUBLICATIONS

Wolff (Medicinal Chemistry) summarizes the state of the prodrug art. Wolff, Manfred E. "Burger's Medicinal Chemistry, 5ed, Part I", John Wiley & Sons, 1995, pp. 975-977.*

(Continued)

*Primary Examiner* — Savitha Rao
(74) *Attorney, Agent, or Firm* — Brian C. Trinque; Lathrop Gage LLP

(57) ABSTRACT

The present invention relates to a compound of formula I, or a pharmaceutically acceptable salt thereof: (I) wherein: n is 0 or 1; R1 is selected from H, alkyl and aralkyl, wherein said alkyl and aralkyl groups may be optionally substituted by one or more OH groups; X is a group selected from —C≡C—$(CH_2)_p$—; —C($R^5$)=C($R^6$)—$(CH_2)_q$—; and —C($R^5$)($R^6$)C($R^7$)($R^8$)—$(CH^2)r$-; where each of $R^5$, $R^6$, $R^7$ and $R^8$ is independently H or alkyl, and each of p, q and r is independently 1, 2, 3, 4 or 5; Y is a group selected from: CN; $COOR^2$; $CONR^3R^4$; $SO_2NR^9R^{10}$; $NR^{12}COR^{13}$; $NR^{14}SO_2R^{15}$; and a heterocyclic group selected from oxadiazolyl, thiazolyl, iso-thiazolyl, oxazolyl, iso-oxazolyl, pyrazolyl and imidazolyl; where each of $R^2$, $R^3$ and $R^4$ is independently H or alkyl; or $R^3$ and $R^4$ are linked, together (Continued)

with the nitrogen to which they are attached, to form a 5 or 6-membered heterocycloalkyl or heterocycloalkenyl group, said heterocycloalkyl or heterocycloalkenyl group optionally containing one or more further groups selected from O, N, CO and S, and where each of $R^9$, $R^{10}$, $R^{11}$, $R^{12}$, $R^{13}$, $R^{14}$ and $R^{15}$ is independently H or alkyl. Further aspects of the invention relate to the use of such compounds in the preparation of a medicament for the treatment of a muscular disorder, pain, or for controlling spasticity or tremors, for example, spasticity in MS.

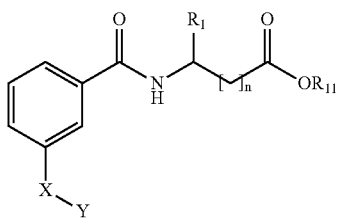

I

19 Claims, 3 Drawing Sheets

(51) Int. Cl.
| | |
|---|---|
| C07C 303/40 | (2006.01) |
| C07C 311/46 | (2006.01) |
| C07D 207/06 | (2006.01) |
| C07C 311/06 | (2006.01) |
| C07C 311/13 | (2006.01) |
| C07C 233/87 | (2006.01) |
| C07C 255/41 | (2006.01) |
| C07D 213/64 | (2006.01) |
| C07D 295/10 | (2006.01) |
| C07C 253/30 | (2006.01) |
| C07D 211/16 | (2006.01) |
| C07D 277/30 | (2006.01) |

(52) U.S. Cl.
CPC .......... *C07C 253/30* (2013.01); *C07C 255/41* (2013.01); *C07C 303/40* (2013.01); *C07C 311/06* (2013.01); *C07C 311/13* (2013.01); *C07C 311/46* (2013.01); *C07D 207/06* (2013.01); *C07D 211/16* (2013.01); *C07D 213/64* (2013.01); *C07D 277/30* (2013.01); *C07D 295/10* (2013.01)

(58) Field of Classification Search
CPC ... C07C 303/40; C07C 311/06; C07C 311/13; C07C 311/46; C07D 207/06; C07D 211/16; C07D 213/64; C07D 277/30; C07D 295/10
See application file for complete search history.

(56) References Cited

OTHER PUBLICATIONS

Amor et al. (1994) "Identification of epitopes of myelin oligodendrocyte glycoprotein for the induction of experimental allergic encephalomyelitis in SJL and Biozzi AB/H mice," Journal of Immunology. 153:4349-4356.
Baker et al. (2000) "Cannabinoids control spasticity and tremor in a multiple sclerosis model," Nature. 404:84-87.
Barbara et al. (2009) "T-type calcium channel inhibition underlies the analgesic effects of the endogenous lipoamino acids," J. Neurosci. 29:13106-13114.
Barnes et al. (2003) "Spasticity in multiple sclerosis," Neurorehabil Neural Repair. 17:66-70.
Baur et al. (Sep. 10, 2013) "Do N-arachidonyl-glycine (NA-glycine) and 2-arachidonoyl glycerol (2-AG) share mode of action and the binding site on the beta2 subunit of GABAA receptors?" PeerJ. 1:e149. pp. 1-15.
Berge et al. (1977) "Pharmaceutical Salts," J. Pharm. Sci. 66(1):1-19.
Bondarenko et al. (May 27, 2013) "N-arachidonoyl glycine suppresses Na(+) /Ca(2+) exchanger-mediated Ca(2+) entry into endothelial cells and activates BKCa channels independently of GPCRs," British Journal of Pharmacology. 169:933-948.
Boulenguez et al. (2010) "Down-regulation of the potassium-chloride cotransporter KCC2 contributes to spasticity after spinal cord injury," Nat. Med. 16:302-307.
Bradshaw et al. (2009) "The endocannabinoid anandamide is a precursor for the signaling lipid N-arachidonoyl glycine by two distinct pathways," BMC Biochem. 10:14. pp. 1-11.
Brooks et al. (2002) "Arvanil-induced inhibition of spasticity and persistent pain: evidence for therapeutic sites of action different from the vanilloid VR1 receptor and cannabinoid CB(1)/CB(2) receptors," European Journal of Pharmacology. 439:83-92.
Burstein et al. (2000) "Oxidative metabolism of anandamide," Prostaglandins Other Lipid Mediat. 61:29-41.
Butter et al. (1991) "Mononuclear cell trafficking and plasma protein extravasation into the CNS dueing chronic relapsing experimental allergic encephalomyelitis in Biozzi AB/H mice," Journal of Neurology Science. 104:9-12.
Collongues et al. (Feb. 2013) "Multiple sclerosis spasticity: 'state-of-the-art' questionnaire survey of specialized healthcare professionals," Expert Rev. Neurother. 13:21-25.
Daniel et al. (1983) "Relation between the increase in the diffusional permeability of the blood-central nervous system barrier and other changes during the develoment of experimental allergic encephalomyelitis in the Lewis rat," Journal of Neurological Science. 60:367-376.
Deak et al. (2012) "The endocannabinoid N-arachidonoyl glycine (NAGly) inhibits store-operated Ca2+ entry by preventing STIM1-Orai1 interaction," J. Cell Sci. 126:879-888.
Fox et al. (2001) "The role of central and peripheral Cannabinoid1 receptors in the antiperalgesic activity of cannabinoids in a model of neuropahtic pain," Pain. 92:91-100.
Hemmett et al. (2004) "What drives quality of life in multiple sclerosis?" QJM 97:671-676.
Hoi et al. (2007) "Vascular pharmacology of a novel cannabinoid-like compound, 3-(5-dimethylcarbamoyl-pent-1-enyl)-N-(2-hydroxy-1-methyl-ethyl)benzamide (VSN16) in the rat," British Journal of Pharmacology. 152:751-764.
Huang et al. (2001) "Identification of a new class of molecules, the arachidonyl amino acids, and characterization of one member that inhibits pain," J. Biol. Chem. 276:42639-42644.
Izzo et al. (2000) "Central and peripheral cannabinoid modulation of gastrointestinal transit in physiological states or during the diarrhoea induced by croton oil," British Journal of Pharmacology. 129:1627-1632.
Jacus et al. (2012) "Presynaptic Cav3.2 channels regulate excitatory neurotransmission in nociceptive dorsal horn neurons," J. Neurosci. 32:9374-9382.
Juhler et al. (1984) "Blood-brain and blood-spinal cord barrier permeability during the course of experimental allergic encephaomyelitis in the rat," Brain Research. 302:347-355.
Lambert et al. (Sep. 17, 2013) "The many faces of T-type calcium channels," Pflugers Arch.—Eur. J. Physiol. 466:415-423.
Landi et al. (2002) "Modulation of gastric emptying and gastrointestinal transit in rats through intesting cannabinoid CB1 receptors," European Journal of Pharmacology. 450:77-83.
McCue et al. (2008) "Cytochrome c catalyzes the in vitro synthesis of arachidonoyl glycine," Biochem. Biophys. Res. Commun. 365:322-327.

(56) References Cited

OTHER PUBLICATIONS

Oreja-Guevara et al. (Feb. 18, 2013) "Spasticity in multiple sclerosis: results of a patient survey," Int. J. Neurosci. 123:400-408.
Parmar et al. (2010) "N-arachidonoyl glycine, an endogenous lipid that acts as a vasorelaxant via nitric oxide and large conductance calcium-activated potassium channels," British Journal of Pharmacology. 160:594-603.
Pinto et al. (2002) "Endocannabinoids as physiological regulators of colonic propulsion in mice," Gastroenterology. 123:227-234.
Prusakiewicz et al. (2002) "Selective oxygenation of N-arachidonylglycine by cyclooxygenase-2," Biochem. Biophys. Res. Commun. 296:612-617.
Rees et al. (2006) "Mutations in the gene encoding GlyT2 (SLC6A5) define a presynaptic component of human startle disease," Nat. Genet. 38:801-806.
Rizzo et al. (2004) "Prevalence and treatment of spasticity reported by multiple sclerosis patients," Mult. Scler. 10:589-595.
Ross et al. (2009) "Inhibition of human recombinant T-type calcium channels by the endocannabinoid N-arachidonoyl dopamine," British Journal of Pharmacology. 156:740-750.
Succar et al. (2007) "Actions of N-arachidonyl-glycine in a rat inflammatory pain model," Molecular Pain. 3:24. pp. 1-8.
Visintin et al. (2005) "Membrane receptor probes: solid-phase synthesis of biotin-Asp-PEG-arvanil derivatives," Org. Lett. 7:1699-1702.
Von Wegerer et al. (2003) "Spinal inhibitory synaptic transmission in the glycine receptor mouse mutant spastic," Neurosci. Lett. 345:45-48.
Vuong et al. (2008) "Actions of N-arachidonyl-glycine in a rat neuropathic pain model," Neuropharmacology. 54:189-193.
Ward et al. (1990) "Pravadoline: profile in isolated tissue preparations," J. Pharmacol. Exp. Ther. 255:1230-1239.
Wiles et al. (2006) "N-Arachidonyl-glycine inhibits the glycine transporter, GLYT2a," J. Neurochem. 99:781-786.
Xiong et al. (Apr. 11, 2012) "A common molecular basis for exogenous and endogenous cannabinoid potentiation of glycine receptors," J. Neurosci. 32:5200-5208.
Yang et al. (2008) "Subunit-specific modulation of glycine receptors by cannabinoids and N-arachidonyl-glycine," Biochem. Pharmacol. 76:1014-1023.
Yevenes et al. (2011) "Molecular sites for the positive allosteric modulation of glycine receptors by endocannabinoids," PloS One. 6:e23886. pp. 1-14.
Thou et al. (2002) "Murine peripherin gene sequences direct Cre recominbinase expressionto peripheral neurons in transgenic mice," FEBS Lett. 523:68-72.
International Search Report corresponding to International Patent Application No. PCT/GB2014/053626, dated Jun. 2, 2015.
Written Opinion corresponding to International Patent Application No. PCT/GB2014/053626, dated Jun. 2, 2015.

* cited by examiner

BENZAMIDE DERIVATIVES USEFUL IN THE TREATMENT OF MUSCULAR DISORDERS AND PAIN AND FOR CONTROLLING SPASTICITY AND TREMORS

RELATED APPLICATIONS

This application is a 35 U.S.C. § 371 filing of International Application No. PCT/GB2014/053626, filed Dec. 5, 2014, which claims priority to Great Britain Patent Application No. 1321601.5, filed Dec. 6, 2013, the contents of which are incorporated herein by reference in their entireties for all purposes.

The present invention relates to compounds useful in the treatment of muscular disorders, or for controlling spasticity or tremors.

BACKGROUND TO THE INVENTION

Spasticity in Multiple Sclerosis (MS)

Spasticity is a motor disorder clinically defined as a velocity-dependent increase in muscle tone resulting from hyperexcitable stretch reflexes, spasms and hypersensitivity to normally innocuous sensory stimulations. The intermittent or sustained involuntary muscle hyperactivity that characterises spasticity is associated with upper motor neurone lesions that can be located anywhere along the path of the corticospinal (pyramidal) tracts. This includes the motor pathways of the cortex, basal ganglia, thalamus, cerebellum, brainstem or spinal cord.

Spasticity in MS is characterised by stiffness in one or more muscle groups, due to over excitation. It may be accompanied by spasms, which are often painful, and controlled movement becomes difficult. Spasticity is a common feature of MS with 40-84% of patients reporting mild to severe spasticity in different studies (Barnes M P, Kent R M, Semlyen J K, McMullen K M (2003), Neurorehabil Neural Repair 17:66-70; Hemmett L, Holmes J, Barnes M, Russell N (2004), QJM 97:671-676; Rizzo M A, Hadjimichael O C, Preiningerova J, Vollmer T L (2004), Mult Scler 10:589-595; Collongues N, Vermersch P (2013), Expert Rev Neurother 13:21-25, 2013; Oreja-Guevara C, Gonzalez-Segura D, Vila C (2013), Int J Neurosci 123:400-408). Spasticity in MS is associated with a decrease in patient life quality. Current drugs used to treat spasticity include Baclofen, a $GABA_A$ agonist, Tizanidine, an alpha2 adrenergic agonist, Dantrolene, a drug that acts on muscle sarcolamella and Sativex, a cannabinoid receptor 1 (CB1) agonist. All these drugs show less than optimal control of symptoms and are accompanied by moderate to severe side effects such as sedation, muscle weakness or have the potential for abuse. Thus poor tolerance and under-treatment result in unmet needs in MS spasticity management.

Mechanisms of Spasticity

The aetiology of spasticity in MS has been relatively little studied. This is in contrast to spasticity caused by spinal cord injury, where the control of chloride homeostasis has recently been invoked as a key mechanism mediating spasticity (Boulenguez P, Liabeuf S, Bos R, Bras H, Jean-Xavier C, Brocard C, Stil A, Darbon P, Cattaert D, Delpire E, Marsala M, Vinay L (2010), Nat Med 16:302-307). A complex system of channels and transporters controls neuronal excitability versus inhibitory signalling in the spinal cord. Low intracellular chloride ion concentrations are thought to mediate inhibitory signalling and concentrations of chloride are maintained at a low level by the potassium/chloride ion transporter KCC2. At these low concentrations of chloride opening of $GABA_A$ channels and glycine channels serve to increase chloride concentrations and cause a hyperpolarising current. Following spinal cord injury KCC2 becomes downregulated, chloride levels increase and glycine mediates depolarization. While many details remain to be elucidated, the overall effect is to diminish the inhibitory signal to the muscles leading to excessive excitability, contraction and spasticity. As such, deficiency in the glycine receptor in mice leads to neurological abnormalities in early juvenile life in a mouse called the Spastic mouse (von Wegerer J, Becker K, Glockenhammer D, Becker C M, Zeilhofer H U, Swandulla D (2003), Neurosci Lett 345:45-48).

To study MS related spasticity, a chronic relapsing EAE model has been developed (Baker D, Pryce G, Croxford J L, Brown P, Pertwee R G, Huffman J W, Layward L (2000), Nature 404:84-87). Efficacy in this system was demonstrated by Baclofen, endocannabinoids and cannabinoids, and has been translated to the treatment of MS. Intriguing new evidence now points to modulatory sites on glycine channels (GlyRs) for endocannabinoids (Yevenes G E, Zeilhofer H U (2011), PLoS One 6:e23886) and these may contribute to the effect on spasticity. The functions of glycine signalling have been primarily studied in pain, however it has been shown that methanandamide, the synthetic analogue of the endogenous cannabinoid anandamide, can alleviate spasticity in the chronic relapsing EAE model (Brooks J W, Pryce G, Bisogno T, Jaggar S I, Hankey D J, Brown P, Bridges D, Ledent C, Bifulco M, Rice A S, Di Marzo V, Baker D (2002), Eur J Pharmacol 439:83-92). Studies on analogues of anandamide have identified molecules with notable anti-spastic activity in the chronic relapsing EAE model, such as VSN16 (see Visintin C, Aliev A E, Riddall D, Baker D, Okuyama M, Hoi P M, Hiley R, Selwood D L (2005), Org Lett 7:1699-1702, 2005; Hoi P M, Visintin C, Okuyama M, Gardiner S M, Kaup S S, Bennett T, Baker D, Selwood D L, Hiley C R (2007), Br J Pharmacol 152:751-764).

VSN-16 was first disclosed in WO 2005/080316 (in the name of University College London). Initial studies demonstrated that VSN16 exhibits a marked effect on spasticity in CREAE mice, providing strong evidence that a selective inhibition of spasticity is achieved without producing significant adverse CNS effects.

With regard to the involvement of glycine in spasticity mechanisms, mutations in the glycine receptor demonstrate an important role in the control of muscle tone as shown by studies in mouse strains (Oscillator, Spasmodic and Spastic). The archetypal glycine antagonist, strychnine causes severe muscle cramps. A hyperekplexic response (an exaggerated startle response to tactile or acoustic stimuli) is observed in humans with similar mutations. Similar responses have now been shown in humans with mutations in the glycine transporter GlyT2a (Rees M I, Harvey K, Pearce B R, Chung S K, Duguid I C, Thomas P, Beatty S, Graham G E, Armstrong L, Shiang R, Abbott K J, Zuberi S M, Stephenson J B, Owen M J, Tijssen M A, van den Maagdenberg A M, Smart T G, Supplisson S, Harvey R J (2006), Nat Genet 38:801-806).

The present invention seeks to provide new compounds that have therapeutic applications in the treatment of muscular disorders, particularly for controlling spasticity and/or tremors.

STATEMENT OF INVENTION

A first aspect of the invention relates to a compound of formula I, or a pharmaceutically acceptable salt or prodrug thereof,

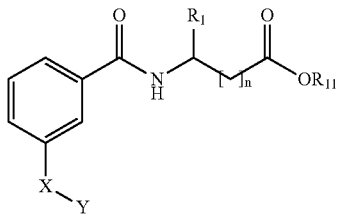

wherein:

n is 0 or 1;

R¹ is selected from H, alkyl and aralkyl, wherein said alkyl and aralkyl groups may be optionally substituted by one or more OH groups;

X is a group selected from

—C≡C—(CH$_2$)$_p$—;
—C(R$^5$)=C(R$^6$)—(CH$_2$)$_q$—; and
—C(R$^5$)(R$^6$)C(R$^7$)(R$^8$)—(CH$_2$)$_r$—;

where each of R$^5$, R$^6$, R$^7$ and R$^8$ is independently H or alkyl, and each of p, q and r is independently 1, 2, 3, 4 or 5;

Y is a group selected from:

CN;

COOR$^2$;

CONR$^3$R$^4$;

SO$_2$NR$^9$R$^{10}$;

NR$^{12}$COR$^{13}$;

NR$^{14}$SO$_2$R$^{15}$; and a heterocyclic group selected from oxadiazolyl, thiazolyl, iso-thiazolyl, oxazolyl, iso-oxazolyl, pyrazolyl and imidazolyl;

where each of R$^2$, R$^3$ and R$^4$ is independently H or alkyl; or R$^3$ and R$^4$ are linked, together with the nitrogen to which they are attached, to form a 5 or 6-membered heterocycloalkyl or heterocycloalkenyl group, said heterocycloalkyl or heterocycloalkenyl group optionally containing one or more further groups selected from O, N, CO and S, and where each of R$^9$, R$^{10}$, R$^{11}$, R$^{12}$, R$^{13}$, R$^{14}$ and R$^{15}$ is independently H or alkyl.

Advantageously, a number of the presently claimed compounds exhibit one or more of the following properties: improved potency/activity, improved selectivity, improved distribution, improved aqueous solubility or decreased lipophilicity and/or reduced rates of metabolism.

A second aspect of the invention relates to a compound of formula I, or a pharmaceutically acceptable salt thereof, for use in treating a muscular disorder.

A third aspect of the invention relates to a compound of formula I, or a pharmaceutically acceptable salt thereof, for use in controlling spasticity and tremors, or for treating bladder spasticity.

A fourth aspect of the invention relates to a compound of formula I, or a pharmaceutically acceptable salt thereof, for use in treating pain.

A fifth aspect of the invention relates to a pharmaceutical composition comprising a compound of formula I as defined above admixed with a pharmaceutically acceptable diluent, excipient or carrier.

A sixth aspect of the invention relates to a process for preparing compounds of formula I.

DETAILED DESCRIPTION

Compounds

The present invention relates to compounds of formula I as defined herein, and pharmaceutically acceptable salts and prodrugs thereof.

As used herein, the term "alkyl" includes both saturated straight chain and branched alkyl groups which may be substituted (mono- or poly-) or unsubstituted. Preferably, the alkyl group is a $C_{1-20}$ alkyl group, more preferably a $C_{1-15}$, more preferably still a $C_{1-10}$ alkyl group, more preferably still, a $C_{1-6}$ alkyl group or a $C_{1-4}$ alkyl group. Particularly preferred alkyl groups include, for example, methyl, ethyl, propyl, isopropyl, butyl, isobutyl, tert-butyl, pentyl and hexyl. Suitable substituents include, for example, alkyl, hydroxy, halo-, alkoxy-, nitro-, COOH, CO$_2$-alkyl, alkenyl, CN, NH$_2$ and CF$_3$.

As used herein, the term "cycloalkyl" refers to a cyclic alkyl group which may be substituted (mono- or poly-) or unsubstituted. Preferably, the cycloalkyl group is a $C_{3-6}$-cycloalkyl group. Suitable substituents include, for example, alkyl, hydroxy, halo-, alkoxy-, nitro-, COOH, CO$_2$-alkyl, alkenyl, CN, NH$_2$ and CF$_3$.

As used herein, the term "alkenyl" refers to group containing one or more double bonds, which may be branched or unbranched, and substituted (mono- or poly-) or unsubstituted. Preferably the alkenyl group is a $C_{2-20}$ alkenyl group, more preferably a $C_{2-15}$ alkenyl group, more preferably still a $C_{2-10}$ alkenyl group, or preferably a $C_{2-6}$ alkenyl group. Suitable substituents include, for example, alkyl, hydroxy, halo-, alkoxy-, nitro-, COOH, CO$_2$-alkyl, alkenyl, CN, NH$_2$ and CF$_3$.

As used herein, the term "aryl" refers to a $C_{6-10}$ aromatic group which may be substituted (mono- or poly-) or unsubstituted. Typical examples include phenyl and naphthyl etc. Suitable substituents include, for example, alkyl, hydroxy, halo-, alkoxy-, nitro-, COOH, CO$_2$-alkyl, alkenyl, CN, NH$_2$ and CF$_3$.

As used herein, the term "aralkyl" includes, but is not limited to, a group having both aryl and alkyl functionalities. By way of example, the term includes groups in which one of the hydrogen atoms of the alkyl group is replaced by an aryl group, e.g. a phenyl group optionally having one or more substituents such as halo, alkyl, alkoxy, hydroxy, and the like. Typical aralkyl groups include benzyl, phenethyl and the like.

As used herein, the term "heterocycle" (also referred to herein as "heterocyclyl" and "heterocyclic") refers to a substituted (mono- or poly-) or unsubstituted saturated, unsaturated or partially unsaturated cyclic group containing one or more heteroatoms selected from N, O and S, and which optionally further contains one or more CO groups. Suitable substituents include, for example, halo, alkyl, alkoxy, hydroxy, and the like. The term "heterocycle" encompasses both heteroaryl groups and heterocycloalkyl groups as defined below.

As used herein, the term "heteroaryl" refers to a $C_{2-12}$ aromatic, substituted (mono- or poly-) or unsubstituted group, which comprises one or more heteroatoms. Preferably, the heteroaryl group is a $C_{4-12}$ aromatic group comprising one or more heteroatoms selected from N, O and S. Suitable heteroaryl groups include pyrrole, pyrazole, pyrimidine, pyrazine, pyridine, quinoline, thiophene, 1,2,3- triazole, 1,2,4-triazole, thiazole, oxazole, iso-thiazole, iso-oxazole, imidazole, furan and the like. Suitable substituents include, for example, alkyl, hydroxy, halo-, alkoxy-, nitro-, COOH, $CO_2$-alkyl, alkenyl, CN, $NH_2$, $CF_3$ and cyclic groups.

As used herein, the term "heterocycloalkyl" refers to a substituted (mono- or poly-) or unsubstituted cyclic aliphatic group which contains one or more heteroatoms. Preferred heterocycloalkyl groups include piperidinyl, pyrrolidinyl, piperazinyl, thiomorpholinyl and morpholinyl. More preferably, the heterocycloalkyl group is selected from N-piperidinyl, N-pyrrolidinyl, N-piperazinyl, N-thiomorpholinyl and N-morpholinyl.

As used herein, the term "heterocycloalkenyl" refers to a substituted (mono- or poly-) or unsubstituted cyclic group which contains one or more heteroatoms and one or more carbon-carbon double bonds.

In one preferred embodiment, the invention relates to a compound of formula I, or a pharmaceutically acceptable salt or prodrug thereof, wherein:
n is 0 or 1;
$R^1$ is selected from H, alkyl and aralkyl, wherein said alkyl and aralkyl groups may be optionally substituted by one or more OH groups;
X is a group selected from
  —C≡C—$(CH_2)_p$—;
  —$C(R^5)$=$C(R^6)$—$(CH_2)_q$—; and
  —$C(R^5)(R^6)C(R^7)(R^8)$—$(CH_2)_r$—;
where each of $R^5$, $R^6$, $R^7$ and $R^8$ is independently H or alkyl, and each of p, q and r is independently 2, 3, or 4;
Y is a group selected from:
  CN;
  $COOR^2$;
  $CONR^3R^4$;
  $SO_2NR^9R^{10}$; and
  a heterocyclic group selected from oxadiazolyl, thiazolyl, iso-thiazolyl, oxazolyl, iso-oxazolyl, pyrazolyl and imidazolyl;
where each of $R^2$, $R^3$ and $R^4$ is independently H or alkyl; or $R^3$ and $R^4$ are linked, together with the nitrogen to which they are attached, to form a 5 or 6-membered heterocycloalkyl group, said heterocycloalkyl group optionally containing one or more further heteroatoms selected from O, N and S, and where each of $R^9$ and $R^{10}$ is independently H or alkyl.

In one preferred embodiment, $R^1$ is selected from H, Me, Et, $^n$Pr, $^i$Pr, $CH_2$-phenyl, $CH_2$-[4-(OH)-phenyl], $CH_2OH$, $CH(OH)CH_3$, $CH(CH_3)CH_2CH_3$ and $CH_2CH(CH_3)_2$. More preferably, $R^1$ is H, $CH_2OH$, Me, Et or $CH_2$-phenyl.

In one preferred embodiment, Y is selected from CN, $CON(Me)_2$, CONHMe, CONHEt, $SO_2N(Me)_2$, N(Me)COMe, $N(Me)SO_2Me$, CO-piperidinyl, CO-pyrrolidinyl, oxadiazolyl and thiazolyl. Preferably, Y is thiazol-4-yl.

In one highly preferred embodiment, Y is $CON(Me)_2$.

In one preferred embodiment, each of p, q and r is independently 2, 3, or 4.

In one preferred embodiment, X is —C≡C—$(CH_2)_p$—, where p is 1, 2, 3, 4, or 5.

In one preferred embodiment, X— is cis —$C(R^5)$=$C(R^6)$—$(CH_2)_q$— and q is 2, 3 or 4.

In one preferred embodiment, X is —CH=CH—$(CH_2)_q$— and q is 2 or 3.

In one preferred embodiment, X is —$C(R^5)(R^6)C(R^7)(R^8)$—$(CH_2)_r$— and r is 2, 3 or 4.

In one preferred embodiment, X is —$CH_2$—$CH_2$—$(CH_2)_r$— and r is 2 or 3.

In one preferred embodiment, $R_{11}$ is H.

In another preferred embodiment, $R_{11}$ is $C_{1-6}$-alkyl, more preferably, Me or Et, even more preferably, Me.

In one preferred embodiment, the compound of the invention is of formula Ia, or a pharmaceutically acceptable salt thereof,

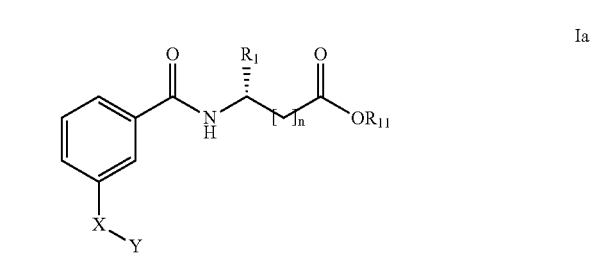

Ia wherein $R^1$, $R^{11}$, X, Y and n are as defined above. In one preferred embodiment, $R_{11}$ is H.

In one preferred embodiment, the compound of the invention is of formula Ib, or a pharmaceutically acceptable salt thereof,

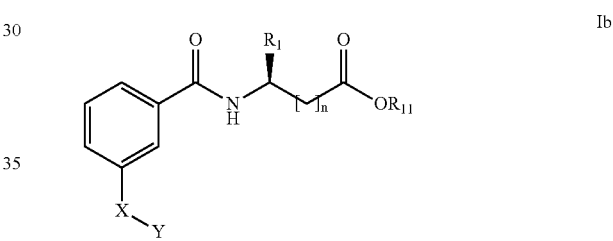

Ib wherein $R^1$, $R^{11}$, X, Y and n are as defined above. In one preferred embodiment, $R_{11}$ is H.

In one preferred embodiment, n is 0.

In one preferred embodiment, n is 1.

In one preferred embodiment, $R^1$ is Me.

In one preferred embodiment, $R^1$ is $CH_2OH$.

In one preferred embodiment, $R^1$ is $CH_2Ph$.

In one preferred embodiment, $R^1$ is H.

In one preferred embodiment, n is 0, $R^1$ is Me and X is —CH=CH—$(CH_2)_3$— or —$CH_2$—$CH_2$—$(CH_2)_3$—.

In one preferred embodiment, n is 1 or 2 and $R^1$ is H.

In one preferred embodiment, n is 1 and $R^1$ is H.

The compounds of the present invention preferably exhibit improved aqueous solubility and/or decreased lipophilicity compared to prior art cannabinoid modulators. Preferably, the compounds of the invention do not cross the blood-brain barrier to any substantial extent.

The compounds of the invention were evaluated using a mouse vas deferens study and in vivo in mice. Further details of the binding studies may be found in the accompanying Examples section.

In one preferred embodiment of the invention, the compound is selected from the following:

[1]
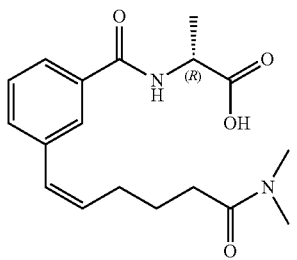
[2]
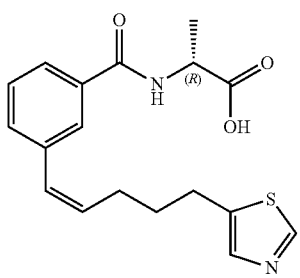
[3]
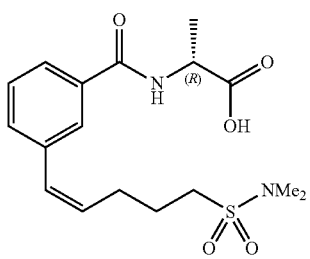
[4]
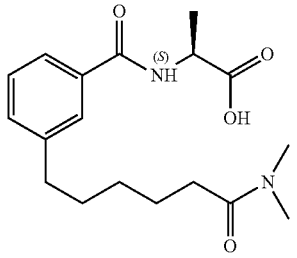
[5]
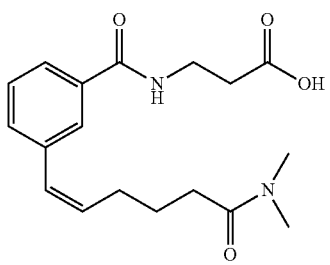
[6]
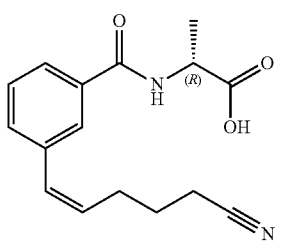
-continued
[7]
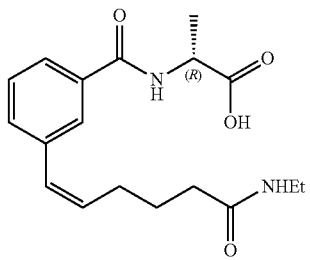
[8]
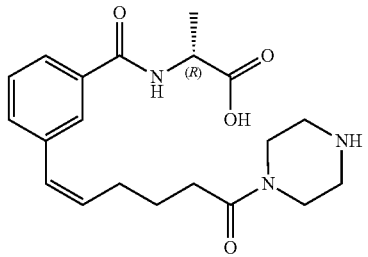
[9]
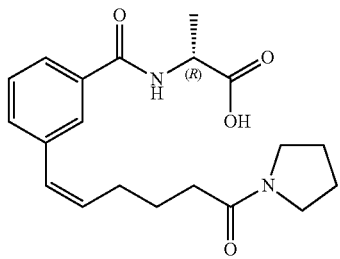
[10]
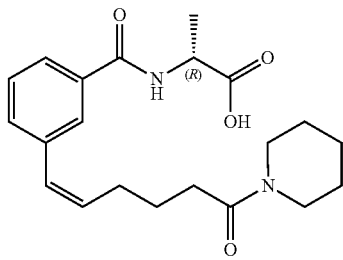
[11]
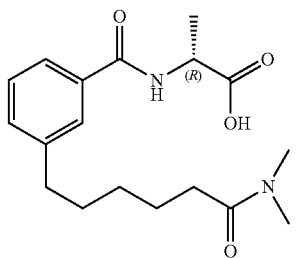
[12]
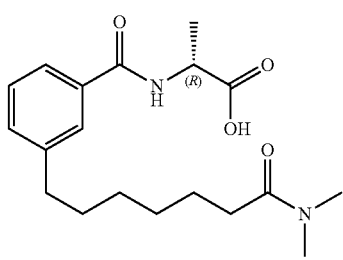

[13]
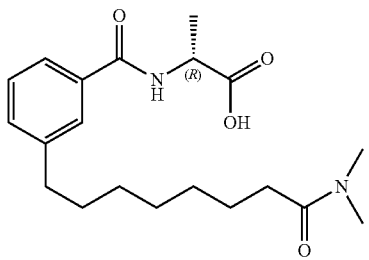
[14]
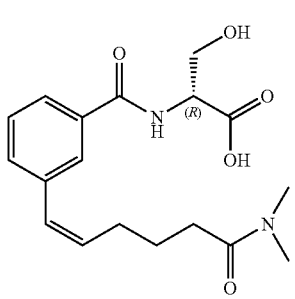
[15]
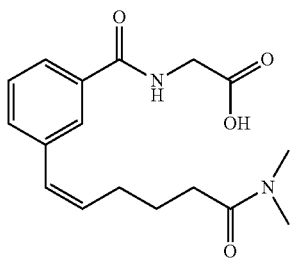
[16]
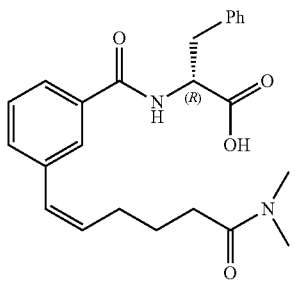
[17]
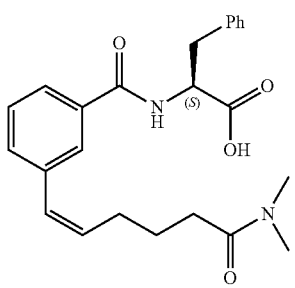
[18]
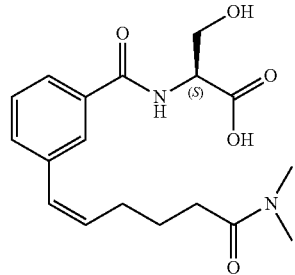
[19]
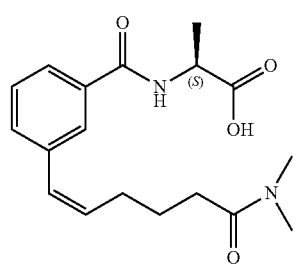
[20]
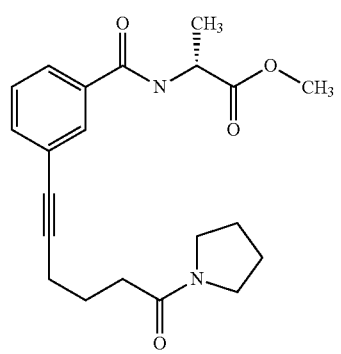
[21]
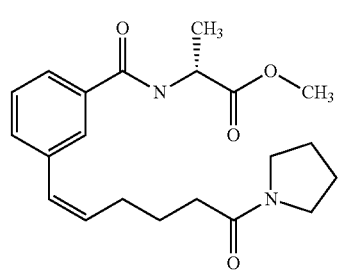
[22]
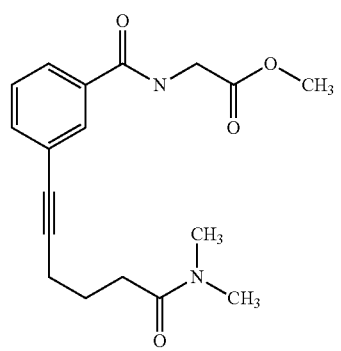

[23]
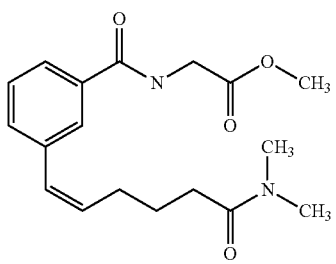
[24]
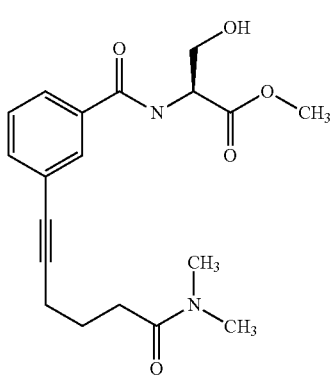
[25]
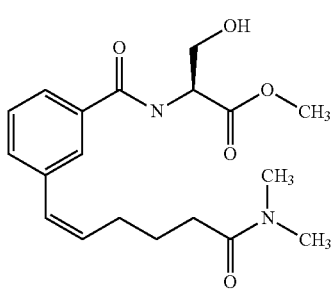
[26]
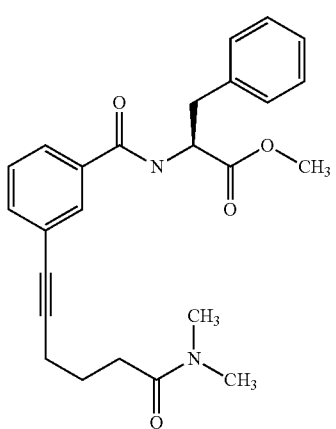
[27]
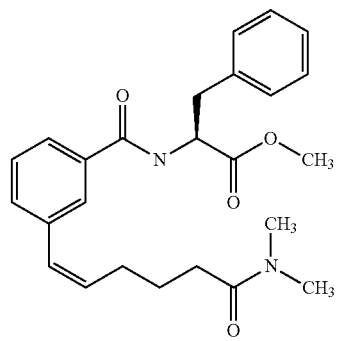
[28]
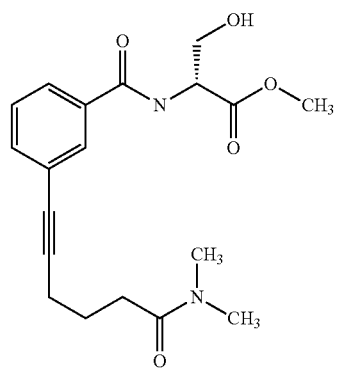
[29]
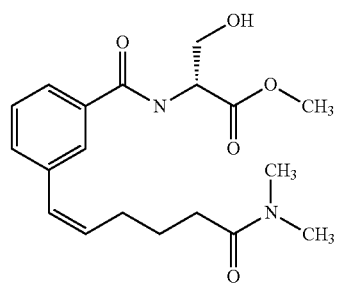
[30]
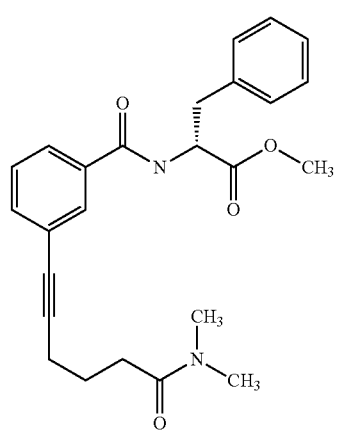

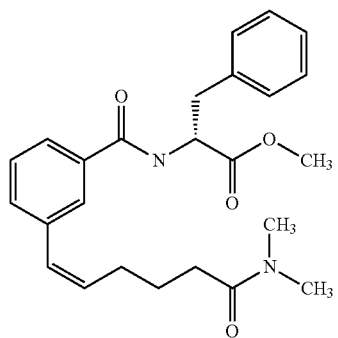
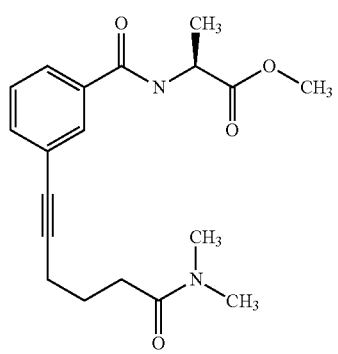
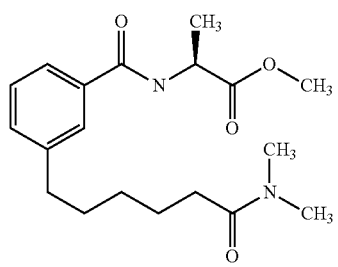
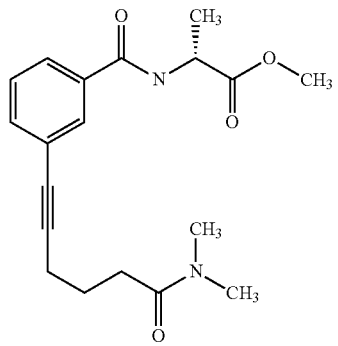
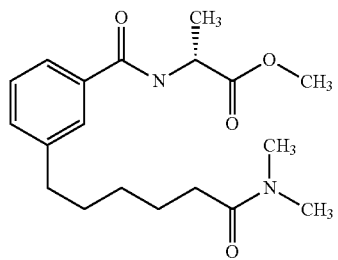
[31]
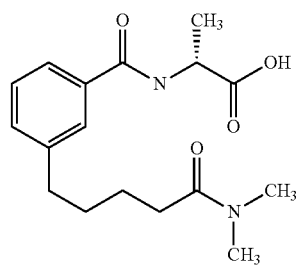
[32]
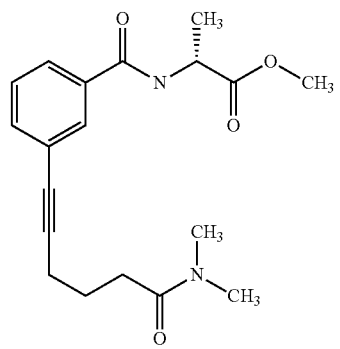
[33]
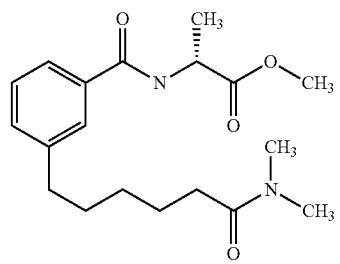
[34]
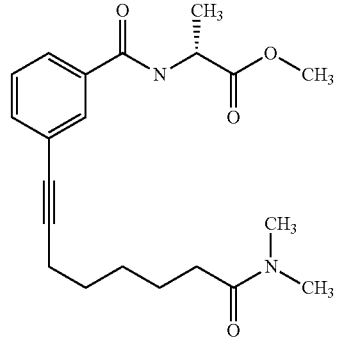
[35]
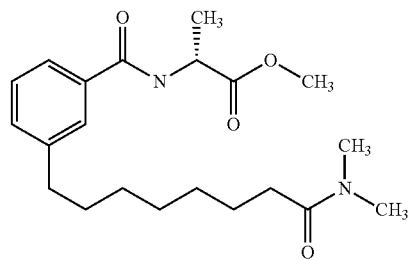

[41] 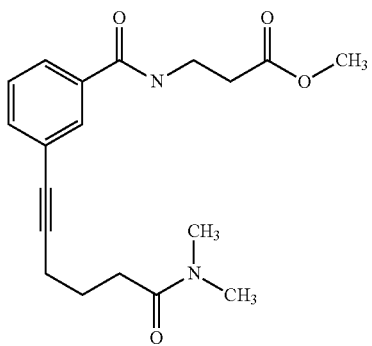
[42] 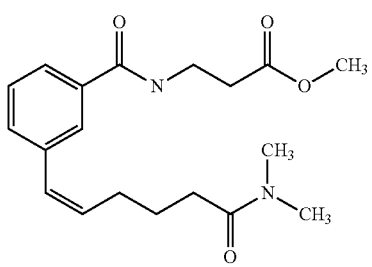
[43] 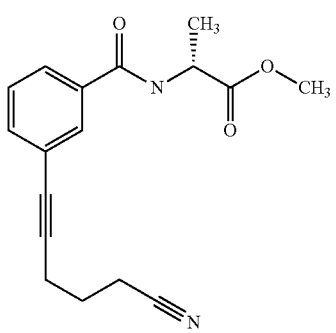
[44] 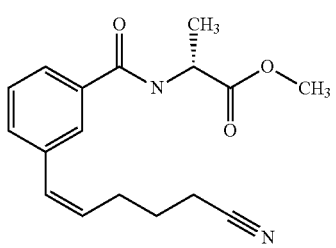
[45] 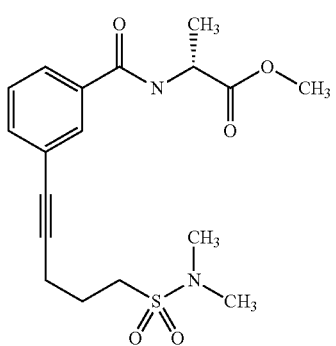
[46] 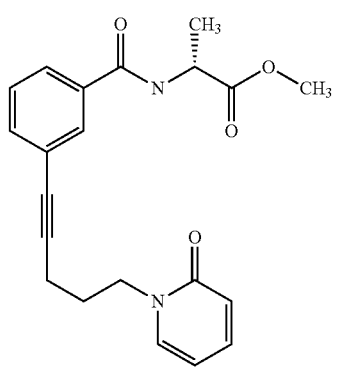
[47] 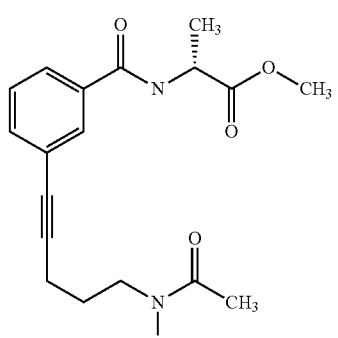
[48] 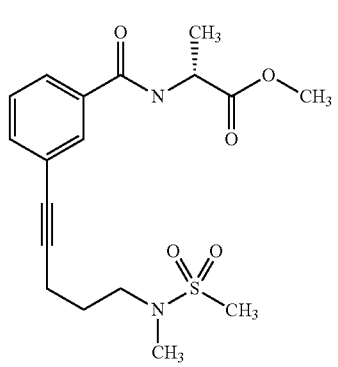
[49] 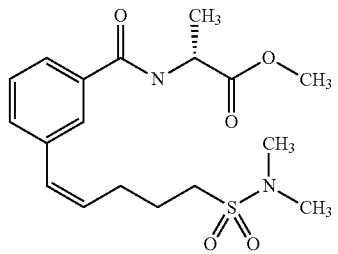
[50] 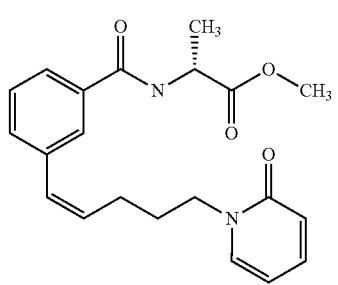

[51] 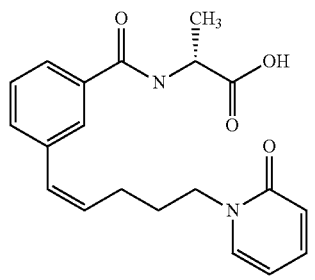

[52] 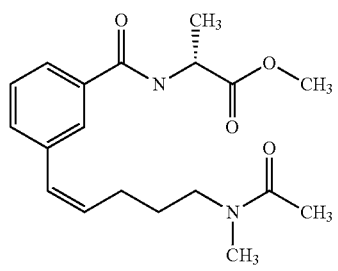

[53] 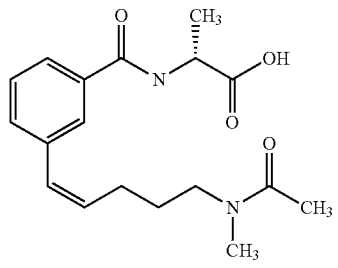

[54] 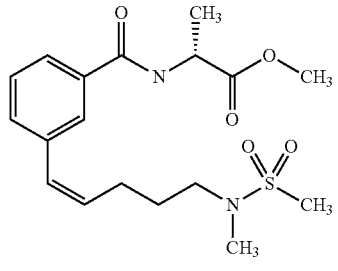

[55] 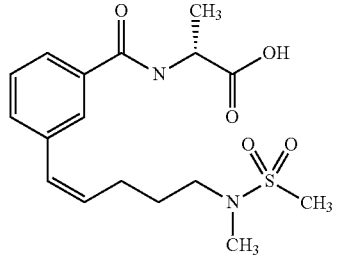

and pharmaceutically acceptable salt, prodrugs and enantiomers thereof, and mixtures of said enantiomers. In the table above, and in the structures shown throughout the specification, for ease of presentation the hydrogen on the amide nitrogen is not always shown. However, a person skilled in organic chemistry would clearly understand the nature of the chemical structures depicted.

Especially preferred compounds of the invention are selected from the following:

[1] 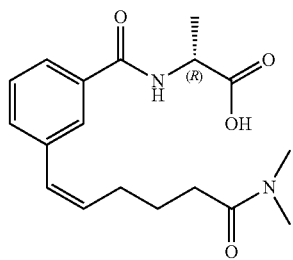

[2] 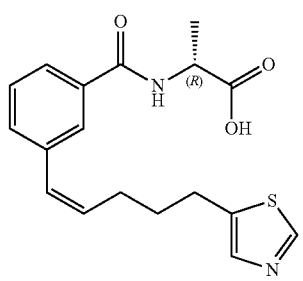

[3] 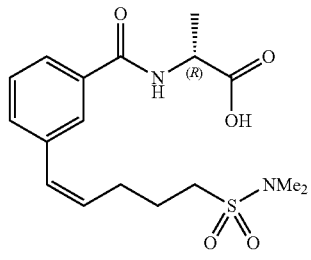

[4] 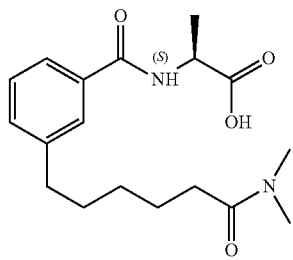

[5] 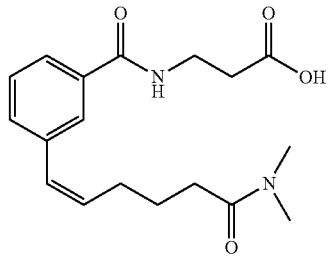

[6] 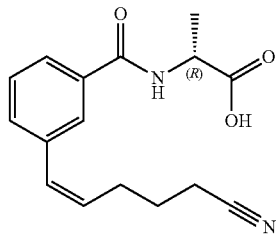

[7] 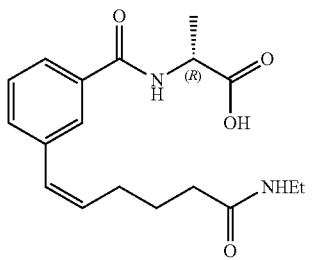
[8] 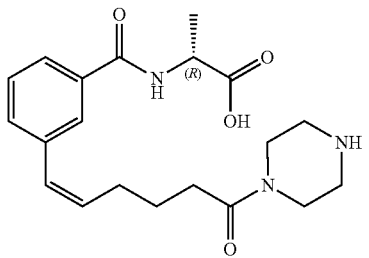
[9] 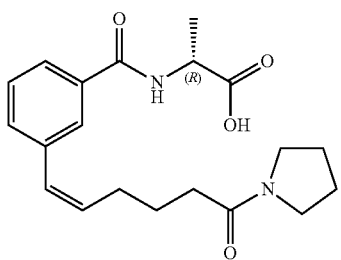
[10] 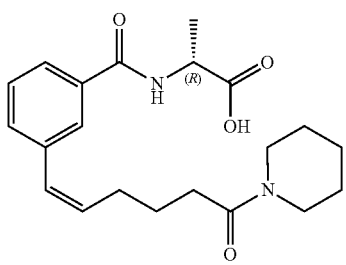
[11] 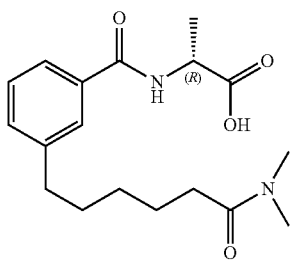
[12] 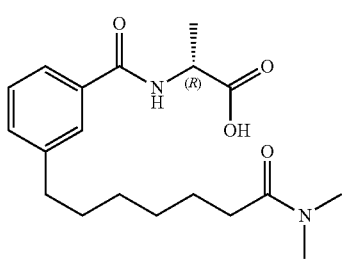
[13] 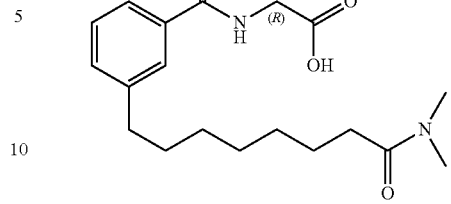
[14] 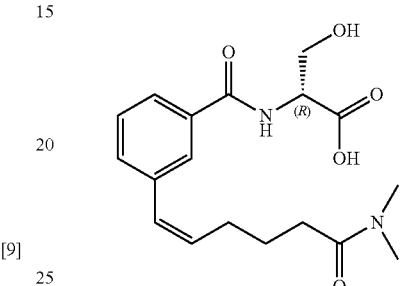
[15] 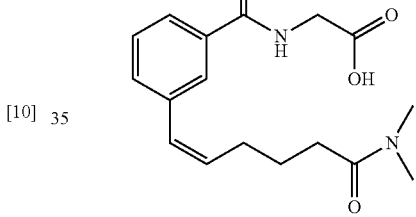
[16] 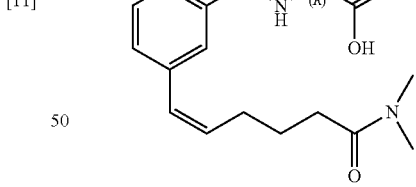
[17] 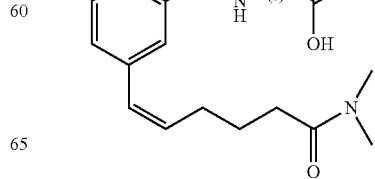

-continued

[18]

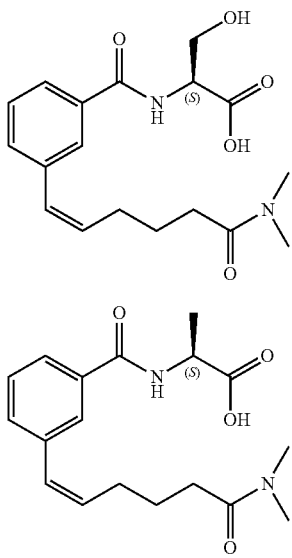

[19]

and pharmaceutically acceptable salt, prodrugs and enantiomers thereof, and mixtures of said enantiomers.

In one especially preferred embodiment, the compound is of the formula [1], or a pharmaceutically acceptable salt or prodrug thereof:

[1]

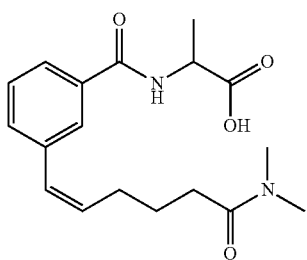

Advantageously, compound [1] has been shown to exhibit a 10-fold greater potency ($EC_{50}$) than VSN-16R based on studies in the vas deferens mouse assay.

More preferably still, the compound is of the formula [1a] or formula [1b], or a mixture thereof:

[1a]

[1b]

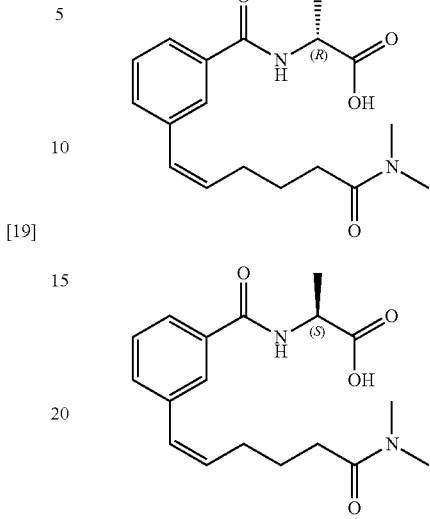

In one preferred embodiment, the compound is a racemic mixture of compounds [1a] and [1b].

In another preferred embodiment, the compound is selected from the following: [1], [20], [21], [22], [23], [15], [24], [25], [18], [27], [17], [29], [14], [30], [31], [16] and [32].

In another preferred embodiment, the compound is selected from the following: [1], [23], [27], [29], [30], [31], [16] and [32].

In another preferred embodiment, the compound is selected from the following: [1] and [16].

Synthesis

A further aspect of the invention relates to a process for preparing a compound of formula I.

In a preferred embodiment, the process is for preparing a compound of formula I as defined above, which is of formula (VIII), wherein $R^1$ and n are as defined above, said process comprising the steps of:

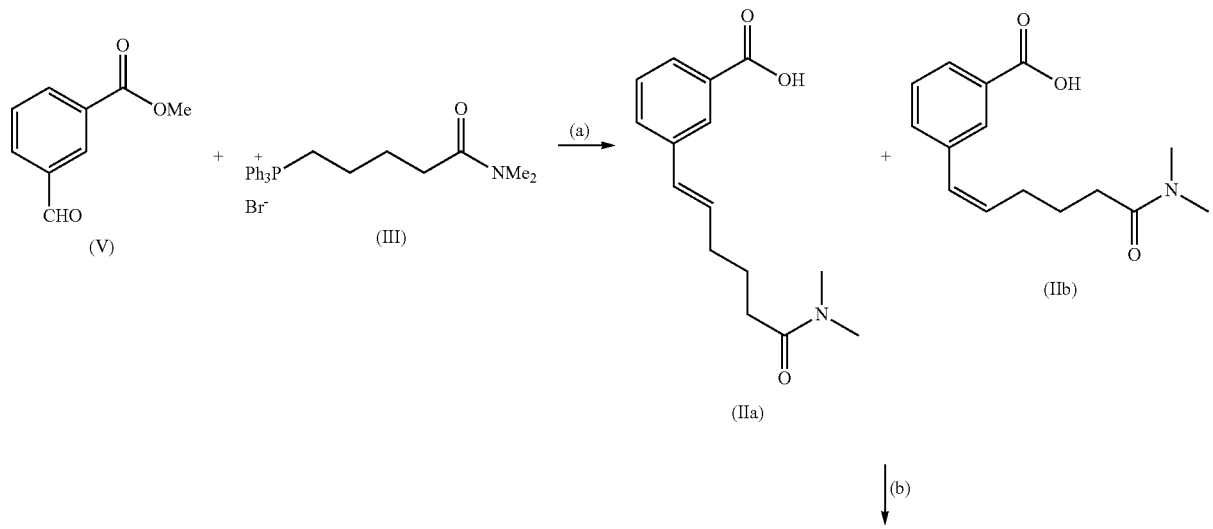

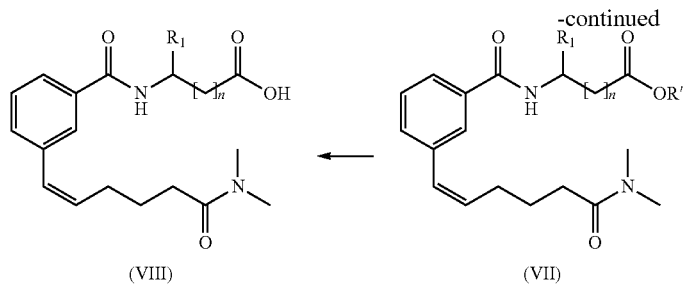

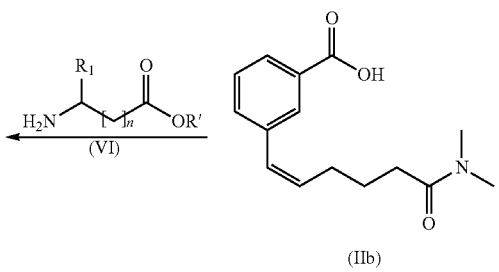

(i) coupling a compound of formula (V) with a compound of formula (IIIa) to form a mixture comprising compounds of formulae (IIa) and (IIB);
(II) separating said compound of formula (IIb) from the mixture obtained in step (i);
(iii) treating the compound of formula (IIb) obtained in step (ii) with a compound of formula (VI), where $R^1$ and n are as defined in claim 1, and R' is alkyl, to form a compound of formula (VII); and
(iv) converting said compound of formula (VII) to a compound of formula (VIII).

In one preferred embodiment, step (i) comprises dissolving said compound of formula (III) in a suitable solvent (e.g. dichloromethane), adding potassium hexamethyldisilazide thereto, and then adding a solution of methyl 3-formylbenzoate (V) to the mixture so formed.

In one preferred embodiment, step (ii) comprises dissolving the mixture of (IIa) and (IIb) in ethyl acetate and adding thereto a solution of dimethylaminopyridine (DMAP) dissolved in ethyl acetate, refluxing the mixture and then allowing to cool to room temperature.

In one preferred embodiment, step (iii) comprises dissolving said compound of formula (IIb) in a suitable solvent (e.g. DMF) and adding thereto said compound of formula (VI) in a suitable solvent (e.g. DMF) and benzotriazol-1-yl-oxytripyrrolidino-phosphonium hexafluorophosphate (Py-BOP) in a suitable solvent (e.g. DMF), followed by the addition of an amine base (preferably N,N-diisopropylethylamine, DIPEA).

In one preferred embodiment, step (iv) comprises dissolving said compound of formula (VII) in a suitable solvent (preferably THF) and adding to lithium hydroxide hydrate in water and stirring.

An alternative aspect of the invention relates to a process for preparing a compound of formula I as defined above which is of formula (VIII), wherein $R^1$ and n are as defined in claim 1, said process comprising the steps of:

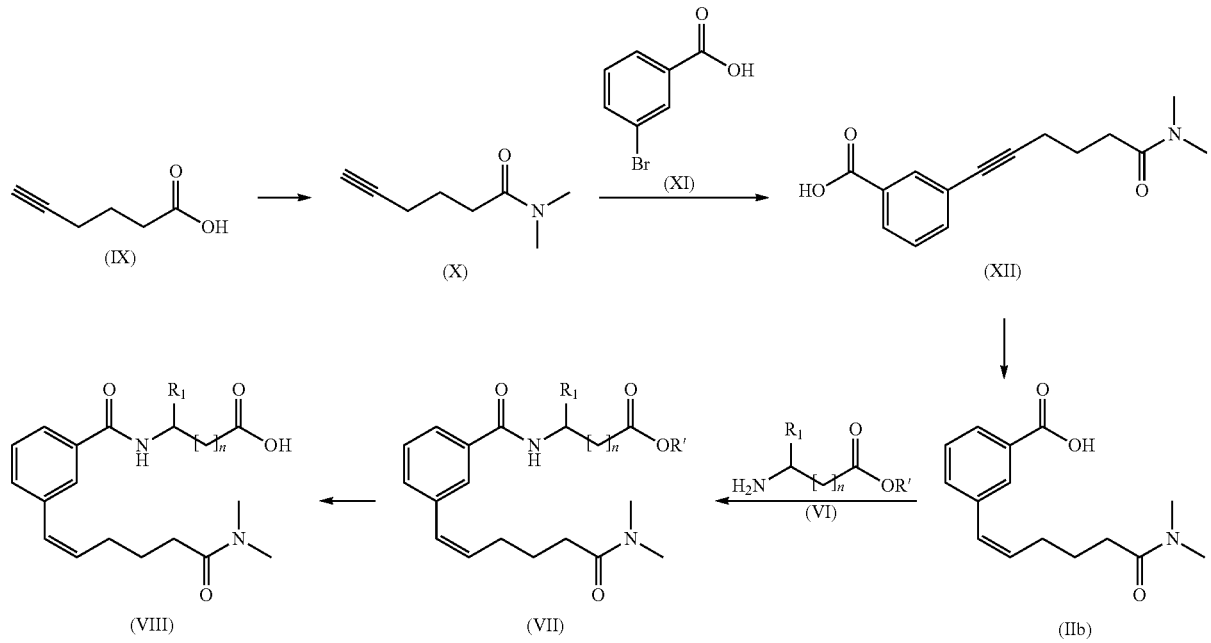

(i) treating a compound of formula (IX) with dimethylamine to form a compound of formula (X);
(ii) reacting said compound of formula (X) with a compound of formula (XI) to form a compound of formula (XII);
(iii) hydrogenating said compound of formula (XII) to form a compound of formula (IIb);
(iv) treating said compound of formula (IIb) with a compound of formula (VI), where $R^1$ and n are as defined in claim 1, and R' is alkyl, to form a compound of formula (VII); and
(v) converting said compound of formula (VII) to a compound of formula (VIII).

Preferably, step (ii) comprises a Sonagashira coupling reaction carried out in the presence of a palladium catalyst, more preferably dichlorobis(triphenylphosphine) palladium (II).

Therapeutic Applications

Another aspect of the invention relates to a compound of formula I for use in treating a muscular disorder, for controlling spasticity and tremors, or for treating bladder spasticity.

Another aspect relates to the use of a compound of formula I according to the invention in the preparation of a medicament for treating a muscular disorder. Preferably, the muscular disorder is a neuromuscular disorder.

As used herein the phrase "preparation of a medicament" includes the use of a compound of formula I directly as the medicament in addition to its use in a screening programme for further agents or in any stage of the manufacture of such a medicament.

The term "muscular disorder" is used in a broad sense to cover any muscular disorder or disease, in particular a neurological disorder or disease, more particularly, a neurodegenerative disease or an adverse condition involving neuromuscular control. Thus, the term includes, for example, gastic hypermotility, CREAE, multiple sclerosis (MS), spasticity, Parkinson's disease, Huntingdon's Chorea, spinal cord injury, including spinal cord spasticity, epilepsy, Tourettes' syndrome, and bladder spasm. Although there is no clear role for peripheral cannabinoid receptors in controlling spasticity in multiple sclerosis and EAE, the blood: CNS barriers are compromised in lesional areas and may provide selective access of therapeutic agents [Butter, C. et al, *J. Neurol. Sci.* 1991, 104, 9-12; Daniel, P. M. et al, *J. Neurol. Sci.* 1983, 60, 367-376; Juhler, M. et al, *Brain Res.* 1984, 302, 347-355].

Peripheral $CB_1$ receptors are known to modulate gastrointestinal motility, intestinal secretion and gastroprotection. The digestive tract contains endogenous cannabinoids (anandamide and 2-arachidonoylglycerol), and cannabinoid $CB_1$ receptors can be found on myenteric and submucosal nerves. Activation of prejunctionally/presynaptically-located enteric (intestinal) $CB_1$ receptors produces inhibition of electrically-induced contractions (an effect which is associated to inhibition of acetylcholine release from enteric nerves) in various isolated intestinal tissues, including the human ileum and colon. Cannabinoid agonists inhibit intestinal motility in rodents in vivo and this effect is mediated, at least in part, by activation of peripheral (i.e. intestinal) $CB_1$ receptors, both in the upper gastrointestinal transit [Izzo, A. A. et al, Br. *J. Pharmacol.* 2000, 129, 1627-1632; Landi, M. et al, *Eur. J. Pharmacol.* 2002, 450, 77-83] and in the colon [Pinto, L. et al, *Gastroenterology* 2002, 123, 227-234]. Thus, measurement of intestinal motility, in vivo is a useful model for evaluating the activity of peripheral-acting cannabinoid drugs.

In addition to the aforementioned disorders, the present invention also has applications in other fields where tremor or muscle spasm is present or is manifested, such as incontinence, asthma, bronchial spasms, hic-coughs etc.

Another aspect relates to the use of a compound of formula I according to the invention in the preparation of a medicament for controlling spasticity and tremors, or for treating bladder spasticity.

Bladder spasticity (also called automatic bladder, reflex bladder) is a form of neurogenic bladder caused by a lesion of the spinal cord above the voiding reflex center. It is marked by loss of bladder control and bladder sensation, bladder overactivity, incontinence, and automatic, interrupted, incomplete voiding of urine. It is most often caused by trauma but may result from a tumour, multiple sclerosis or trauma.

In one highly preferred embodiment, the compound of the invention is for use in treating spasticity in MS.

The compounds of the invention also have therapeutic applications in the treatment of pain. Preferably, the pain is neuropathic pain or inflammatory pain.

Pharmaceutical Compositions

A further aspect of the invention relates to a pharmaceutical composition comprising a compound of the invention, or pharmaceutically acceptable salt thereof, as defined above admixed with a pharmaceutically acceptable diluent, excipient or carrier. Even though the compounds of the present invention (including their pharmaceutically acceptable salts, esters and pharmaceutically acceptable solvates) can be administered alone, they will generally be administered in admixture with a pharmaceutical carrier, excipient or diluent, particularly for human therapy. The pharmaceutical compositions may be for human or animal usage in human and veterinary medicine.

Examples of such suitable excipients for the various different forms of pharmaceutical compositions described herein may be found in the "Handbook of Pharmaceutical Excipients, $2^{nd}$ Edition, (1994), Edited by A Wade and P J Weller.

Acceptable carriers or diluents for therapeutic use are well known in the pharmaceutical art, and are described, for example, in Remington's Pharmaceutical Sciences, Mack Publishing Co. (A. R. Gennaro edit. 1985).

Examples of suitable carriers include lactose, starch, glucose, methyl cellulose, magnesium stearate, mannitol and sorbitol. Examples of suitable diluents include ethanol, glycerol and water.

The choice of pharmaceutical carrier, excipient or diluent can be selected with regard to the intended route of administration and standard pharmaceutical practice. The pharmaceutical compositions may comprise as, or in addition to, the carrier, excipient or diluent any suitable binder(s), lubricant(s), suspending agent(s), coating agent(s), solubilising agent(s).

Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol.

Examples of suitable lubricants include sodium oleate, sodium stearate, magnesium stearate, sodium benzoate, sodium acetate and sodium chloride.

Preservatives, stabilizers, dyes and even flavoring agents may be provided in the pharmaceutical composition. Examples of preservatives include sodium benzoate, sorbic acid and esters of p-hydroxybenzoic acid. Antioxidants and suspending agents may be also used.

Salts/Esters

The compounds of the invention can be present as salts or esters, in particular pharmaceutically acceptable salts or esters.

Pharmaceutically acceptable salts of the compounds of the invention include suitable acid addition or base salts thereof. A review of suitable pharmaceutical salts may be found in Berge et al, J Pharm Sci, 66, 1-19 (1977). Salts are formed, for example with strong inorganic acids such as mineral acids, e.g. sulphuric acid, phosphoric acid or hydrohalic acids; with strong organic carboxylic acids, such as alkanecarboxylic acids of 1 to 4 carbon atoms which are unsubstituted or substituted (e.g., by halogen), such as acetic acid; with saturated or unsaturated dicarboxylic acids, for example oxalic, malonic, succinic, maleic, fumaric, phthalic or tetraphthalic; with hydroxycarboxylic acids, for example ascorbic, glycolic, lactic, malic, tartaric or citric acid; with aminoacids, for example aspartic or glutamic acid; with benzoic acid; or with organic sulfonic acids, such as ($C_1$-$C_4$)-alkyl- or aryl-sulfonic acids which are unsubstituted or substituted (for example, by a halogen) such as methane- or p-toluene sulfonic acid.

Esters are formed either using organic acids or alcohols/hydroxides, depending on the functional group being esterified. Organic acids include carboxylic acids, such as alkanecarboxylic acids of 1 to 12 carbon atoms which are unsubstituted or substituted (e.g., by halogen), such as acetic acid; with saturated or unsaturated dicarboxylic acid, for example oxalic, malonic, succinic, maleic, fumaric, phthalic or tetraphthalic; with hydroxycarboxylic acids, for example ascorbic, glycolic, lactic, malic, tartaric or citric acid; with aminoacids, for example aspartic or glutamic acid; with benzoic acid; or with organic sulfonic acids, such as ($C_1$-$C_4$)-alkyl- or aryl-sulfonic acids which are unsubstituted or substituted (for example, by a halogen) such as methane- or p-toluene sulfonic acid. Suitable hydroxides include inorganic hydroxides, such as sodium hydroxide, potassium hydroxide, calcium hydroxide, aluminium hydroxide. Alcohols include alkanealcohols of 1-12 carbon atoms which may be unsubstituted or substituted, e.g. by a halogen).

Enantiomers/Tautomers

In all aspects of the present invention previously discussed, the invention includes, where appropriate all enantiomers and tautomers of compounds of formula I. The man skilled in the art will recognise compounds that possess optical properties (one or more chiral carbon atoms) or tautomeric characteristics. The corresponding enantiomers and/or tautomers may be isolated/prepared by methods known in the art. Thus, the invention encompasses the enantiomers and/or tautomers in their isolated form, or mixtures thereof, such as for example, racemic mixtures of enantiomers.

Stereo and Geometric Isomers

Some of the specific agents of the invention may exist as stereoisomers and/or geometric isomers—e.g. they may possess one or more asymmetric and/or geometric centres and so may exist in two or more stereoisomeric and/or geometric forms. The present invention contemplates the use of all the individual stereoisomers and geometric isomers of those inhibitor agents, and mixtures thereof. The terms used in the claims encompass these forms, provided said forms retain the appropriate functional activity (though not necessarily to the same degree).

The present invention also includes all suitable isotopic variations of the agent or a pharmaceutically acceptable salt thereof. An isotopic variation of an agent of the present invention or a pharmaceutically acceptable salt thereof is defined as one in which at least one atom is replaced by an atom having the same atomic number but an atomic mass different from the atomic mass usually found in nature. Examples of isotopes that can be incorporated into the agent and pharmaceutically acceptable salts thereof include isotopes of hydrogen, carbon, nitrogen, oxygen, phosphorus, sulphur, fluorine and chlorine such as $^2H$, $^3H$, $^{13}C$, $^{14}C$, $^{15}N$, $^{17}O$, $^{18}O$, $^{31}P$, $^{32}P$, $^{35}S$, $^{18}F$ and $^{36}Cl$, respectively. Certain isotopic variations of the agent and pharmaceutically acceptable salts thereof, for example, those in which a radioactive isotope such as $^3H$ or $^{14}C$ is incorporated, are useful in drug and/or substrate tissue distribution studies. Tritiated, i.e., $^3H$, and carbon-14, i.e., $^{14}C$, isotopes are particularly preferred for their ease of preparation and detectability. Further, substitution with isotopes such as deuterium, i.e., $^2H$, may afford certain therapeutic advantages resulting from greater metabolic stability, for example, increased in vivo half-life or reduced dosage requirements and hence may be preferred in some circumstances. Isotopic variations of the agent of the present invention and pharmaceutically acceptable salts thereof of this invention can generally be prepared by conventional procedures using appropriate isotopic variations of suitable reagents.

Solvates

The present invention also includes solvate forms of the compounds of the present invention. The terms used in the claims encompass these forms.

Polymorphs

The invention furthermore relates to the compounds of the present invention in their various crystalline forms, polymorphic forms and (an)hydrous forms. It is well established within the pharmaceutical industry that chemical compounds may be isolated in any of such forms by slightly varying the method of purification and or isolation form the solvents used in the synthetic preparation of such compounds.

Prodrugs

The invention further includes the compounds of the present invention in prodrug form. Such prodrugs are generally compounds of formula I wherein one or more appropriate groups have been modified such that the modification may be reversed upon administration to a human or mammalian subject. Such reversion is usually performed by an enzyme naturally present in such subject, though it is possible for a second agent to be administered together with such a prodrug in order to perform the reversion in vivo. Examples of such modifications include ester (for example, any of those described above, for example, methyl or ethyl esters of the acids), wherein the reversion may be carried out be an esterase etc. Other such systems will be well known to those skilled in the art.

In one highly preferred embodiment, the prodrug is an ester of said compound of formula I, more preferably a methyl or ethyl ester. For example, the free COOH group of the compound of formula I is esterified to form a $COOR^{11}$ group, where $R^{11}$ is a $C_{1-6}$-alkyl group.

Administration

The pharmaceutical compositions of the present invention may be adapted for oral, rectal, vaginal, parenteral, intramuscular, intraperitoneal, intraarterial, intrathecal, intrabronchial, subcutaneous, intradermal, intravenous, nasal, buccal or sublingual routes of administration.

For oral administration, particular use is made of compressed tablets, pills, tablets, gellules, drops, and capsules. Preferably, these compositions contain from 1 to 250 mg and more preferably from 10-100 mg, of active ingredient per dose.

Other forms of administration comprise solutions or emulsions which may be injected intravenously, intraarterially, intrathecally, subcutaneously, intradermally, intraperitoneally or intramuscularly, and which are prepared from sterile or sterilisable solutions. The pharmaceutical compositions of the present invention may also be in form of suppositories, pessaries, suspensions, emulsions, lotions, ointments, creams, gels, sprays, solutions or dusting powders.

An alternative means of transdermal administration is by use of a skin patch. For example, the active ingredient can be incorporated into a cream consisting of an aqueous emulsion of polyethylene glycols or liquid paraffin. The active ingredient can also be incorporated, at a concentration of between 1 and 10% by weight, into an ointment consisting of a white wax or white soft paraffin base together with such stabilisers and preservatives as may be required.

Injectable forms may contain between 10-1000 mg, preferably between 10-250 mg, of active ingredient per dose.

Compositions may be formulated in unit dosage form, i.e., in the form of discrete portions containing a unit dose, or a multiple or sub-unit of a unit dose. In addition, the compositions may be formulated as extended release formulations.

Dosage

A person of ordinary skill in the art can easily determine an appropriate dose of one of the instant compositions to administer to a subject without undue experimentation. Typically, a physician will determine the actual dosage which will be most suitable for an individual patient and it will depend on a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy. The dosages disclosed herein are exemplary of the average case. There can of course be individual instances where higher or lower dosage ranges are merited, and such are within the scope of this invention.

Depending upon the need, the agent may be administered at a dose of from 0.01 to 30 mg/kg body weight, such as from 0.1 to 10 mg/kg, more preferably from 0.1 to 1 mg/kg body weight.

In an exemplary embodiment, one or more doses of 10 to 150 mg/day will be administered to the patient.

Combinations

In a particularly preferred embodiment, the one or more compounds of the invention are administered in combination with one or more other pharmaceutically active agents. In such cases, the compounds of the invention may be administered consecutively, simultaneously or sequentially with the one or more other pharmaceutically active agents.

The present invention is further described by way of example, and with reference to the following figures wherein.

EXAMPLES

General Procedures

Figure 1:
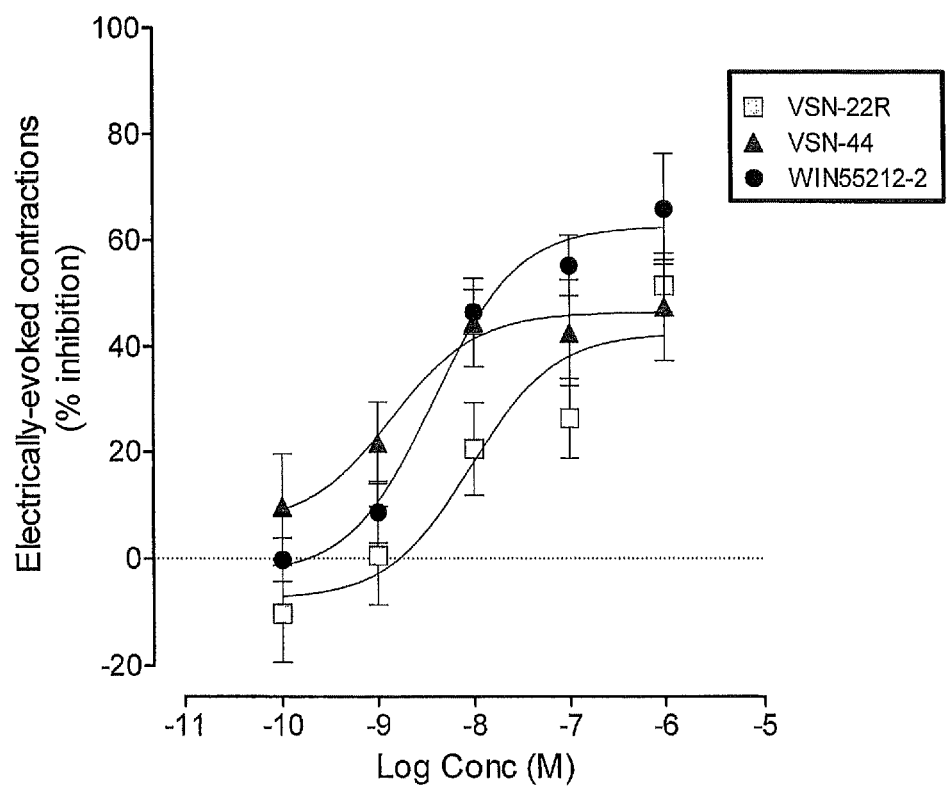
FIG. 1 shows inhibition of electrically-evoked contractions of the mouse vas deferens by WIN55, VSN-22R and VSN-44.

All starting materials and solvents were obtained either from commercial sources or prepared according to the literature citation. Unless otherwise stated all reactions were stirred.

Normal phase column chromatography was routinely carried out on an automated flash chromatography system such as CombiFlash Companion or CombiFlash RF system. Intermediates were purified using pre-packed silica (230-400 mesh, 40-63 µm) cartridges and products of a Lindlar reduction using pre-packed GraceResolv flash cartridges. SCX was purchased from Supelco or Silicycle (40-63 µm size, 0.78 mmol/g loading).

Analytical Methods

Analytical HPLC was carried out using a Waters Xselect CSH C18, 2.5 µm, 4.6×30 mm column eluting with a gradient of 0.1% Formic Acid in MeCN in 0.1% aqueous Formic Acid; a Waters Xbridge BEH C18, 2.5 µm, 4.6×30 mm column eluting with a gradient of MeCN in aqueous 10 mM Ammonium Bicarbonate. UV spectra of the eluted peaks were measured using either a diode array or variable wavelength detector on an Agilent 1100 system.

Analytical LCMS was carried out using a Waters Xselect CSH C18, 2.5 µm, 4.6×30 mm column eluting with a gradient of 0.1% Formic Acid in MeCN in 0.1% aqueous Formic Acid; a Waters Xbridge BEH C18, 2.5 µm, 4.6×30 mm column eluting with a gradient of MeCN in aqueous 10 mM Ammonium Bicarbonate. UV and mass spectra of the eluted peaks were measured using a variable wavelength detector on either an Agilent 1200 with or an Agilent Infinity 1260 LCMS with 6120 single quadrupole mass spectrometer with positive and negative ion electrospray.

Preparative HPLC was carried out using a Waters Xselect CSH C18, 5 µm, 19×50 mm column using either a gradient of either 0.1% Formic Acid in MeCN in 0.1% aqueous Formic Acid or a gradient of MeCN in aqueous 10 mM Ammonium Bicarbonate; or a Waters Xbridge BEH C18, 5 µm, 19×50 mm column using a gradient MeCN in aqueous 10 mM Ammonium Bicarbonate; or the compounds were purified by reverse-phase HPLC (Gilson) using preparative C-18 column (Hypersil PEP 100×21 mm internal diameter, 5 µm particle size, and 100 Å pore size) and isocratic gradient over 20 minutes. Fractions were collected following detection by UV at a single wavelength measured by a variable wavelength detector on a Gilson 215 preparative HPLC or Varian PrepStar preparative HPLC; by mass and UV at a single wavelength measured by a ZQ single quadrupole mass spectrometer, with positive and negative ion electrospray, and a dual wavelength detector on a Waters FractionLynx LCMS.

$^1$H NMR Spectroscopy: $^1$H NMR spectra were acquired on a Bruker Avance III spectrometer at 400 MHz. The central peak of dimethylsulfoxide-$d_6$ was used as reference.

Abbreviations

AcOH glacial acetic acid
aq. aqueous
br broad
d doublet
dd doublet of doublets
ddd double double doublet
dt doublet of triplets
DCM dichloromethane
DIPEA diisopropylethylamine
DMF dimethylformamide
DMSO dimethyl sulfoxide
(ES+) electrospray ionization, positive mode
Et ethyl
Et$_3$N triethylamine
EtOAc ethyl acetate
EtOH ethanol
HATU 2-(1H-7-azabenzotriazol-1-yl)-1,1,3,3-tetramethyluronium hexafluorophosphate
HCl hydrochloric acid
HPLC high performance liquid chromatography
hr hour(s)
Hz hertz
LC liquid chromatography
(M+H)+ protonated molecular ion
M molar
m multiplet
Me methyl
MeCN acetonitrile
MeOH methanol
MgSO$_4$ magnesium sulphate
MHz megahertz
min minute(s)
MS mass spectrometry
m/z: mass-to-charge ratio Na₂SO₄ sodium sulphate
NMR nuclear magnetic resonance (spectroscopy)
Ph phenyl
ppm parts per million
q quartet
qn quintet
rt room temperature
HPLC high performance liquid chromatography
s singlet
sat. saturated
SCX solid supported cation exchange (resin)
t triplet
td triplet of doublets
TEA triethylamine
THF tetrahydrofuran
TLC thin layer chromatography
wt % weight percent
Prefixes n-, s-, t- and tert- have their usual meanings: normal, secondary, iso, and tertiary.

General Method for Amide Coupling:

To a suspension of carboxylic acid (1.0 eq.), amine or amine.HCl salt (1.05-1.1 eq.) and HATU (1.1-1.3 eq.) in dry DCM (10 mL/g) was added DIPEA or TEA (2.0-3.0 eq.). The reaciton was stirred at it until complete by LCMS. The volatiles were removed in vacuo and the residue partitioned between EtOAc (20 mL/g) and sat. aq. ammonium chloride (20 mL/g). The aqueous layer was extracted with EtOAc (2×20 mL/g) before the combined organic extracts were washed with sat. aq. ammonium chloride (30 mL/g), water (30 mL/g) then brine (30 mL/g) and dried (MgSO₄ or Na₂SO₄), filtered and concentrated in vacuo. The crude material was purified by column chromatography.

General Method for Sonogashira Coupling:

To a solution of aryl iodide (1.0 eq.) and diisopropylamine (1.2 eq.) in dry THF (10 mL/g) under nitrogen was added bis(triphenylphosphine)palladium(II) chloride (4 mol %) and copper(I) iodide (7 mol %). The reaction was stirred for 5 min before alkyne (1.1-1.5 eq.) was added. The reaction was then heated at 60° C. for 1 h before the solvent was removed in vacuo and the residue partitioned between EtOAc (20 mL/g) and sat. aq. ammonium chloride (20 mL/g). The aq. layer extracted with EtOAc (2×20 mL/g) before the combined organic extracts were washed with sat. aq. ammonium chloride (20 mL/g), water (20 mL/g) and brine (20 mL/g) then dried (MgSO₄), filtered and concentrated. The crude material purified by column chromatography to yield desired coupled product.

General Method for Lindlar Reduction:

To a flask containing palladium on barium sulphate reduced (5%) (50 wt % cf. alkyne) under nitrogen was added a solution of alkyne (1.0 eq.) and quinoline (1.3 eq.) in MeOH (40 mL/g). The vessel was placed under an atmosphere of hydrogen until the reaction was deemed complete by TLC, HPLC or LCMS analysis. The catalyst was removed by filtration through celite and the quinoline was removed by filtration through SCX (washing several times with MeOH). The filtrate General Method for Ester Saponification:

To a solution of ester (1.0 eq.) in THF (10 mL/g) was added a solution of lithium hydroxide (1.5-2.0 eq.) in water (1 mL/g). The reaction was stirred at rt until judged complete by HPLC or LCMS analysis. The volatiles were removed in vacuo and the residue was partitioned with EtOAc (10 mL/g). The aqueous layer was acidified to pH 1 with 1 N citric acid and extracted with EtOAc (3×10 mL/g). The combined organic extracts were washed with water (2×10 mL/g) and brine (10 mL/g) then dried (Na₂SO₄), filtered and concentrated in vacuo.

General Procedure for Reduction of Alkyne to Alkane:

To a flask containing alkyne (1.0 eq.) in EtOH (15-20 mL/g) under nitrogen was added palladium on carbon (5 wt %) (50 wt % cf. alkyne). The mixture was placed under an atmosphere of hydrogen (2 bar) until judged complete by LCMS analysis. The catalyst was removed by filtration through celite and washed well with EtOH. The filtrate was then concentrated in vacuo and purified by chromatography to give the desired alkane product.

Preparation of VSN-44

The compound VSN-44 can be prepared by the following methodology. Other compounds of formula I can be prepared by analogous methodology using commercially available starting materials and standard synthetic steps that would be familiar to the skilled artisan, including those set forth in WO 2005/080316 and WO 2010/116116.

3-[(1Z)-6-(dimethylamino)-6-oxohex-1-en-1-yl] benzoic acid (IIb)

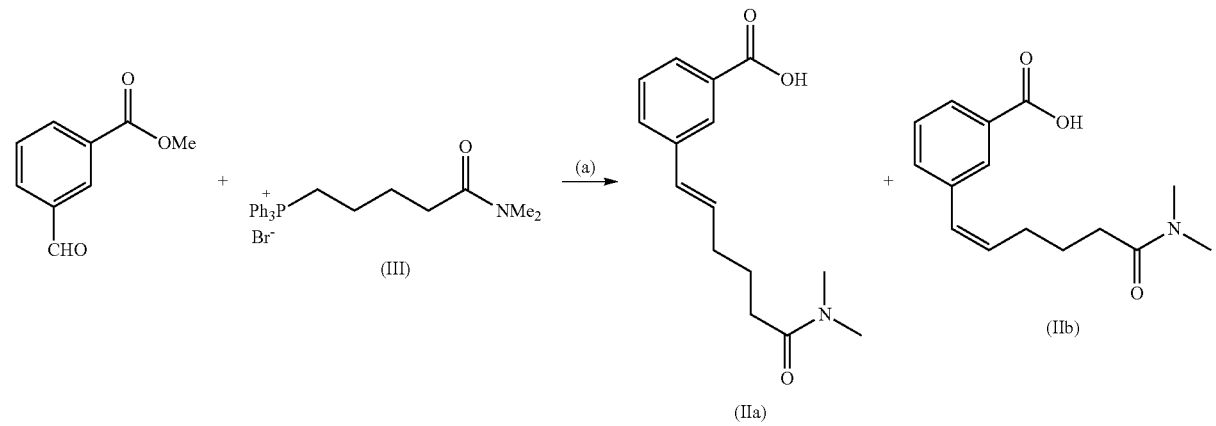

Scheme 1

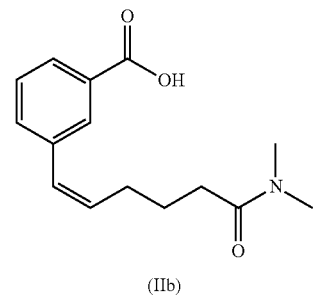

(IIb)

Scheme 1: (a) (i) anhydrous CH₂Cl₂, potassium hexamethyl disilazide, THF under N₂ atmosphere, < 10° C.; (ii) NaOH, MeOH; (b) (i) DMAP (EtOAc, Et₂O); (ii) seperation of isomers.

N,N-dimethylamino 4-(carboxybutyl)triphenylphosphonium bromide (III)

4-(carboxybutyl)triphenylphosphonium bromide (140 g, 0.315 mol, 1 equiv) was charged in a reactor and dichloromethane (650 ml, 4.5 vols) was added. Triethylamine (dried on molecular sieves; 95 ml, 2.1 equiv) was charged and the reaction mixture was cooled down to −10° C. Ethyl chloroformate (40 ml, 1.05 equiv) was added dropwise and the mixture was stirred for another 15 min at −10° C.

A solution containing dimethylamine hydrochloride (freshly crystallised from methanol/ether; 78 g, 3 equiv) and triethylamine (200 ml, 4.5 equiv) in dichloromethane (1000 ml, 7 vols) was prepared.

This solution was stirred for 40 min at room temperature and added dropwise to the reaction mixture at −10° C. The temperature was kept between −10 and −15° C. during all the addition. The reaction was left to warm up to room temperature. The reaction was stirred at room temperature overnight. The mixture was treated with 2 l of saturated NaHCO₃ solution. The aqueous phase was extracted with dichloromethane (1×2 l and 2×1 l). Organics were combined and dried over MgSO₄ and filtered. The volatiles were removed under vacuum. The residue was triturated with 350 ml of diethyl ether. The solid was filtered and triturated with hot diethyl ether for 5 hours. The suspension was cooled down and the solid filtered. The solid was dried under vacuum to give 130.9 g of a white solid (III) (90% yield).

¹H NMR (CDCl₃) 7.65-8.0 (m, 15H); 3.7 (m, 2H); 3.0 (s, 3H); 2.8 (s, 3H), 2.5 (t, J=7 Hz, 2H); 1.9 (m, 2H), 1.7 (m, 2H).

3-[(1Z)-6-(dimethylamino)-6-oxohex-1-en-1-yl] benzoic acid (IIb)

N,N-dimethylamino 4-carboxybutyltriphenylphosphonium (III) (61.9 g, 0.13 mol, 3 equivalents) were dissolved in dry dichloromethane (150 ml, 2.4 vols) under nitrogen. The solution was cooled down to 0° C. and potassium hexamethyldisilazide (0.9M in THF; 45 ml, 5 equiv) was added dropwise at 0° C. The reaction mixture was stirred at 0° C. for another 45 min. A solution of methyl 3-formylbenzoate (7.16 g, 1 equiv) in dry THF (36 ml, 5 vols) was added keeping the temperature <4° C. The mixture was allowed to warm up to room temperature and was stirred for 18 hrs. The reaction was quenched with 2M HCl (400 ml) and extracted with dichloromethane (2×400 ml and 2×200 ml). Organics were combined, dried over MgSO₄, filtered and evaporated to dryness. The residue was dissolved in a mixture of sodium hydroxide 1 M/methanol 4:1 (440 ml) and stirred for 18 hrs. Water (100 ml) was added to the mixture and methanol was evaporated under vacuum. Aqueous was extracted with ethyl acetate (400 ml). The pH was adjusted to pH 1 and the mixture was extracted with dichloromethane (2×400 ml and 2×200 ml). Organics were dried over MgSO₄, filtered and evaporated to dryness. M=22.0 g. The crude was purified by flash chromatography using dichloromethane to dichloromethane/MeOH=95/54 as eluent. M=10.6 g 93% yield.

Isomer Separation

Acid (10.93 g, 0.042 mol) was dissolved in ethyl acetate (20 ml) and 4-dimethylaminopyridine (6.13 g, 1.2 equiv) was dissolved in warm ethyl acetate (20 ml). The DMAP solution was added to the free acid solution. The mixture was stirred at reflux temperature for 10 min. Then, the solution was allowed to cool down to room temperature slowly. A brown salt was formed, which was removed by filtration.

A mixture of diethyl ether/ethyl acetate: 9:1 (40 ml) was added and the solution was heated to reflux. The mixture was stirred and allowed to cool down overnight. A pale yellow solid was filtered and dried in-vacuo. This solid was treated with HCl (1M) and extracted with dichloromethane (3×50 ml). Organics were dried over MgSO₄, filtered and evaporated to dryness to give a brown oil which solidified upon standing (IIb). M=3.88 g (35.5% yield).

1H NMR (CDCl₃) 9.7 (bs, 1H); 8.0 (m, 2H); 7.5 (m, 2H); 6.5 (d, J=11 Hz, 1H); 5.75 (m, 1H); 3.0 (s, 6H); 2.4 (m, 4H); 1.9 (m, 2H)

Preparation of VSN44

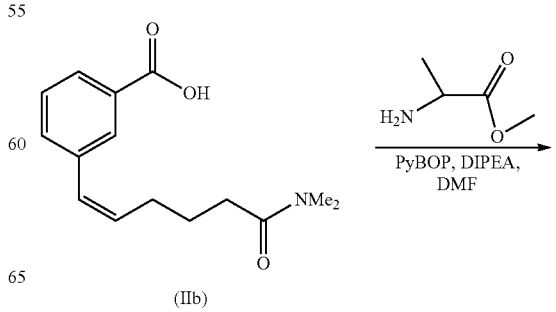

(IIb)

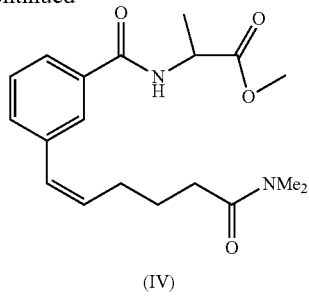

(IV)

To the substituted benzoic acid (IIb) (139 mg, 1 mmol) in DMF (1 mL) was added the Ala(OMe) in DMF (1 mL) and the PyBOP (572 mg, 1.1 mmol) added in DMF (2 mL). DIPEA (142 mg, 191 μL, 1.1 mmol) was added dropwise, and the reaction stirred at room temperature overnight. Water (50 mL) was added and ethyl acetate (100 mL). The layers were stirred (5 mins), separated, and the ethyl acetate layer washed with brine (2×100 mL), dried (Na₂SO₄) to give the crude product (650 mg). This was flash chromatographed using a 25 g Puriflash (silica) column, cyclohexane:acetone 15-45% gradient. Yield (IV) 180 mg, 0.54 mmol, 54%.

1H NMR (500 MHz, CDCl3) δ 7.77 (s, 1H), 7.71 (dt, J=1.6, 7.4, 1H), 7.42-7.38 (m, J=7.4, 1H), 7.38-7.31 (m, 2H), 6.46 (d, J=11.6, 1H), 5.74 (dt, J=7.7, 11.6, 1H), 4.84-4.76 (m, J=7.2, 1H), 3.77 (s, 3H), 2.95 (s, 3H), 2.90 (s, 3H), 2.42-2.30 (m, 4H), 1.83 (p, J=7.2, 2H), 1.64 (s, 2H), 1.54 (d, J=7.2, 3H).

13C NMR (126 MHz, CDCl3) δ 173.78, 172.63, 167.13, 137.88, 134.10, 133.23, 132.09, 128.90, 128.53, 127.12, 125.77, 52.54, 48.67, 37.30, 35.54, 32.60, 28.30, 24.99, 18.31, 17.66.

Other compounds of formula I may be prepared by substituting Ala(OMe) in the above process with other commercially available amino acid esters.

(Z)-(3-(6-(dimethylamino)-6-oxohex-1-en-1-yl)ben-zoyl)-D-alanine [1] (VSN-44)

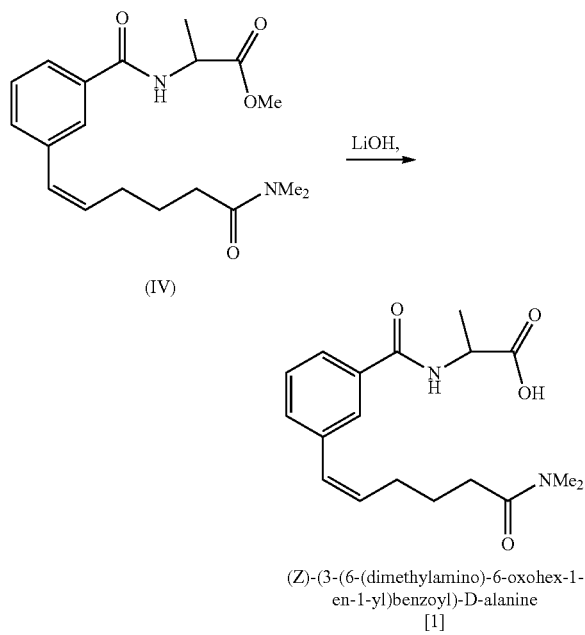

(Z)-(3-(6-(dimethylamino)-6-oxohex-1-en-1-yl)benzoyl)-D-alanine
[1]

The ester (IV) (135 mg, 0.41 mmol) in THF (2 mL) was added to lithium hydroxide, hydrate 84 mg, 2 mmol) in water (1 mL). The reaction was stirred at room temperature for 24 hrs. The THF was removed on the rotary evaporator and the residue taken up in 10% aq. Citric acid (10 mL). The aqueous mixture was extracted with DCM (3×30 mL) and dried over Na₂SO₄. Crude yield 307 mg. The product was purified by preparative LCMS (C18) using: Solvent A, 5% MeOH/95% H2O, 0.1% HCOOH. Solvent B, 95% MeOH/5% H₂O, 0.1% HCOOH. Gradient 10% A to 95% over 8 min. The fractions were combined, and the volatiles removed on a rotary evaporator. The final aqueous mixture was freeze dried.

1H NMR (500 MHz, CDCl3) δ 9.03 (s, 1H), 7.74 (s, 1H), 7.73-7.67 (m, J=7.7, 2H), 7.38-7.34 (m, 1H), 7.34-7.31 (m, 1H), 6.43 (d, J=11.6, 1H), 5.70 (dt, J=7.7, 11.6, 1H), 4.80-4.70 (m, 1H), 2.96 (s, 3H), 2.89 (s, 3H), 2.35 (t, J=7.1, 3H), 2.32-2.22 (m, 1H), 1.86-1.73 (m, 2H), 1.54 (d, J=7.2, 3H).

13C NMR (126 MHz, CDCl3) δ 175.39, 173.51, 168.12, 137.75, 133.65, 132.95, 132.31, 128.96, 128.62, 127.07, 126.06, 49.28, 37.55, 35.84, 32.64, 28.27, 25.08, 17.84.

Alternative Synthesis of Intermediate (IIb)

(i) Stage 1

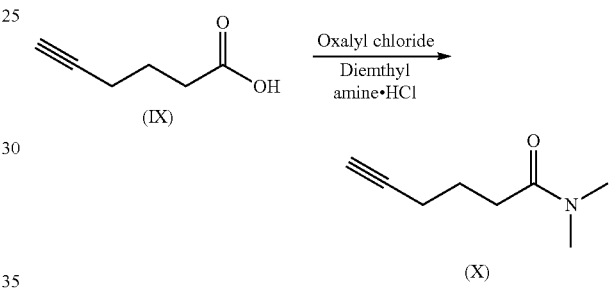

5-Hexynoic acid (553 g, 4.91 mol) and dichloromethane (5.5 L, 10 vol) are charged to a 10 L vessel and cooled to −7° C. Oxalyl chloride (0.475 L, 5.40 mol) is added dropwise maintaining the temperature between −4.5 and 5.0° C. over a 2 h period. The addition apparatus was washed with dichloromethane and stirred for 10 mins at −5° C. Dimethylformamide was added portion-wise with mild effervescence. The temperature was taken to 2° C. and the mixture stirred for 2 h and then warmed to 12° C. and stirred for a further 16 h until no further discernable reaction was observed. The mixture was concentrated to remove all oxalyl chloride. The vessel was rinsed with dichloromethane. Dimethylamine hydrochloride (490 g, 5.89 mol) and dichloromethane (5.5 L, 10 vol) were charged to the 10 L vessel. Triethylamine (2.5 L, 15.70 mol) was charged and the mixture cooled to −10° C. The concentrated acid chloride was treated with dichloromethane (0.3 L, 0.55 vol) and added dropwise maintaining temperature below 6° C. The addition apparatus was rinsed with dichloromethane (50 ml, 0.1 vol) the mixture was stirred at −5° C. for 15 mins and then allowed to warm to ambient temperature. When no further discernable reaction was observed. Water (3 L, 5.5 vol) was charged stirred and the layers partitioned. The aqueous was washed with dichloromethane (2.5 L, 4.5 vol). The organic layers were combined and then washed with 2M Hydrochloric acid (2.5l, 4.5 vol), 1M NaOH (2.5 L, 4.5 vol), water (3 L, 5.4 vol), brine (2.5 L, 4.5 vol) and dried over MgSO₄ (100 g, 20 wt %). The suspension was filtered and the solvent removed to give a dark oil (X) (214 g, 83%) GF1218-47-128 (568 g, 83%)

(ii) Stage 2

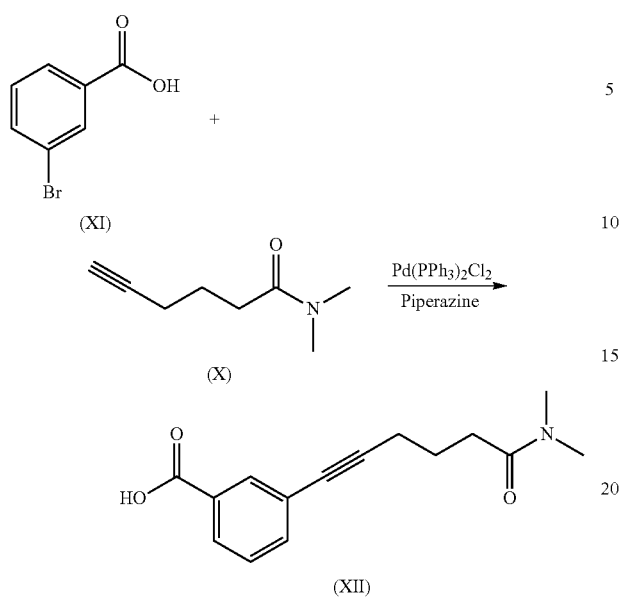

3-Bromobenzoic acid (XI) (631 g, 3.14 mol, 1.0 eq) and piperidine (1.55 L,) were charged to the vessel leading to a mild exotherm and the mixture was heated to 85° C. Dichlorobis(triphenylphosphine)Palladium (II) (44 g, 0.06 mol) was charged, followed by slow addition of N,N-dimethylhex-5-ynamide (X) (656 g, 4.71 mol) maintaining the temperature below 116° C. (reflux). The reaction was stirred for a further 1 hour until no further reaction was observed and allowed to cool to ambient temperature. The resulting viscous mixture was dissolved in water (9 L) an acidified with 5M HCl (4 L) and then extracted with ethyl acetate (5.5, 3.5 and 3 L). The organics were combined and washed with water (3 L) and brine (2 L) and then the solvent removed to give a dark oil. The material was taken in acetonitrile (2.5 L) and passed through silica(1.5 Kg) washing with acetonitrile (2.5 L). The resulting solution crystallised and the solid was collected (100 g). The liquors(≈4 L) were concentrated and crystallised to give the desired product as a solid (49 g). The silica was eluted with ethyl acetate (2 L), which yielded further product (54 g) after concentration. A further three portions of ethyl acetate (2 L) were used as eluent to give further product (40 g, 20 g and 17 g) respectively. The fractions were combined and treated with acetonitrile (340 ml) and recrystallised from the same solvent to give a pale yellow solid (XII) (105 g).

(iii) Stage 3

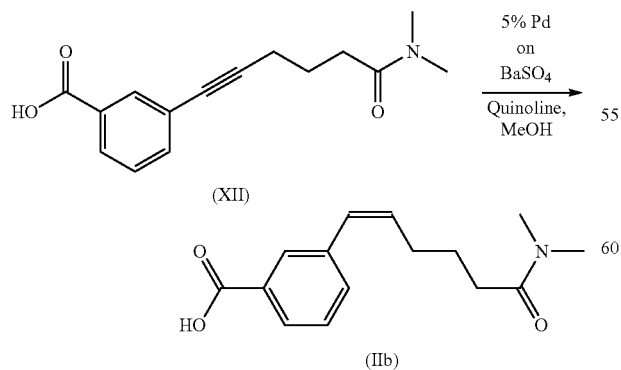

The alkyne (XII) (105 g, 0.4 mol, 1.0 eq) and 5% Pd on BaSO₄ (5.25 g, 5 wt %), methanol (25 vol) and quinoline (3.68 ml, 0.035 vol) were charged to the vessel The vessel was evacuated and the atmosphere replaced with hydrogen three times and then left to react at room temperature under a positive pressure of hydrogen until no further starting material was observable. The solution was degassed and the atmosphere replaced with nitrogen. The suspension was filtered through cellite and washed with methanol (1 L). The solution was then concentrated to dryness and taken in ethyl acetate (5 vol) and washed with 2M HCl (3×2 vol) and brine (3 vol).The solvent was removed and the resulting oil was taken up in acetone (3.3 vol) stirred and cooled until crystallisation occurred. The product was filtered and washed with cold acetone (0.5 vol) to give a colourless solid (IIb) (111 g, 61%).

Synthesis of VSN 45-47

(R)-methyl 2-(3-iodobenzamido)propanoate

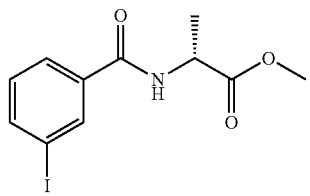 [SMILES: COC(=O)[C@@H](C)NC(=O)c1cccc(I)c1]

Using the general procedure described for amide coupling, the reaction of 3-iodobenzoic acid (22.3 g, 90 mmol), (R)-methyl 2-aminopropanoate.HCl (13.55 g, 97 mmol), HATU (37.6 g, 99 mmol) and TEA (31.3 ml, 225 mmol) in dry DCM (200 mL) gave the title compound (R)-methyl 2-(3-iodobenzamido)propanoate (41 g, 96% yield) as a pale yellow oil. No purification required.

($^1$H) DMSO-$d_6$: 1.40 (3H, d, J=7.3 Hz), 3.64 (3H, s), 4.47 (1H, qn, J=7.3 Hz), 7.30 (1H, t, J=7.8 Hz), 7.89 (1H, ddd, J=1.1, 1.6, 7.8 Hz), 7.93 (1H, ddd, J=1.0, 1.7, 7.8 Hz), 8.25 (1H, t, J=1.6 Hz), 8.92 (1H, d, J=6.8 Hz) ppm. MS(ES+) m/z 334.0 (M+H).

(R)-6-(3-((1-methoxy-1-oxopropan-2-yl)carbamoyl)phenyl)hex-5-ynoic acid

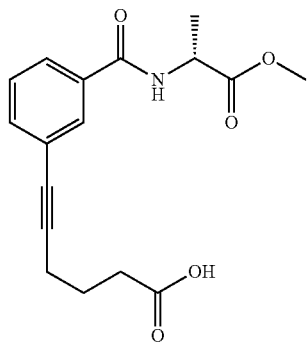 [SMILES: COC(=O)[C@@H](C)NC(=O)c1cccc(C#CCCCC(=O)O)c1]

Following the general method for Sonogashira coupling, the reaction of (R)-methyl 2-(3-iodobenzamido)propanoate (15.0 g, 36.0 mmol) and hex-5-ynoic acid (4.57 ml, 41.4 mmol) after purification by column chromatography (1-3% MeOH in DCM) gave (R)-6-(3-((1-methoxy-1-oxopropan-2-yl)carbamoyl)phenyl)hex-5-ynoic acid (8.43 g, 69.3% yield).

δ(¹H) DMSO-d₆: 1.40 (3H, d, J=7.3 Hz), 1.78 (2H, qn, J=7.2 Hz), 2.39 (2H, t, J=7.3 Hz), 2.46-2.49 (2H, m), 3.64 (3H, s), 4.47 (1H, qn, J=7.3 Hz), 7.46 (1H, t, J=7.8 Hz), 7.56 (1H, td, J=1.3, 7.7 Hz), 7.82 (1H, td, J=1.4, 7.8 Hz), 7.92 (1H, t, J=1.5 Hz), 8.87 (1H, d, J=6.9 Hz), 12.16 (1H, s) ppm.
MS(ES+) m/z 318 (M+H).

(R)-methyl 2-(3-(6-oxo-6-(pyrrolidin-1-yl)hex-1-yn-1-yl)benzamido)propanoate VSN 45

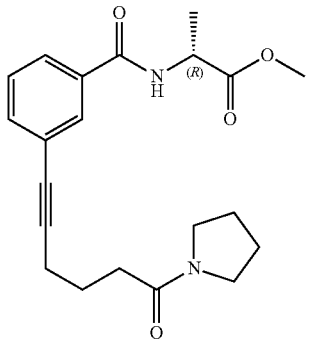

Using the general procedure described for amide coupling, the reaction of (R)-6-(3-((1-methoxy-1-oxopropan-2-yl)carbamoyl)phenyl)hex-5-ynoic acid (0.80 g, 2.52 mmol), pyrrolidine (0.22 ml, 2.65 mmol), DIPEA (1.35 ml, 7.56 mmol), HATU (1.15 g, 3.03 mmol) and dry DCM (10 mL) after purification by chromatography (1-4% MeOH in DCM) gave the title compound (R)-methyl 2-(3-(6-oxo-6-(pyrrolidin-1-yl)hex-1-yn-1-yl)benzamido)propanoate (0.6 g, 63.0% yield) as a pale yellow oil.

δ(¹H) DMSO-d₆: 1.40 (3H, d, J=7.3 Hz), 1.69-1.93 (6H, m), 2.39 (2H, t, J=7.2 Hz), 2.44-2.52 (2H, m), 3.28 (2H, t, J=6.8 Hz), 3.41 (2H, t, J=6.8 Hz), 3.64 (3H, s), 4.47 (1H, qn, J=7.3 Hz), 7.46 (1H, t, J=7.7 Hz), 7.56 (1H, td, J=1.3, 7.7 Hz), 7.82 (1H, td, J=1.5, 7.8 Hz), 7.92 (1H, t, J=1.5 Hz), 8.87 (1H, d, J=6.9 Hz) ppm.
δ(¹³C) DMSO-d₆: 16.65, 18.23, 32.56, 38.22, 45.21, 45.84, 48.28, 51.89, 80.20, 91.12, 123.20, 127.08, 128.74, 130.03, 133.91, 133.98, 165.41, 169.67, 173.05 ppm.
MS(ES+) m/z 371 (M+H).

(R,Z)-methyl 2-(3-(6-oxo-6-(pyrrolidin-1-yl)hex-1-en-1-yl)benzamido)propanoate VSN 46

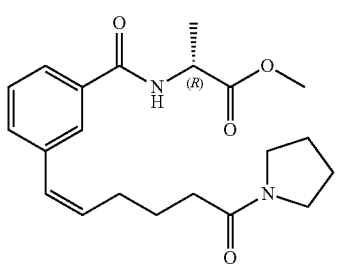

Following the general procedure for Lindlar reduction, the hydrogenation of (R)-methyl 2-(3-(6-oxo-6-(pyrrolidin-1-yl)hex-1-yn-1-yl)benzamido)propanoate (0.5 g, 1.350 mmol) gave the named product with trace amounts of the trans double bond isomer and fully saturated products (determined by ¹H NMR). Separation by column chromatography (1-3% MeOH in DCM) gave the title compound (0.17 g, 33.1%). The other 2 components were not isolated.

δ(¹H) DMSO-d₆: 1.40 (3H, d, J=7.3 Hz), 1.60-1.76 (4H, m), 1.82 (2H, qn, J=6.6 Hz), 2.25 (2H, t, J=7.2 Hz), 2.31 (2H, dq, J=1.6, 7.5 Hz), 3.22 (2H, t, J=6.9 Hz), 3.31-3.36 (2H, m), 3.64 (3H, s), 4.48 (1H, qn, J=7.3 Hz), 5.74 (1H, td, J=7.3, 11.7 Hz), 6.48 (1H, d, J=11.7 Hz), 7.42-7.49 (2H, m), 7.70-7.80 (2H, m), 8.81 (1H, d, J=6.9 Hz) ppm.
δ(¹³C) DMSO-d₆: 16.70, 23.89, 24.44, 25.55, 27.66, 33.03, 45.15, 45.79, 48.25, 51.86, 125.69, 127.47, 128.25, 128.36, 131.35, 133.30, 133.74, 137.11, 166.14, 169.98, 173.12 ppm.
MS(ES+) m/z 373 (M+H).

(R,Z)-2-(3-(6-oxo-6-(pyrrolidin-1-yl)hex-1-en-1-yl)benzamido)propanoic acid VSN 47

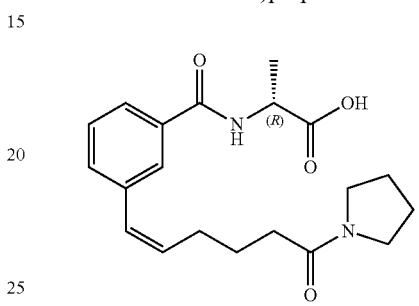

Following the general procedure for saponification, the reaction of (R,Z)-methyl 2-(3-(6-oxo-6-(pyrrolidin-1-yl)hex-1-en-1-yl)benzamido)propanoate (0.15 g, 0.40 mmol) with lithium hydroxide (19 mg, 0.81 mmol) gave (R,Z)-2-(3-(6-oxo-6-(pyrrolidin-1-yl)hex-1-en-1-yl)benzamido)propanoic acid (0.13 g, 88% yield) as a white solid.

δ(¹H) DMSO-d₆: 1.39 (3H, d, J=7.4 Hz), 1.68 (4H, m), 1.81 (2H, qn, J=6.6 Hz), 2.24 (2H, t, J=7.2 Hz), 2.27-2.37 (2H, m), 3.22 (2H, t, J=6.8 Hz), 3.32 (2H, t, J=6.8 Hz), 24.42 (1H, qn, J=7.3 Hz), 5.74 (1H, td, J=7.3, 11.7 Hz), 6.48 (1H, d, J=11.7 Hz), 7.41-7.50 (2H, m), 7.71-7.81 (2H, m), 8.71 (1H, d, J=7.3 Hz), 12.54 (1H, s) ppm.
δ(¹³C) DMSO-d₆: 16.88, 23.94, 24.49, 25.59, 27.70, 33.07, 45.20, 45.83, 48.17, 125.71, 127.52, 128.25, 128.43, 131.28, 133.30, 134.00, 137.10, 166.06, 170.02, 174.23 ppm.
MS(ES+) m/z 359 (M+H).
Synthesis of VSN 48-50

6-(3-(methoxycarbonyl)phenyl)hex-5-ynoic acid

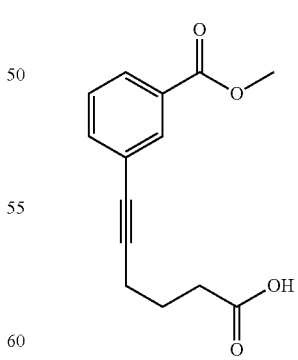

Following the general method for Sonogashira coupling, the reaction of methyl 3-iodobenzoate (1.0 g, 3.82 mmol) and hex-5-ynoic acid (0.421 ml, 3.82 mmol) after purification by column chromatography (0-3% MeOH in DCM) gave 6-(3-(methoxycarbonyl)phenyl)hex-5-ynoic acid (0.78 g, 81% yield).

δ($^1$H) DMSO-d$_6$: 1.79 (2H, qn, J=7.2 Hz), 2.39 (2H, t, J=7.3 Hz), 2.45-2.49 (2H, m), 3.86 (3H, s), 7.47-7.55 (1H, m), 7.66 (1H, td, J=1.4, 7.7 Hz), 7.88-7.94 (2H, m), 12.07 (1H, s) ppm.

MS(ES+) m/z 247 (M+H).

Methyl 3-(6-(dimethylamino)-6-oxohex-1-yn-1-yl)benzoate

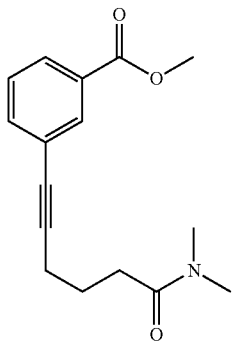 [SMILES: COC(=O)c1cccc(C#CCCCC(=O)N(C)C)c1]

Following the general procedure described for amide coupling, the reaction 6-(3-(methoxycarbonyl)phenyl)hex-5-ynoic acid (5.2 g, 21.12 mmol), dimethylamine.HCl (2.07 g, 25.3 mmol), DIPEA (11.28 ml, 63.3 mmol) and HATU (10.4 g, 27.5 mmol) in dry DCM (50 mL) gave methyl 3-(6-(dimethylamino)-6-oxohex-1-yn-1-yl)benzoate (5.3 g, 87% yield) as an orange oil. No purification required.

δ($^1$H) DMSO-d$_6$: 1.77 (2H, qn, J=7.2 Hz), 2.36-2.49 (4H, m), 2.82 (3H, s), 2.97 (3H, s), 3.86 (3H, s), 7.47-7.54 (1H, m), 7.66 (1H, td, J=1.4, 7.7 Hz), 7.89-7.91 (2H, m) ppm.

MS(ES+) m/z 274 (M+H).

3-(6-(dimethylamino)-6-oxohex-1-yn-1-yl)benzoic acid

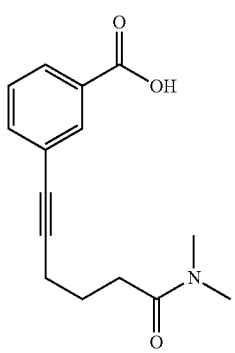 [SMILES: CN(C)C(=O)CCCC#Cc1cccc(C(=O)O)c1]

To a solution of methyl 3-(6-(dimethylamino)-6-oxohex-1-yn-1-yl)benzoate (5.30 g, 18.42 mmol) in THF (40 mL) and water (20 mL) was added lithium hydroxide (0.88 g, 36.8 mmol). The reaction was stirred at rt until judged complete by HPLC analysis. The volatiles were then removed in vacuo and the residue was partitioned between water (60 mL) and EtOAc (50 mL). The aqueous layer was then acidified to pH 1 with 1 N HCl (aq) and extracted with EtOAc (3×100 mL). Next, the combined organic extracts were washed with water (2×75 mL) and brine (50 mL) then dried (Na$_2$SO$_4$), filtered and concentrated in vacuo to a residue. This was azeotroped with iso-hexanes and dried in vacuum desiccator (45° C.) to give 3-(6-(dimethylamino)-6-oxohex-1-yn-1-yl)benzoic acid (4.3 g, 88% yield) as an orange solid.

δ($^1$H) DMSO-d$_6$: 1.78 (2H, qn, J=7.2 Hz), 2.41-2.49 (4H, m), 2.83 (3H, s), 2.98 (3H, s), 7.46-7.52 (1H, m), 7.64 (1H, td, J=1.5, 7.7 Hz), 7.87-7.91 (2H, m), 13.11 (1H, s) ppm.

MS(ES+) m/z 260 (M+H).

methyl 2-(3-(6-(dimethylamino)-6-oxohex-1-yn-1-yl)benzamido)acetate VSN 48

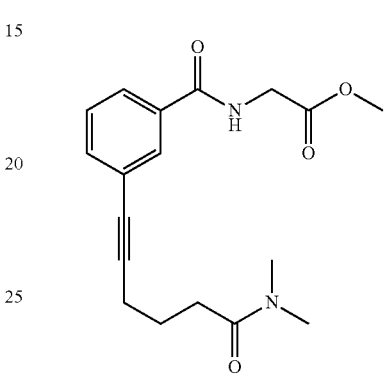

Using the general procedure described for amide coupling, the reaction of 3-(6-(dimethylamino)-6-oxohex-1-yn-1-yl)benzoic acid (0.70 g, 2.65 mmol), methyl 2-aminoacetate.HCl (0.38 g, 3.04 mmol), DIPEA (1.4 ml, 7.94 mmol) and HATU (1.31 g, 3.44 mmol) in dry DCM (10 mL) after purification by chromatography (1-3% MeOH in DCM) gave the title compound methyl 2-(3-(6-(dimethylamino)-6-oxohex-1-yn-1-yl)benzamido)acetate (0.86 g, 93% yield) as a pale yellow oil.

δ($^1$H) DMSO-d$_6$: 1.77 (2H, qn, J=7.2 Hz), 2.42-2.48 (4H, m), 2.82 (3H, s), 2.97 (3H, s), 3.65 (3H, s), 4.01 (2H, d, J=5.8 Hz), 7.47 (1H, t, J=7.8 Hz), 7.57 (1H, td, J=1.3, 7.7 Hz), 7.81 (1H, td, J=1.4, 7.8 Hz), 7.89 (1H, t, J=1.5 Hz), 9.04 (1H, t, J=5.8 Hz) ppm.

δ($^{13}$C) DMSO-d$_6$: 18.22, 23.92, 31.18, 34.77, 36.63, 38.22, 41.19, 51.75, 80.14, 91.18, 123.33, 126.85, 128.85, 129.92, 133.86 and 134.05, 165.81, 170.25, 171.30 ppm.

MS(ES+) m/z 331 (M+H).

(Z)-methyl 2-(3-(6-(dimethylamino)-6-oxohex-1-en-1-yl)benzamido)acetate VSN 49

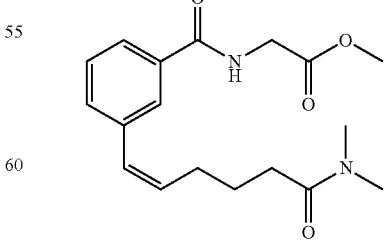

Following the general procedure for the Lindlar reduction, the hydrogenation of methyl 2-(3-(6-(dimethylamino)-6-oxohex-1-yn-1-yl)benzamido)acetate (0.40 g, 1.21 mmol)

gave the named product with trace amounts of the trans double bond isomer and fully saturated products (determined by $^1$H NMR). Separation by column chromatography (1-3% MeOH in DCM) gave the title compound (0.21 g, 51.1% yield). The other 2 components were not isolated.

δ($^1$H) DMSO-d$_6$: 1.65 (2H, qn, J=7.3 Hz), 2.27-2.36 (4H, m), 2.77 (3H, s), 2.92 (3H, s), 3.66 (3H, s), 4.02 (2H, d, J=5.9 Hz), 5.75 (1H, dt, J=7.4, 11.7 Hz), 6.47 (1H, br d, J=11.7 Hz), 7.47 (2H, dd, J=1.2, 4.0 Hz), 7.70-7.81 (2H, m), 8.98 (1H, t, J=5.8 Hz) ppm.

δ($^{13}$C) DMSO-d$_6$: 24.73, 27.73, 31.69, 34.74, 36.62, 41.23, 51.72, 125.53, 127.21, 128.29, 128.40, 131.50, 133.34, 133.65, 137.20, 166.50, 170.35, 171.65 ppm.

MS(ES+) m/z 333 (M+H).

(Z)-2-(3-(6-(dimethylamino)-6-oxohex-1-en-1-yl) benzamido)acetic acid VSN 50

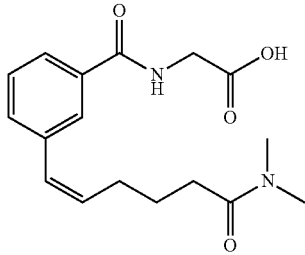 [SMILES: CN(C)C(=O)CCC/C=C\c1cccc(C(=O)NCC(=O)O)c1]

Following the general procedure for saponification, the reaction of (Z)-methyl 2-(3-(6-(dimethylamino)-6-oxohex-1-en-1-yl)benzamido)acetate (0.1 g, 0.30 mmol) with lithium hydroxide (14 mg, 0.60 mmol) gave (Z)-2-(3-(6-(dimethylamino)-6-oxohex-1-en-1-yl)benzamido)acetic acid (76 mg, 77% yield) as a colourless gum.

δ($^1$H) DMSO-d$_6$: 1.66 (2H, qn, J=7.3 Hz), 2.25-2.38 (4H, m), 2.78 (3H, s), 2.92 (3H, s), 3.94 (2H, d, J=5.9 Hz), 5.75 (1H, dt, J=7.4, 11.7 Hz), 6.48 (1H, d, J=11.8 Hz), 7.47 (2H, dd, J=1.5, 3.9 Hz), 7.71-7.77 (1H, m), 7.79 (1H, s), 8.87 (1H, t, J=5.8 Hz), 12.56 (1H, s) ppm.

δ($^{13}$C) DMSO-d$_6$: 24.74, 27.74, 31.71, 34.75, 36.63, 41.23, 125.52, 127.21, 128.33, 128.36, 131.39, 133.29, 133.88, 137.16, 166.37, 171.29, 171.66 ppm.

MS(ES+) m/z 319 (M+H).

Synthesis of VSN 51 to 53

(S)-methyl 2-(3-(6-(dimethylamino)-6-oxohex-1-yn-1-yl)benzamido)-3-hydroxypropanoate VSN 51

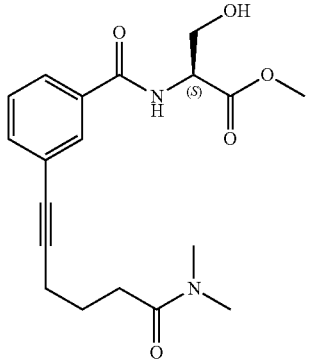

Using the general procedure described for amide coupling, the reaction of 3-(6-(dimethylamino)-6-oxohex-1-yn-1-yl)benzoic acid (0.70 g, 2.65 mmol), (S)-methyl 2-amino-3-hydroxypropanoate.HCl (0.45 g, 2.91 mmol), DIPEA (1.18 ml, 6.61 mmol) and HATU (1.16 g, 3.04 mmol) in dry DCM (10 mL) after purification by chromatography (1-5% MeOH in DCM) gave the title compound (S)-methyl 2-(3-(6-(dimethylamino)-6-oxohex-1-yn-1-yl)benzamido)-3-hydroxypropanoate (0.67 g, 68.9% yield) as a pale yellow oil.

δ($^1$H) DMSO-d$_6$: 1.78 (2H, qn, J=7.2 Hz), 2.42-2.49 (4H, m), 2.82 (3H, s), 2.97 (3H, s), 3.65 (3H, s), 3.79 (2H, t, J=5.9 Hz), 4.52 (1H, dt, J=5.5, 7.4 Hz), 5.04 (1H, t, J=6.2 Hz), 7.47 (1H, t, J=7.7 Hz), 7.57 (1H, td, J=1.3, 7.7 Hz), 7.83 (1H, td, J=1.5, 7.8 Hz), 7.93 (1H, t, J=1.5 Hz), 8.68 (1H, d, J=7.4 Hz) ppm.

δ($^{13}$C) DMSO-d$_6$: 18.23, 23.93, 31.20, 34.78, 36.63, 51.89, 55.71, 60.94, 80.18, 91.16, 123.21, 127.12, 128.76, 130.07, 133.98, 134.04, 165.73, 170.92, 171.30 ppm.

MS(ES+) m/z 361 (M+H).

(S,Z)-methyl 2-(3-(6-(dimethylamino)-6-oxohex-1-en-1-yl)benzamido)-3-hydroxypropanoate VSN 52

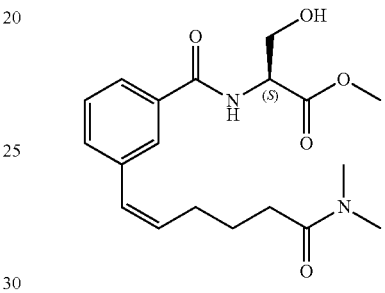

Following the general procedure for the Lindlar reduction, the hydrogenation of (S)-methyl 2-(3-(6-(dimethylamino)-6-oxohex-1-yn-1-yl)benzamido)-3-hydroxypropanoate (0.50 g, 1.39 mmol) gave the named product along with the trans double bond isomer (10%) and fully saturated product (20%) (determined by $^1$H NMR). Separation by column chromatography (1-3% MeOH in DCM) gave the title compound (0.28 g, 54.6% yield). The other 2 components were not isolated.

δ($^1$H) DMSO-d$_6$: 1.65 (2H, qn, J=7.4 Hz), 2.26-2.35 (4H, m), 2.77 (3H, s), 2.91 (3H, s), 3.65 (3H, s), 3.79 (2H, t, J=5.8 Hz), 4.54 (1H, dt, J=5.4, 7.4 Hz), 5.04 (1H, t, J=6.2 Hz), 5.75 (1H, dt, J=7.3, 11.7 Hz), 6.48 (1H, d, J=11.7 Hz), 7.44-7.50 (2H, m), 7.71-7.81 (2H, m), 8.60 (1H, d, J=7.4 Hz) ppm.

δ($^{13}$C) DMSO-d$_6$: 24.79, 27.71, 31.72, 34.74, 36.62, 51.86, 55.66, 60.99, 125.67, 127.57, 128.29, 128.33, 131.36, 133.33, 133.81, 137.15, 166.45, 171.03, 171.61 ppm.

MS(ES+) m/z 363 (M+H).

(S,Z)-2-(3-(6-(dimethylamino)-6-oxohex-1-en-1-yl) benzamido)-3-hydroxypropanoic acid VSN 53

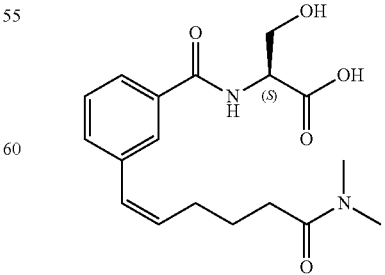

Following the general procedure for saponification, the reaction of (S,Z)-methyl 2-(3-(6-(dimethylamino)-6-oxohex-1-en-1-yl)benzamido)-3-hydroxypropanoate (0.15 g, 0.42 mmol) with lithium hydroxide (20 mg, 0.83 mmol) gave (S,Z)-2-(3-(6-(dimethylamino)-6-oxohex-1-en-1-yl)benzamido)-3-hydroxypropanoic acid (75 mg, 51.0% yield) as a colourless gum.

δ($^1$H) DMSO-d$_6$: 1.65 (2H, qn, J=7.4 Hz), 2.18-2.41 (4H, m), 2.77 (3H, s), 2.91 (3H, s), 3.80 (2H, d, J=5.2 Hz), 4.48 (1H, dt, J=7.7, 5.2 Hz), 4.95 (1H, br s), 5.75 (1H, dt, J=7.3, 11.7 Hz), 6.49 (1H, d, J=11.8 Hz), 7.47 (2H, d, J=5.0 Hz), 7.66-7.86 (2H, m), 8.42 (1H, d, J=7.7 Hz), 12.67 (1H, s) ppm.

δ($^{13}$C) DMSO-d$_6$: 24.80, 27.72, 31.73, 34.75, 36.63, 55.66, 61.16, 125.61, 127.53, 128.26, 128.37, 131.25, 133.29, 134.07, 137.13, 166.32, 171.62, 171.90 ppm.

MS(ES+) m/z 349 (M+H).

Synthesis of VSN 54 to 56

(S)-methyl 2-(3-(6-(dimethylamino)-6-oxohex-1-yn-1-yl)benzamido)-3-phenylpropanoate VSN 54

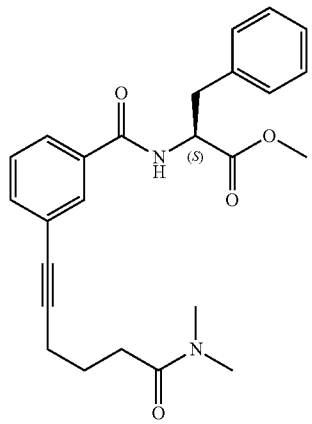

Using the general procedure described for amide coupling, the reaction of 3-(6-(dimethylamino)-6-oxohex-1-yn-1-yl)benzoic acid (0.70 g, 2.65 mmol), (S)-methyl 2-amino-3-phenylpropanoate.HCl (0.60 g, 2.78 mmol), DIPEA (1.18 ml, 6.61 mmol) and HATU (1.16 g, 3.04 mmol) in dry DCM (10 mL) after purification by chromatography (1-4% MeOH in DCM) gave the title compound (S)-methyl 2-(3-(6-(dimethylamino)-6-oxohex-1-yn-1-yl)benzamido)-3-phenylpropanoate (0.83 g, 72.4% yield) as a pale yellow oil.

δ($^1$H) DMSO-d$_6$: 1.71-1.84 (2H, m), 2.42-2.48 (4H, m), 2.82 (3H, s), 2.97 (3H, s), 3.08 (1H, dd, J=10.1, 13.8 Hz), 3.17 (1H, dd, J=5.3, 13.8 Hz), 3.64 (3H, s), 4.66 (1H, ddd, J=5.3, 7.8, 10.1 Hz), 7.16-7.23 (1H, m), 7.24-7.32 (4H, m), 7.43 (1H, t, J=7.7 Hz), 7.54 (1H, td, J=1.3, 7.7 Hz), 7.73 (1H, td, J=1.4, 7.8 Hz), 7.83 (1H, t, J=1.5 Hz), 8.93 (1H, d, J=7.8 Hz) ppm.

δ($^{13}$C) DMSO-d$_6$: 18.22, 23.91, 31.18, 34.78, 36.14, 36.62, 51.97, 54.25, 80.16, 91.17, 123.21, 126.48, 127.01, 128.23, 128.76, 129.00, 129.94, 133.87, 134.05, 137.64, 165.60, 171.30, 172.05 ppm.

MS(ES+) m/z 421 (M+H).

(S,Z)-methyl 2-(3-(6-(dimethylamino)-6-oxohex-1-en-1-yl)benzamido)-3-phenylpropanoate VSN 55

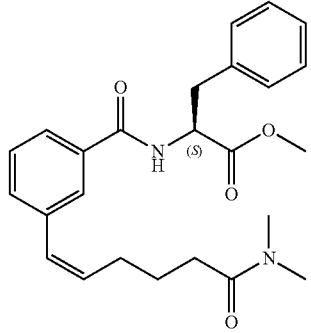

Following the general procedure for the Lindlar reduction, the hydrogenation of (S)-methyl 2-(3-(6-(dimethylamino)-6-oxohex-1-yn-1-yl)benzamido)-3-phenylpropanoate (0.5 g, 1.19 mmol) gave the named product along with the trans double bond isomer (5%) and fully saturated product (10%) (determined by $^1$H NMR). Separation by column chromatography (1-2% MeOH in DCM) gave the title compound (0.33 g, 64.4% yield). The other 2 components were not isolated.

δ($^1$H) DMSO-d$_6$: 1.64 (2H, qn, J=7.4 Hz), 2.23-2.36 (4H, m), 2.77 (3H, s), 2.90 (3H, s), 3.09 (1H, dd, J=10.3, 13.7 Hz), 3.17 (1H, dd, J=5.1, 13.7 Hz), 3.64 (3H, s), 4.66 (1H, ddd, J=5.2, 7.9, 10.2 Hz), 5.74 (1H, dt, J=7.3, 11.8 Hz), 6.45 (1H, br d, J=11.7 Hz), 7.13-7.23 (1H, m), 7.24-7.33 (4H, m), 7.40-7.47 (2H, m), 7.61-7.69 (2H, m), 8.87 (1H, d, J=7.9 Hz) ppm.

δ($^{13}$C) DMSO-d$_6$: 24.76, 27.68, 31.70, 34.73, 36.17, 36.60, 51.94, 54.27, 125.64, 126.46, 127.35, 128.21, 128.28, 129.05, 131.44, 133.33, 133.75, 137.09, 137.71, 166.40, 171.59, 172.15 ppm.

MS(ES+) m/z 423 (M+H).

(S,Z)-2-(3-(6-(dimethylamino)-6-oxohex-1-en-1-yl)benzamido)-3-phenylpropanoic acid VSN 56

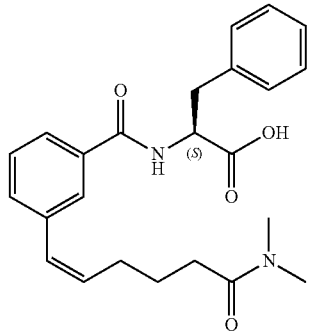

Following the general procedure for saponification, the reaction of (S,Z)-methyl 2-(3-(6-(dimethylamino)-6-oxohex-1-en-1-yl)benzamido)-3-phenylpropanoate (0.20 g, 0.47 mmol) with lithium hydroxide (23 mg, 0.95 mmol) gave (S,Z)-2-(3-(6-(dimethylamino)-6-oxohex-1-en-1-yl)benzamido)-3-phenylpropanoic acid (131 mg, 66.4% yield) as a colourless gum.

δ($^1$H) DMSO-d$_6$: 1.64 (2H, qn, J=7.4 Hz), 2.24-2.35 (4H, m), 2.77 (3H, s), 2.90 (3H, s), 3.06 (1H, dd, J=10.8, 13.7 Hz), 3.19 (1H, dd, J=4.3, 13.7 Hz), 5.73 (1H, td, J=7.3, 11.7 Hz), 6.45 (1H, d, J=11.8 Hz), 7.14-7.21 (2H, m), 7.24-7.28

(2H, m), 7.29-7.35 (2H, m), 7.42 (2H, d, J=5.3 Hz), 7.61-7.70 (2H, m), 8.72 (1H, d, J=8.2 Hz), 12.76 (1H, s) ppm.

δ($^{13}$C) DMSO-d$_6$: 24.78, 27.69, 31.71, 34.75, 36.21, 36.61, 54.20, 125.30, 126.32, 127.33, 128.15, 128.24, 128.31, 129.03, 131.31, 133.28, 134.01, 137.05, 138.19, 166.32, 171.60, 173.14 ppm.

MS(ES+) m/z 409 (M+H).

Synthesis of VSN 57 to 59

(R)-methyl 2-(3-(6-(dimethylamino)-6-oxohex-1-yn-1-yl)benzamido)-3-hydroxypropanoate VSN 57

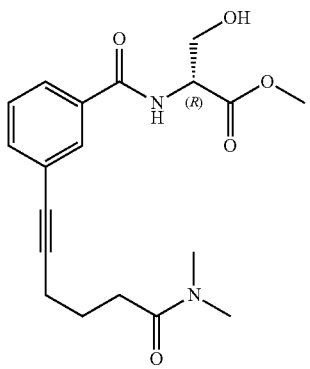

Using the general procedure described for amide coupling, the reaction of 3-(6-(dimethylamino)-6-oxohex-1-yn-1-yl)benzoic acid (0.70 g, 2.65 mmol), (R)-methyl 2-amino-3-hydroxypropanoate.HCl (0.45 g, 2.91 mmol), DIPEA (1.4 ml, 7.94 mmol) and HATU (1.21 g, 3.17 mmol) in dry DCM (10 mL) after purification by chromatography (1-5% MeOH in DCM) gave the title compound (R)-methyl 2-(3-(6-(dimethylamino)-6-oxohex-1-yn-1-yl)benzamido)-3-hydroxypropanoate (0.77 g, 79% yield) as a viscous pale yellow oil.

δ($^1$H) DMSO-d$_6$: 1.78 (2H, qn, J=7.2 Hz), 2.42-2.49 (4H, m), 2.82 (3H, s), 2.97 (3H, s), 3.65 (3H, s), 3.79 (2H, t, J=5.9 Hz), 4.52 (1H, dt, J=5.5, 7.4 Hz), 5.04 (1H, t, J=6.2 Hz), 7.47 (1H, t, J=7.7 Hz), 7.57 (1H, td, J=1.3, 7.7 Hz), 7.83 (1H, td, J=1.5, 7.8 Hz), 7.93 (1H, t, J=1.5 Hz), 8.68 (1H, d, J=7.4 Hz) ppm.

δ($^{13}$C) DMSO-d$_6$: 18.24, 23.93, 31.20, 34.78, 36.63, 51.88, 55.71, 60.94, 80.18, 91.16, 123.21, 127.12, 128.76, 130.07, 133.99, 134.04, 165.73, 170.92, 171.30 ppm.

MS(ES+) m/z 361 (M+H).

(R,Z)-methyl 2-(3-(6-(dimethylamino)-6-oxohex-1-en-1-yl)benzamido)-3-hydroxypropanoate VSN 58

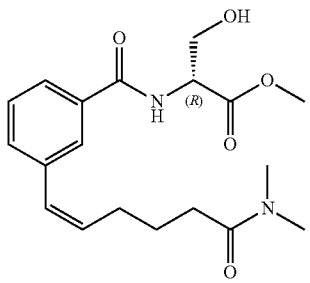

Following the general procedure for the Lindlar reduction, the hydrogenation of (R)-methyl 2-(3-(6-(dimethylamino)-6-oxohex-1-yn-1-yl)benzamido)-3-hydroxypropanoate (0.50 g, 1.39 mmol) gave the named product along with the trans double bond isomer (5%) and fully saturated product (5%) (determined by $^1$H NMR). Separation by column chromatography (1-3% MeOH in DCM) gave the title compound (0.32 g, 62.4% yield). The other 2 components were not isolated.

δ($^1$H) DMSO-d$_6$: 1.66 (2H, qn, J=7.4 Hz), 2.20-2.39 (4H, m), 2.78 (3H, s), 2.92 (3H, s), 3.66 (3H, s), 3.80 (2H, t, J=5.8 Hz), 4.54 (1H, dt, J=5.4, 7.4 Hz), 5.05 (1H, t, J=6.2 Hz), 5.76 (1H, dt, J=7.3, 11.7 Hz), 6.49 (1H, br d, J=11.7 Hz), 7.42-7.53 (2H, m), 7.71-7.82 (2H, m), 8.60 (1H, d, J=7.5 Hz) ppm.

δ($^{13}$C) DMSO-d$_6$: 24.78, 27.71, 31.72, 34.74, 36.62, 51.86, 55.66, 60.99, 125.66, 127.56, 128.28, 128.33, 131.36, 133.33, 133.81, 137.15, 166.44, 171.02, 171.61 ppm.

MS(ES+) m/z 363 (M+H).

(R,Z)-2-(3-(6-(dimethylamino)-6-oxohex-1-en-1-yl)benzamido)-3-hydroxypropanoic acid VSN 59

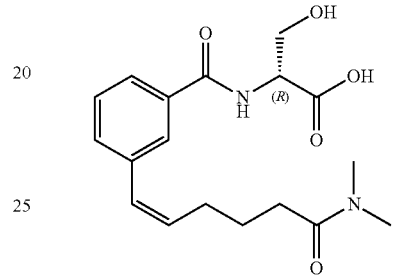

Following the general procedure for saponification, the reaction of (R,Z)-methyl 2-(3-(6-(dimethylamino)-6-oxohex-1-en-1-yl)benzamido)-3-hydroxypropanoate (0.15 g, 0.41 mmol) with lithium hydroxide (25 mg, 1.04 mmol) gave (R,Z)-2-(3-(6-(dimethylamino)-6-oxohex-1-en-1-yl)benzamido)-3-hydroxypropanoic acid (77 mg, 52.3% yield) as a colourless gum.

δ($^1$H) DMSO-d$_6$: 1.65 (2H, qn, J=7.4 Hz), 2.25-2.38 (4H, m), 2.77 (3H, s), 2.91 (3H, s), 3.79 (2H, d, J=5.2 Hz), 4.47 (1H, dt, J=5.2, 7.6 Hz), 5.60-5.89 (1H, m), 6.49 (1H, d, J=11.7 Hz), 7.34-7.59 (3H, m), 7.64-7.88 (2H, m), 8.41 (1H, d, J=7.7 Hz), 12.58 (1H, s) ppm.

δ($^{13}$C) DMSO-d$_6$: 24.79, 27.72, 31.73, 34.75, 36.63, 55.65, 61.16, 125.61, 127.53, 128.26, 128.37, 131.25, 133.29, 134.07, 137.13, 166.32, 171.61, 171.90 ppm.

MS(ES+) m/z 349 (M+H).

Synthesis of VSN 60 to 62

(R)-methyl 2-(3-(6-(dimethylamino)-6-oxohex-1-yn-1-yl)benzamido)-3-phenylpropanoate VSN 60

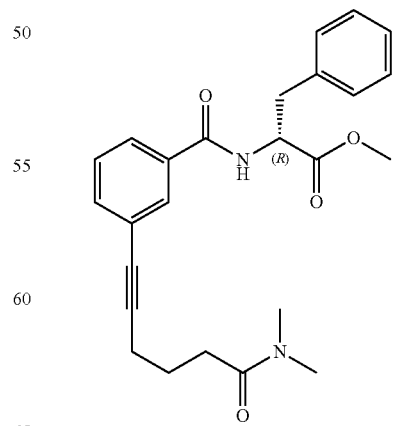

Using the general procedure described for amide coupling, the reaction of 3-(6-(dimethylamino)-6-oxohex-1-yn- 1-yl)benzoic acid (0.70 g, 2.65 mmol), (R)-methyl 2-amino-3-phenylpropanoate.HCl (0.6 g, 2.78 mmol), DIPEA (1.4 ml, 7.94 mmol) and HATU (1.3 g, 3.44 mmol) in dry DCM (10 mL) after purification by chromatography (1-4% MeOH in DCM) gave the title compound (R)-methyl 2-(3-(6-(dimethylamino)-6-oxohex-1-yn-1-yl)benzamido)-3-phenylpropanoate (0.81 g, 68.4% yield) as a viscous pale yellow oil.

δ($^1$H) DMSO-d$_6$: 1.74-1.82 (2H, m), 2.42-2.48 (4H, m), 2.82 (3H, s), 2.97 (3H, s), 3.08 (1H, dd, J=10.1, 13.8 Hz), 3.17 (1H, dd, J=5.3, 13.8 Hz), 3.64 (3H, s), 4.66 (1H, ddd, J=5.3, 7.8, 10.1 Hz), 7.16-7.23 (1H, m), 7.24-7.32 (4H, m), 7.43 (1H, t, J=7.7 Hz), 7.54 (1H, td, J=1.3, 7.7 Hz), 7.73 (1H, td, J=1.4, 7.8 Hz), 7.83 (1H, t, J=1.5 Hz), 8.93 (1H, d, J=7.8 Hz) ppm.

δ($^{13}$C) DMSO-d$_6$: 18.22, 23.91, 31.18, 34.78, 36.14, 36.62, 51.96, 54.25, 80.16, 91.17, 123.21, 126.48, 127.01, 128.22, 128.75, 129.00, 129.94, 133.87, 134.04, 137.63, 165.60, 171.29, 172.05 ppm.

MS(ES+) m/z 421 (M+H).

(R,Z)-methyl 2-(3-(6-(dimethylamino)-6-oxohex-1-en-1-yl)benzamido)-3-phenylpropanoate VSN 61

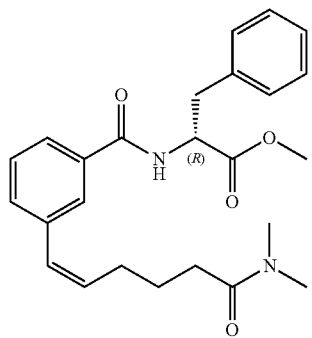

Following the general procedure for the Lindlar reduction, the hydrogenation of (R)-methyl 2-(3-(6-(dimethylamino)-6-oxohex-1-yn-1-yl)benzamido)-3-phenylpropanoate (0.50 g, 1.19 mmol) gave the named product along with the trans double bond isomer (5%) and fully saturated product (10%) (determined by $^1$H NMR). Separation by column chromatography (1-2% MeOH in DCM) gave the title compound (0.37 g, 72.2% yield). The other 2 components were not isolated.

δ($^1$H) DMSO-d$_6$: 1.65 (2H, qn, J=7.4 Hz), 2.25-2.38 (4H, m), 2.78 (3H, s), 2.91 (3H, s), 3.10 (1H, dd, J=10.3, 13.7 Hz), 3.18 (1H, dd, J=5.1, 13.7 Hz), 3.65 (3H, s), 4.67 (1H, ddd, J=5.2, 7.9, 10.2 Hz), 5.75 (1H, dt, J=7.4, 11.8 Hz), 6.46 (1H, br d, J=11.6 Hz), 7.15-7.24 (1H, m), 7.24-7.36 (4H, m), 7.44 (2H, d, J=5.0 Hz), 7.61-7.71 (2H, m), 8.87 (1H, d, J=8.0 Hz) ppm.

δ($^{13}$C) DMSO-d$_6$: 24.76, 27.68, 31.70, 34.73, 36.17, 36.60, 51.94, 54.27, 125.64, 126.46, 127.35, 128.21, 128.28, 129.04, 131.43, 133.33, 133.75, 137.09, 137.71, 166.40, 171.59, 172.15 ppm.

MS(ES+) m/z 423 (M+H).

(R,Z)-2-(3-(6-(dimethylamino)-6-oxohex-1-en-1-yl)benzamido)-3-phenylpropanoic acid VSN 62

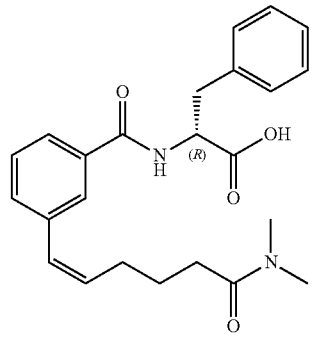

Following the general procedure for saponification, the reaction of (R,Z)-methyl 2-(3-(6-(dimethylamino)-6-oxohex-1-en-1-yl)benzamido)-3-phenylpropanoate (0.20 g, 0.47 mmol) with lithium hydroxide (23 mg, 0.95 mmol) gave (R,Z)-2-(3-(6-(dimethylamino)-6-oxohex-1-en-1-yl)benzamido)-3-phenylpropanoic acid (0.18 g, 0.43 mmol, 91% yield) as a colourless gum.

δ($^1$H) DMSO-d$_6$: 1.66 (2H, qn, J=7.4 Hz), 2.24-2.35 (4H, m), 2.77 (3H, s), 2.91 (3H, s), 3.08 (1H, dd, J=10.5, 13.8 Hz), 3.16-3.22 (1H, m), 4.64 (1H, td, J=4.5, 10.2 Hz), 5.74 (1H, dt, J=7.3, 11.7H), 6.45 (1H, d, J=11.7 Hz), 7.18 (1H, t, J=7.1 Hz), 7.22-7.34 (4H, m), 7.42 (2H, d, J=5.1 Hz), 7.59-7.71 (2H, m), 8.62 (1H, br d, J=4.4 Hz), 12.63 (1H, s) ppm.

δ($^{13}$C) DMSO-d$_6$: 24.78, 27.69, 31.71, 34.75, 36.21, 36.61, 54.21, 125.60, 126.32, 127.33, 128.15, 128.24, 128.32, 129.04, 131.31, 133.28, 134.01, 137.05, 138.20, 166.31, 171.60, 173.15 ppm.

MS(ES+) m/z 409 (M+H).

Synthesis of VSN 63 to 65

(S)-methyl 2-(3-(6-(dimethylamino)-6-oxohex-1-yn-1-yl)benzamido)propanoate VSN 63

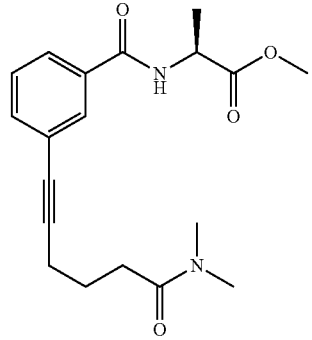 [SMILES: COC(=O)[C@H](C)NC(=O)c1cccc(C#CCCCC(=O)N(C)C)c1]

To a solution of 3-(6-(dimethylamino)-6-oxohex-1-yn-1-yl)benzoic acid (1.50 g, 4.63 mmol), (S)-methyl 2-aminopropanoate.HCl (0.78 g, 5.55 mmol) and HATU (2.3 g, 6.02 mmol) in dry DMF (15 mL) was added DIPEA (2.5 ml, 13.88 mmol). The reaciton was stirred at it until complete by LC-MS. Next, the reaction mixture was poured into water (150 mL) and extracted with EtOAc (4×100 mL) before the combined organic extracts were washed with sat. aq. ammonium chloride (100 mL), water (5×50 mL) then brine (50 mL) and dried (MgSO₄), filtered and concentrated in vacuo. The crude material was purified by chromatography (25-100% EtOAc in iso-hexanes) to give (S)-methyl 2-(3-(6-(dimethylamino)-6-oxohex-1-yn-1-yl)benzamido)propanoate (1.17 g, 68.3% yield at 90% purity). Material of sufficient purity to proceed. A sample (100 mg) was purified by preparative HPLC (20-50% MeCN in water (0.1% formic)) to give analytically pure material.

δ($^1$H) DMSO-$d_6$: 1.39 (3H, d, J=7.3 Hz), 1.77 (2H, qn, J=7.2 Hz), 2.43-2.48 (4H, m), 4.82 (3H, s), 2.97 (3H, s), 3.64 (3H, s), 4.47 (1H, qn, J=7.32 Hz), 7.46 (1H, t, J=7.7 Hz), 7.56 (1H, td, J=1.3, 7.7 Hz), 7.82 (1H, td, J=1.5, 7.8 Hz), 7.91-7.94 (1H, m), 8.89 (1H, d, J=6.9 Hz) ppm.

δ($^{13}$C) DMSO-$d_6$: 16.68, 18.24, 23.94, 31.21, 34.80, 36.64, 48.31, 51.93, 80.20, 91.15, 123.22, 127.13, 128.78, 130.05, 133.90, 134.03, 165.43, 171.31 ppm.

MS(ES+) m/z 345 (M+H).

(S)-methyl 2-(3-(6-(dimethylamino)-6-oxohexyl)benzamido)propanoate VSN 64

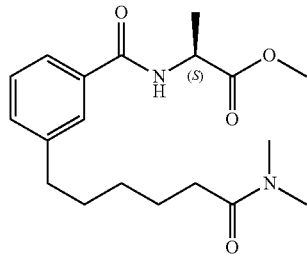

Following the general procedure for the reduction of an alkyne to alkane, the hydrogenation of (S)-methyl 2-(3-(6-(dimethylamino)-6-oxohex-1-yn-1-yl)benzamido)propanoate (0.37 g, 1.07 mmol) after purification by preparative HPLC (20-50% MeCN in water (0.1% formic)) gave the title compound (S)-methyl 2-(3-(6-(dimethylamino)-6-oxohexyl) benzamido)propanoate (228 mg, 59.7% yield) as a colourless viscous oil.

δ($^1$H) DMSO-$d_6$: 1.26-1.35 (2H, m), 1.40 (3H, t, J=7.4 Hz), 1.48-1.55 (2H, m), 1.56-1.64 (2H, m), 2.26 (2H, t, J=7.4 Hz), 2.60-2.64 (2H, m), 2.79 (3H, s), 2.93 (3H, s), 3.64 (3H, s), 4.47 (1H, qn, J=7.2 Hz), 7.35-7.39 (2H, m), 7.66-7.71 (2H, m), 8.74 (1H, d, J=7.0 Hz) ppm.

δ($^{13}$C) DMSO-$d_6$: 16.73, 24.48, 28.44, 30.82, 32.24, 34.73, 34.97, 36.67, 48.22, 51.85, 124.90, 127.26, 128.16, 131.42, 133.62, 142.41, 166.31, 171.84, 173.20 ppm.

MS(ES+) m/z 349 (M+H).

(S)-2-(3-(6-(dimethylamino)-6-oxohexyl)benzamido)propanoic acid VSN 65

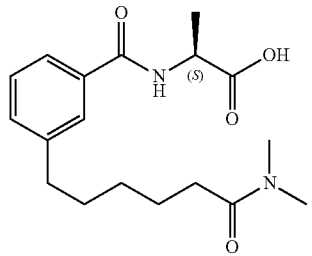

Following the general procedure for saponification, the reaction of (S)-methyl 2-(3-(6-(dimethylamino)-6-oxohexyl)benzamido)propanoate (0.10 g, 0.287 mmol) and lithium hydroxide (14 mg, 0.57 mmol) gave (S)-2-(3-(6-(dimethylamino)-6-oxohexyl) benzamido)propanoic acid (78 mg, 81% yield) as a white solid.

δ($^1$H) DMSO-$d_6$: 1.25-1.35 (2H, m), 1.39 (3H, d, J=7.4 Hz), 1.46-1.56 (2H, m), 1.56-1.65 (2H, m), 2.26 (2H, t, J=7.4 Hz), 2.62 (2H, t, J=7.7 Hz), 2.79 (3H, s), 2.93 (3H, s), 4.41 (1H, qn, J=7.3 Hz), 7.36 (2H, dd, J=1.2, 4.0 Hz), 7.63-7.76 (2H, m), 8.60 (1H, d, J=7.2 Hz), 12.50 (1H, s) ppm.

δ($^{13}$C) DMSO-$d_6$: 16.89, 24.48, 28.44, 30.83, 32.25, 34.74, 34.99, 36.67, 48.08, 124.88, 127.24, 128.11, 131.29, 133.89, 142.36, 166.20, 171.85, 174.23 ppm.

MS(ES+) m/z 335 (M+H).

Synthesis of VSN 66-68

N,N-dimethylpent-4-ynamide

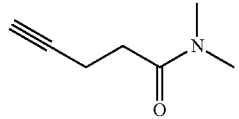

To a solution of pent-4-ynoic acid (3.1 g, 31.6 mmol) in dry DCM (30 mL) and DMF (1 drop) at 0° C. was added oxalyl chloride (4.01 ml, 47.4 mmol). The reaction was allowed to warm to it and stir for 1 h before the volatiles were removed in vacuo. The residue was redissolved in dry THF (10 mL) and added drop-wise to a cooled (ice bath) solution of dimethylamine (40 wt % in water) (20.0 ml, 158 mmol). The reaction was stirred in the ice bath for 1 h then extracted with DCM (3×30 mL). The combined organic extracts were washed with water (50 mL) and dried (MgSO₄), filtered then concentrated in vacuo to give N,N-dimethylpent-4-ynamide (3.3 g, 79% yield) as a brown free-flowing oil that solidified on standing.

δ($^1$H) DMSO-$d_6$: 2.31-1.35 (2H, m), 2.49-2.51 (2H, m), 2.74 (1H, t, J=2.6 Hz), 2.81 (3H, s), 2.94 (3H, s) ppm.

(R)-methyl 2-(3-(5-(dimethylamino)-5-oxopent-1-yn-1-yl)benzamido)propanoate VSN 66

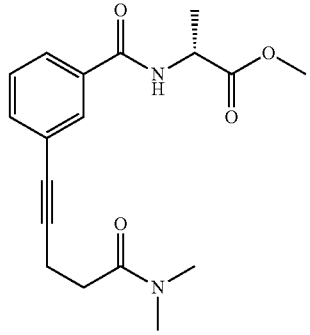 [SMILES: COC(=O)[C@@H](C)NC(=O)c1cccc(C#CCCC(=O)N(C)C)c1]

Following the general method for Sonogashira coupling, the reaction of (R)-methyl 2-(3-iodobenzamido)propanoate (2.0 g, 4.80 mmol) and N,N-dimethylpent-4-ynamide (0.73 g, 5.52 mmol) after purification by column chromatography (1-3% MeOH in DCM) gave (R)-methyl 2-(3-(5-(dimethylamino)-5-oxopent-1-yn-1-yl)benzamido)propanoate (1.4 g, 86% yield).

δ($^1$H) DMSO-$d_6$: 1.40 (3H, d, J=7.3 Hz), 2.64 (4H, br s), 2.82 (3H, s), 2.99 (3H, s), 3.65 (3H, s), 4.48 (1H, qn, J=7.2 Hz), 7.46 (1H, t, J=7.8 Hz), 7.55 (1H, td, J=1.4, 7.7 Hz), 7.83 (1H, td, J=1.6, 7.9 Hz), 7.92 (1H, t, J=1.4 Hz), 8.89 (1H, d, J=6.9 Hz) ppm.

δ($^{13}$C) DMSO-d$_6$: 14.77, 16.66, 31.59, 34.89, 36.53, 48.28, 51.89, 79.63, 91.22, 123.19, 127.09, 128.74, 130.03, 133.92, 133.95, 165.42, 170.16, 173.05 ppm.

MS(ES+) m/z 331 (M+H).

(R)-methyl 2-(3-(5-(dimethylamino)-5-oxopentyl)benzamido)propanoate VSN 67

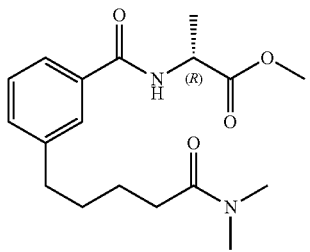

Following the general procedure for the reduction of an alkyne to alkane, the hydrogenation of (R)-methyl 2-(3-(5-(dimethylamino)-5-oxopent-1-yn-1-yl)benzamido)propanoate (400 mg, 1.211 mmol) after purification by chromatography (1-3% MeOH in DCM) gave the title compound (R)-methyl 2-(3-(5-(dimethylamino)-5-oxopentyl)benzamido)propanoate (0.36 g, 87% yield) as a colourless oil.

δ($^1$H) DMSO-d$_6$: 1.40 (3H, d, J=7.3 Hz), 1.45-1.56 (2H, m), 1.56-1.69 (2H, m), 2.30 (2H, t, J=7.3 Hz), 2.64 (2H, t, J=7.5 Hz), 2.79 (3H, s), 2.93 (3H, s), 3.64 (3H, s), 4.32-4.73 (1H, m), 7.37 (2H, dd, J=1.0, 4.1 Hz) 7.58-7.87 (2H, m), 8.74 (1H, d, J=6.9 Hz) ppm.

δ($^{13}$C) DMSO-d$_6$: 16.74, 24.26, 30.53, 32.11, 34.74, 34.85, 36.67, 48.23, 51.85, 124.90, 127.25, 128.16, 131.42, 133.63, 142.32, 166.32, 171.79, 173.20 ppm.

MS(ES+) m/z 335 (M+H).

(R)-2-(3-(5-(dimethylamino)-5-oxopentyl)benzamido)propanoic acid VSN 68

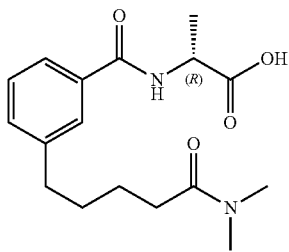

Following the general saponification procedure, the reaction of (R)-methyl 2-(3-(5-(dimethylamino)-5-oxopentyl)benzamido)propanoate (0.15 g, 0.45 mmol) with lithium hydroxide (16 mg, 0.67 mmol) gave (R)-2-(3-(5-(dimethylamino)-5-oxopentyl)benzamido)propanoic acid (82 mg, 55.9% yield) as a waxy white solid.

δ($^1$H) DMSO-d$_6$: 1.39 (3H, d, J=7.4 Hz), 1.46-1.54 (2H, m), 1.58-1.65 (2H, m), 2.30 (2H, t, J=7.3 Hz), 2.64 (2H, t, J=7.5 Hz), 2.79 (3H, s), 2.93 (3H, s), 4.41 (1H, qn, J=7.3 Hz), 7.34-7.39 (2H, m), 7.65-7.74 (2H, m), 8.61 (1H, d, J=7.2 Hz), 12.54 (1H, br s) ppm.

δ($^{13}$C) DMSO-d$_6$: 16.91, 24.27, 30.55, 32.12, 34.75, 34.86, 36.68, 48.10, 124.88, 127.22, 128.12, 131.29, 133.91, 142.26, 166.20, 171.80, 174.23 ppm.

MS(ES+) m/z 321 (M+H).

Synthesis of VSN 69 to 71

(R)-methyl 2-(3-(6-(dimethylamino)-6-oxohex-1-yn-1-yl)benzamido)propanoate VSN 69

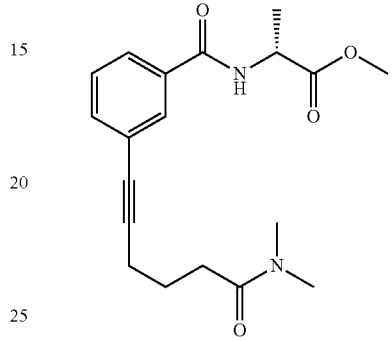

Using the general procedure described for amide coupling, the reaction of (R)-6-(3-((1-methoxy-1-oxopropan-2-yl)carbamoyl)phenyl)hex-5-ynoic acid (2.41 g, 5.70 mmol), dimethylamine.HCl (0.56 g, 6.84 mmol), HATU (2.60 g, 6.84 mmol) and TEA (1.99 ml, 14.24 mmol) in dry DCM (30 mL) after purification by chromatography (25-100% EtOAc in iso-hexanes) gave the title compound (R)-methyl 2-(3-(6-(dimethylamino)-6-oxohex-1-yn-1-yl)benzamido)propanoate (1.94 g, 89% yield) as a colourless oil. A sample (150 mg) was purified by preparative HPLC (20-50% MeCN in water (0.1% formic)) to give analytically pure material (128 mg).

δ($^1$H) DMSO-d$_6$: 1.40 (3H, d, J=7.3 Hz), 1.78 (2H, qn, J=7.1 Hz), 2.43-2.50 (4H, m), 2.83 (3H, s), 2.98 (3H, s), 3.65 (3H, s), 4.48 (1H, qn, J=7.3 Hz), 7.47 (1H, t, J=7.8 Hz), 7.57 (1H, td, J=1.3, 7.6 Hz), 7.83 (1H, td, J=1.4, 7.8 Hz), 7.93 (1H, t, J=1.5 Hz), 8.90 (1H, d, J=7.0 Hz) ppm.

δ($^{13}$C) DMSO-d$_6$: 16.69, 18.25, 23.95, 31.22, 34.81, 36.65, 48.31, 51.94, 91.16, 123.22, 127.13, 128.79, 130.06, 133.91, 134.05, 165.44, 171.32, 173.10 ppm.

MS(ES+) m/z 345 (M+H).

(R)-methyl 2-(3-(6-(dimethylamino)-6-oxohexyl)benzamido)propanoate VSN 70

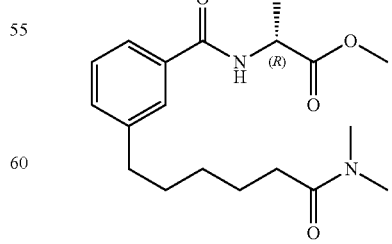

Following the general procedure for the reduction of an alkyne to alkane, the hydrogenation of (R)-methyl 2-(3-(6-(dimethylamino)-6-oxohex-1-yn-1-yl)benzamido)propanoate (250 mg, 0.73 mmol) after purification by preparative HPLC (20-50% MeCN in water (0.2% formic)) gave the title compound (R)-methyl 2-(3-(6-(dimethylamino)-6-oxohexyl) benzamido)propanoate (172 mg, 66.6% yield) as a colourless viscous oil.

δ($^1$H) DMSO-d$_6$: 1.21-1.36 (2H, m), 1.40 (3H, d, J=7.3 Hz), 1.51 (2H, qn, J=7.4 Hz), 1.60 (2H, qn, J=7.6 Hz), 2.26 (2H, t, J=7.4 Hz), 2.57-2.68 (2H, m), 2.79 (3H, s), 2.93 (3H, s), 3.64 (3H, s), 4.47 (1H, qn, J=7.3 Hz), 7.37 (2H, d, J=5.0 Hz), 7.65-7.73 (2H, m), 8.74 (1H, d, J=6.9 Hz) ppm.

δ($^{13}$C) DMSO-d$_6$: 16.73, 24.48, 28.44, 30.82, 32.24, 34.73, 34.98, 36.67, 48.22, 51.85, 124.90, 127.26, 128.16, 131.42, 133.62, 142.42, 166.31, 171.85, 173.20 ppm.

MS(ES+) m/z 349 (M+H).

(R)-2-(3-(6-(dimethylamino)-6-oxohexyl)benzamido)propanoic acid VSN 71

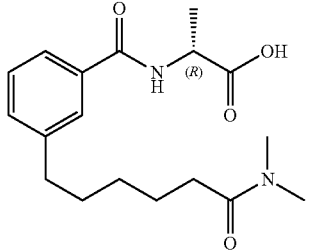

Following the general procedure for the reduction of an alkyne to alkane, the hydrogenation of (R)-2-(3-(6-(dimethylamino)-6-oxohex-1-yn-1-yl)benzamido)propanoic acid (146 mg, 0.44 mmol) gave the title compound (R)-2-(3-(6-(dimethylamino)-6-oxohexyl) benzamido)propanoic acid (0.14 g, 93% yield) as a colourless viscous oil. No purification required.

δ($^1$H) DMSO-d$_6$: 1.26-1.36 (2H, m), 1.40 (3H, d, J=7.4 Hz), 1.48-1.57 (2H, m), 1.57-1.66 (2H, m), 2.27 (2H, t, J=7.4 Hz), 2.59-2.67 (2H, m), 2.79 (3H, s), 2.94 (3H, s), 4.41 (1H, qn, J=7.4 Hz), 7.32-7.42 (2H, m), 7.65-7.76 (2H, m), 8.60 (1H, d, J=7.2 Hz), 12.51 (1H, s) ppm.

δ($^{13}$C) DMSO-d$_6$: 16.93, 24.53, 28.49, 30.90, 32.28, 34.77, 35.04, 36.70, 48.14, 54.95, 124.92, 127.28, 128.16, 131.35, 133.90, 142.40, 166.23, 171.89, 174.31 ppm.

MS(ES+) m/z 335 (M+H).

Synthesis of VSN 72 to 74 oct-7-ynoic acid

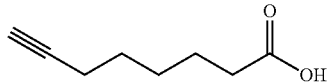

To a solution of 6-bromohexanoic acid (2.4 g, 12.30 mmol) in dry DMSO (20 mL) under nitrogen was was added lithium acetylide ethylenediamine complex (2.49 g, 27.1 mmol) protion-wise over 15 min. Upon complete addition, the resulting brown solution was stirred at it for 2 h. The reaction was then quenched by the addition of water (20 mL) and acidified to pH 1 with 1 N HCl. The product was then extracted with EtOAc (4×60 mL) before the combined organic extracts were washed with water (5×80 mL) and brine (60 mL) then dried (MgSO4), filtered and concentrated in vacuo to give oct-7-ynoic acid (0.7 g, 36.5% yield) as a pale orange oil.

δ($^1$H) DMSO-d$_6$: 1.30-1.38 (2H, m), 1.39-1.46 (2H, m), 1.39-1.54 (2H, m), 2.14 (2H, dt, J=2.7, 7.0 Hz), 2.20 (2H, t, J=7.4 Hz), 2.75 (1H, t, J=2.7 Hz), 11.98 (1H, s) ppm.

(R)-8-(3-((1-methoxy-1-oxopropan-2-yl)carbamoyl) phenyl)oct-7-ynoic acid

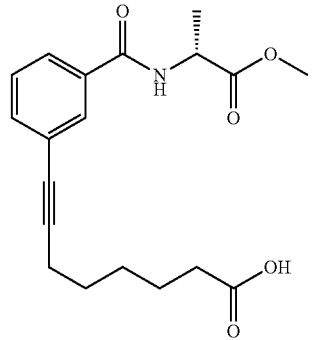 [SMILES: COC(=O)[C@@H](C)NC(=O)c1cccc(C#CCCCCCC(=O)O)c1]

Following the general method for Sonogashira coupling, the reaction of (R)-methyl 2-(3-iodobenzamido)propanoate (1.8 g, 4.34 mmol) and oct-7-ynoic acid (0.7 g, 4.99 mmol) after purification by column chromatography (1-3% MeOH in DCM) gave (R)-8-(3-((1-methoxy-1-oxopropan-2-yl)carbamoyl)phenyl)oct-7-ynoic acid (1.3 g, 69.3% yield @ 80% purity).

δ($^1$H) DMSO-d$_6$: 1.35-1.49 (5H, m), 1.50-1.63 (4H, m), 2.23 (2H, t, J=7.2 Hz), 2.44 (2H, t, J=7.0 Hz), 3.64 (3H, s), 4.47 (1H, qn, J=7.3, 1.8 Hz), 7.44-7.50 (1H, m), 7.55 (1H, td, J=1.4, 7.7 Hz), 7.82 (1H, dt, J=1.5, 7.8 Hz), 7.86-7.95 (1H, m), 8.83-8.90 (1H, m), 12.00 (1H, s) ppm.

MS(ES+) m/z 346 (M+H).

(R)-methyl 2-(3-(8-(dimethylamino)-8-oxooct-1-yn-1-yl)benzamido)propanoate VSN 72

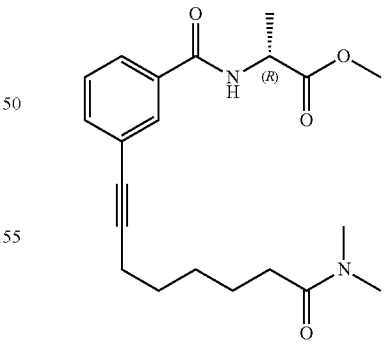

Using the general procedure described for amide coupling, the reaction of (R)-8-(3-((1-methoxy-1-oxopropan-2-yl)carbamoyl)phenyl)oct-7-ynoic acid (1.3 g, 3.01 mmol), dimethylamine.HCl (0.27 g, 3.31 mmol), DIPEA (1.32 ml, 7.53 mmol) and HATU (1.32 g, 3.46 mmol) in dry DCM (15 mL) after purification by chromatography (1-3% MeOH in DCM) gave the title compound (R)-methyl 2-(3-(8-(dimethylamino)-8-oxooct-1-yn-1-yl)benzamido)propanoate (1.0 g, 85% yield) as a viscous yellow oil.

δ($^1$H) DMSO-$d_6$: 1.39 (3H, d, J=7.3 Hz), 1.42-1.47 (2H, m), 1.48-1.61 (4H, m), 2.30 (2H, t, J=7.5 Hz), 2.44 (2H, t, J=7.0 Hz), 2.79 (3H, s), 2.95 (3H, s), 3.64 (3H, s), 4.47 (1H, qn, J=7.2 Hz), 7.45 (1H, t, J=7.8 Hz), 7.55 (1H, td, J=1.4, 7.8 Hz), 7.81 (1H, td, J=1.6, 7.9 Hz), 7.91 (1H, t, J=1.5 Hz), 8.87 (1H, d, J=6.9 Hz) ppm.

δ($^{13}$C) DMSO-$d_6$: 16.70, 18.52, 24.18, 27.95, 28.13, 32.19, 34.73, 36.67, 48.27, 51.87, 79.93, 91.45, 123.29, 127.02, 128.71, 129.96, 133.89, 133.97, 165.41, 171.81, 173.04 ppm.

MS(ES+) m/z 373 (M+H).

(R)-methyl 2-(3-(8-(dimethylamino)-8-oxooctyl)benzamido)propanoate VSN 73

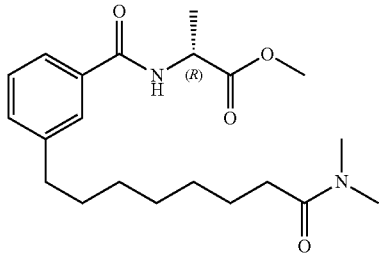

Following the general procedure for the reduction of an alkyne to alkane, the hydrogenation of (R)-methyl 2-(3-(8-(dimethylamino)-8-oxooct-1-yn-1-yl)benzamido)propanoate (400 mg, 1.07 mmol) after purification by chromatography (1-5% MeOH in DCM) gave the title compound (R)-methyl 2-(3-(8-(dimethylamino)-8-oxooctyl)benzamido)propanoate (0.34 g, 80% yield) as a colourless oil.

δ($^1$H) DMSO-$d_6$: 1.24-1.29 (6H, m), 1.40 (3H, d, J=7.32 Hz), 1.46 (2H, qn, J=6.9 Hz), 1.55-1.62 (2H, m), 2.24 (2H, t, J=7.5 Hz), 2.60-2.64 (2H, m), 2.79 (3H, s), 2.93 (3H, s), 3.64 (3H, s), 4.47 (1H, qn, J=7.2 Hz), 7.35-7.39 (2H, m), 7.66-7.72 (2H, m), 8.74 (1H, d, J=7.0 Hz) ppm.

δ($^{13}$C) DMSO-$d_6$: 6.73, 24.62, 28.58, 28.69, 28.73, 30.89, 32.28, 34.72, 35.02, 36.67, 48.22, 51.84, 124.87, 127.23, 128.14, 131.39, 133.62, 142.48, 166.31, 171.89, 173.20 ppm.

MS(ES+) m/z 377 (M+H).

(R)-2-(3-(8-(dimethylamino)-8-oxooctyl)benzamido)propanoic acid VSN 74

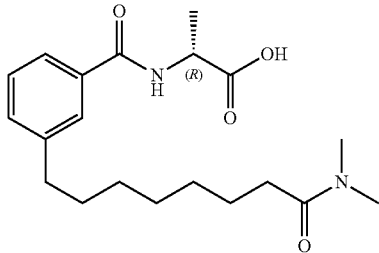

Following the general procedure for saponification, the reaction of (R)-methyl 2-(3-(8-(dimethylamino)-8-oxooctyl)benzamido)propanoate (0.15 g, 0.40 mmol) with lithium hydroxide (14 mg, 0.60 mmol) gave (R)-2-(3-(8-(dimethylamino)-8-oxooctyl)benzamido)propanoic acid (0.11 g, 74.6% yield).

δ($^1$H) DMSO-$d_6$: 1.22-1.34 (6H, m), 1.40 (3H, d, J=7.4 Hz), 1.47 (2H, qn, J=7.4 Hz), 1.56-1.63 (2H, m), 2.25 (2H, t, J=7.4 Hz), 2.61-2.65 (2H, m), 2.79 (3H, s), 2.94 (3H, s), 4.42 (1H, qn, J=7.3 Hz), 7.35-7.39 (2H, m), 7.68-7.72 (2H, m) 8.61 (1H, d, J=7.3 Hz), 12.52 (1H, s) ppm.

δ($^{13}$C) DMSO-$d_6$: 6.89, 24.63, 28.60, 28.70, 28.74, 30.91, 32.29, 34.73, 35.04, 36.68, 48.08, 124.86, 127.21, 128.10, 131.26, 133.89, 142.42, 166.21, 171.90, 174.24 ppm.

MS(ES+) m/z 363 (M+H).

Synthesis of VSN 75 to 77 methyl 3-(3-(6-(dimethylamino)-6-oxohex-1-yn-1-yl)benzamido)propanoate VSN 75

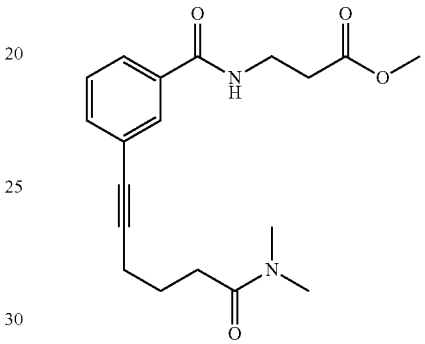

Using the general procedure described for amide coupling, the reaction of 3-(6-(dimethylamino)-6-oxohex-1-yn-1-yl)benzoic acid (0.75 g, 2.314 mmol), methyl 3-aminopropanoate.HCl (0.36 g, 2.55 mmol), DIPEA (1.24 ml, 6.94 mmol) and HATU (1.14 g, 3.01 mmol) in dry DCM (15 mL) after purification by chromatography (1-3% MeOH in DCM) gave the title compound methyl 3-(3-(6-(dimethylamino)-6-oxohex-1-yn-1-yl)benzamido)propanoate (0.66 g, 79% yield) as a viscous pale yellow oil.

δ($^1$H) DMSO-$d_6$: 1.78 (2H, qn, J=7.2 Hz), 2.41-2.48 (4H, m), 2.59 (2H, t, J=7.0 Hz), 2.82 (3H, s), 2.97 (3H, s), 3.43-3.52 (2H, m), 3.60 (3H, s), 7.44 (1H, t, J=7.8 Hz), 7.53 (1H, td, J=1.3, 7.7 Hz), 7.77 (1H, td, J=1.4, 7.8 Hz), 7.84 (1H, t, J=1.5 Hz), 8.61 (1H, t, J=5.4 Hz) ppm.

δ($^{13}$C) DMSO-$d_6$: 18.22, 23.93, 31.19, 33.41, 34.77, 35.51, 36.62, 51.38, 80.23, 91.04, 123.17, 126.81, 128.70, 129.77, 133.72, 134.55, 165.45, 171.29, 171.70 ppm.

MS(ES+) m/z 345 (M+H).

(Z)-methyl 3-(3-(6-(dimethylamino)-6-oxohex-1-en-1-yl)benzamido)propanoate VSN 76

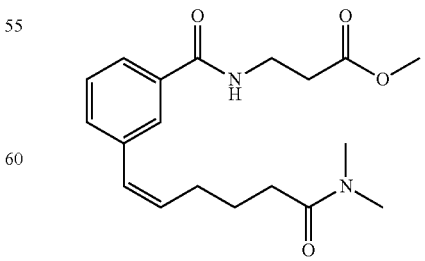

Following the general procedure for the Lindlar reduction, the hydrogenation of methyl 3-(3-(6-(dimethylamino)-6-oxohex-1-yn-1-yl)benzamido)propanoate (0.40 g, 1.16 mmol) gave the named product along with the trans double bond isomer (7%) and fully saturated product (25%) (determined by $^1$H NMR). Separation by column chromatography (1-3% MeOH in DCM) gave the title compound (0.20 g, 48.7% yield). The other 2 components were not isolated.

δ($^1$H) DMSO-d$_6$: 1.64 (2H, qn, J=7.4 Hz), 2.25-2.34 (4H, m), 2.60 (2H, t, J=7.0 Hz), 2.78 (3H, s), 2.92 (3H, s), 3.45-3.54 (2H, m), 3.60 (3H, s), 5.73 (1H, td, J=7.3, 11.7 Hz), 6.46 (1H, br d, J=11.7 Hz), 7.43 (2H, dd, J=1.3, 3.9 Hz), 7.64-7.75 (2H, m), 8.57 (1H, t, J=5.4 Hz) ppm.

δ($^{13}$C) DMSO-d$_6$: 24.75, 27.72, 31.71, 33.54, 34.74, 35.51, 36.61, 51.36, 125.42, 127.16, 128.25, 128.36, 131.11, 133.22, 134.39, 137.08, 166.22, 171.63, 171.73 ppm.

MS(ES+) m/z 347 (M+H).

(Z)-3-(3-(6-(dimethylamino)-6-oxohex-1-en-1-yl)benzamido)propanoic acid VSN 77

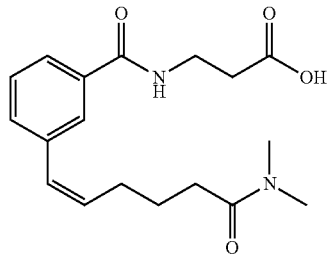 [SMILES: CN(C)C(=O)CCC/C=C\c1cccc(C(=O)NCCC(=O)O)c1]

Following the general procedure for saponification, the reaction of (Z)-methyl 3-(3-(6-(dimethylamino)-6-oxohex-1-en-1-yl)benzamido)propanoate (0.1 g, 0.29 mmol) with lithium hydroxide (14 mg, 0.58 mmol) gave (Z)-3-(3-(6-(dimethylamino)-6-oxohex-1-en-1-yl)benzamido)propanoic acid (86 mg, 88% yield) as a colourless gum.

δ($^1$H) DMSO-d$_6$: 1.64 (2H, qn, J=7.4 Hz), 2.27-2.32 (4H, m), 2.50-2.55 (2H, m), 2.78 (3H, s), 2.92 (3H, s), 3.46 (2H, q, J=7.1 Hz), 5.73 (1H, dt, J=7.3, 11.7 Hz), 6.46 (1H, d, J=11.7 Hz), 7.43 (2H, dd, J=3.9, 1.4 Hz), 7.67-7.71 (1H, m), 7.72 (1H, br s), 8.55 (1H, t, J=5.5 Hz), 12.20 (1H, s) ppm.

δ($^{13}$C) DMSO-d$_6$: 24.76, 27.73, 31.72, 33.76, 34.75, 35.59, 36.63, 125.41, 127.18, 128.24, 128.38, 131.07, 133.21, 134.45, 137.08, 166.14, 171.66, 172.86 ppm.

MS(ES+) m/z 333 (M+H).

Synthesis of VSN 78 to 80

(R)-methyl 2-(3-(5-cyanopent-1-yn-1-yl)benzamido)propanoate VSN 78

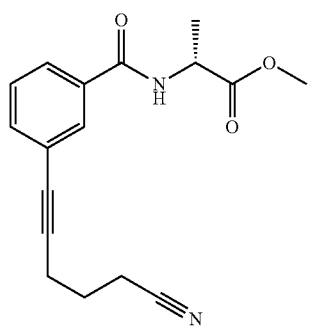 [SMILES: COC(=O)[C@@H](C)NC(=O)c1cccc(C#CCCCC#N)c1]

Following the general method for Sonogashira coupling, the reaction of (R)-methyl 2-(3-iodobenzamido)propanoate (1.6 g, 4.56 mmol) and hex-5-ynenitrile (0.72 ml, 6.84 mmol) after purification by chromatography (20-40% EtOAc in iso-hexanes) gave (R)-methyl 2-(3-(5-cyanopent-1-yn-1-yl)benzamido)propanoate (1.3 g, 93% yield).

δ($^1$H) DMSO-d$_6$: 1.39 (3H, d, J=7.3 Hz), 1.86 (2H, qn, J=7.1 Hz), 2.57 (2H, t, J=7.0 Hz), 2.65 (2H, t, J=7.2 Hz), 3.64 (3H, s), 4.47 (1H, qn, J=7.2 Hz), 7.47 (1H, t, J=7.8 Hz), 7.58-7.60 (1H, m), 7.82-7.85 (1H, m), 7.94 (1H, t, J=1.4 Hz), 8.87 (1H, d, J=6.9 Hz) ppm.

δ($^{13}$C) DMSO-d$_6$: 15.58, 16.66, 17.86, 24.06, 48.29, 51.90, 80.88, 89.35, 120.18, 122.90, 127.27, 128.73, 130.11, 133.93, 134.10, 165.40, 173.05 ppm.

MS(ES+) m/z 299.2 (M+H).

(R,Z)-methyl 2-(3-(5-cyanopent-1-en-1-yl)benzamido)propanoate VSN 79

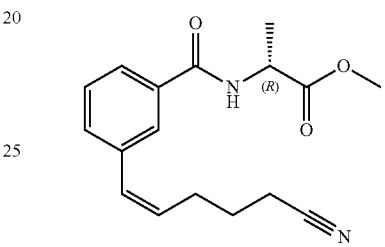

Following the general procedure for the Lindlar reduction, the hydrogenation of (R)-methyl 2-(3-(5-cyanopent-1-yn-1-yl)benzamido)propanoate (0.50 g, 1.68 mmol) gave the named product with trace amounts of the trans double bond isomer and fully saturated products (determined by $^1$H NMR). Separation by column chromatography (1-2% MeOH in DCM) gave the title compound (0.42 g, 82% yield). The other 2 components were not isolated.

δ($^1$H) DMSO-d$_6$: 1.41 (3H, d, J=7.3 Hz), 1.73 (2H, qn, J=7.3 Hz), 2.40 (2H, dq, J=1.8, 7.1 Hz), 2.53-2.55 (2H, m), 3.65 (3H, s), 4.49 (1H, qn, J=7.2 Hz), 5.74 (1H, td, J=7.2, 11.6 Hz), 6.53 (1H, dt, J=1.6, 11.7 Hz), 7.47-7.49 (2H, m), 7.76-7.78 (2H, m), 8.81 (1H, d, J=6.9 Hz) ppm.

δ($^{13}$C) DMSO-d$_6$: 15.80, 16.72, 24.97, 27.10, 48.26, 51.87, 120.45, 125.83, 127.65, 128.30, 129.14, 131.28, 131.61, 133.81, 136.85, 166.13, 173.14 ppm.

MS(ES+) m/z 301.2 (M+H).

(R,Z)-2-(3-(5-cyanopent-1-en-1-yl)benzamido)propanoic acid VSN 80

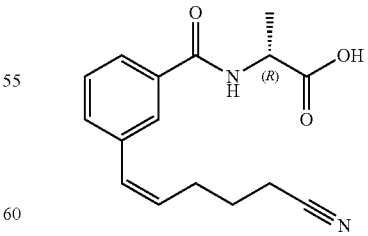

Following the general procedure for saponification, the reaction of (R,Z)-methyl 2-(3-(5-cyanopent-1-en-1-yl)benzamido)propanoate (0.15 g, 0.50 mmol) with lithium hydroxide (24 mg, 0.99 mmol) gave (R,Z)-2-(3-(5-cyanopent-1-en-1-yl)benzamido)propanoic acid (0.12 g, 80% yield).

δ(¹H) DMSO-d₆: 1.39 (3H, d, J=7.4 Hz), 1.72 (2H, qn, J=7.6 Hz), 2.39 (2H, dq, J=1.7, 7.3 Hz), 2.52-2.54 (2H, m), 4.41 (1H, qn, 7.3 Hz), 5.73 (1H, td, J=7.1, 11.7 Hz), 6.53 (1H, br d, J=11.7 Hz), 7.46-7.47 (2H, m), 7.76-7.77 (2H, m), 8.67 (1H, d, J=7.2 Hz), 12.53 (1H, br s) ppm.

δ(¹³C) DMSO-d₆: 15.80, 16.87, 24.98, 27.11, 48.14, 120.46, 125.81, 127.65, 128.26, 129.19, 131.16, 131.57, 134.08, 136.81, 166.02, 174.19 ppm.

MS(ES+) m/z 287.2 (M+H).

Synthesis of VSN 81, 85 and 86 methyl 3-(5-hydroxypent-1-yn-1-yl)benzoate

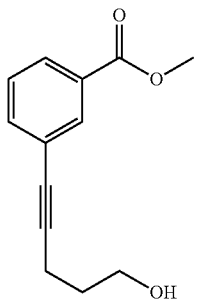 [SMILES: COC(=O)c1cccc(C#CCCCO)c1]

Following the general method for Sonogashira coupling, the reaction of methyl 3-iodobenzoate (7.45 g, 28.4 mmol) and pent-4-yn-1-ol (3.97 ml, 42.6 mmol) after purification by chromatography (10-50% EtOAc in iso-hexanes) gave methyl 3-(5-hydroxypent-1-yn-1-yl)benzoate (5.1 g, 81% yield) as a free flowing orange oil.

δ(¹H) DMSO-d₅: 1.63-1.75 (2H, m), 2.45-2.49 (2H, m), 3.46-3.57 (2H, m), 3.86 (3H, s), 4.55 (1H, t, J=5.2 Hz), 7.47-7.56 (1H, m), 7.65 (1H, td, J=1.4, 7.7 Hz), 7.86-7.93 (2H, m) ppm.

MS(ES+) m/z 219 (M+H).

methyl 3-(5-(acetylthio)pent-1-yn-1-yl)benzoate

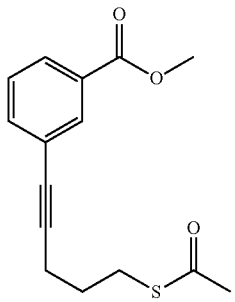 [SMILES: COC(=O)c1cccc(C#CCCCSC(C)=O)c1]

To a solution of methyl 3-(5-hydroxypent-1-yn-1-yl)benzoate (1.93 g, 8.84 mmol) and triethylamine (1.54 ml, 11.05 mmol) in dry DCM (20 mL) under nitrogen and cooled in an ice bath was added methanesulfonyl chloride (0.75 ml, 9.73 mmol) over 5 mins. The reaction mixture was then stirred at it until judged complete by LCMS analysis. The reaction mixture was partitioned with DCM (50 mL) and sat. aq. ammonium chloride (30 mL). The aqueous layer was extracted with DCM (2×15 mL) before the combined organic extracts were washed with water (20 mL) and brine (20 mL) then dried (MgSO₄), filtered and concentrated in vacuo. The residue was then redissolved in dry DMF (25 mL) and treated with potassium ethanethioate (1.01 g, 8.84 mmol) and stirred at rt until judged complete by LCMS analysis. The reaction mixture was then partitioned between EtOAc (100 mL) and water (100 mL). The aqueous layer was extracted with EtOAc (3×30 mL) before the combined organic extracts were washed with water (5×30 mL), brine (30 mL) then dried (MgSO₄), filtered and concentrated in vacuo. The crude material was purified by chromatography (0-10% EtOAc in iso-hexanes) to give methyl 3-(5-(acetylthio)pent-1-yn-1-yl)benzoate (2.2 g, 85% yield) as an orange free-flowing oil.

δ(¹H) DMSO-d₆: 1.74-1.86 (2H, m), 2.34 (3H, s), 2.51-2.54 (2H, m), 2.95-3.03 (2H, m), 3.86 (3H, s), 7.49-7.55 (1H, m), 7.65-7.70 (1H, m), 7.89-7.94 (2H, m) ppm.

MS(ES+) m/z 277 (M+H).

5-(3-(methoxycarbonyl)phenyl)pent-4-yne-1-sulfonic acid

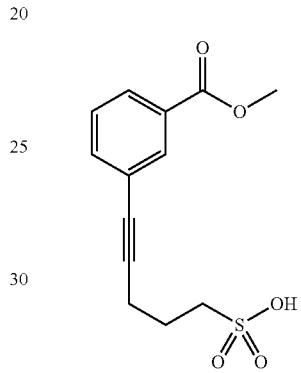

Procedure followed from PCT 2003035627.

To a solution of methyl 3-(5-(acetylthio)pent-1-yn-1-yl)benzoate (2.2 g, 7.96 mmol) in AcOH (10 mL) was added a solution of hydrogen peroxide (9.76 ml, 127 mmol) in AcOH (20 mL). The reaction mixture was stirred at it until complete by LC-MS analysis then cooled in an ice bath and quenched by the addition of 5% Pd/C (200 mg). The mixture was stirred for 20 min then filtered through a pad of celite and the volatiles were removed in vacuo. The residue was then azeoptroped with toluene (3×20 mL) to give 5-(3-(methoxycarbonyl)phenyl)pent-4-yne-1-sulfonic acid (1.9 g, 80%) as a brown semi-solid.

MS(ES+) m/z 281 (M+H).

methyl 3-(5-(N,N-dimethylsulfamoyl)pent-1-yn-1-yl)benzoate

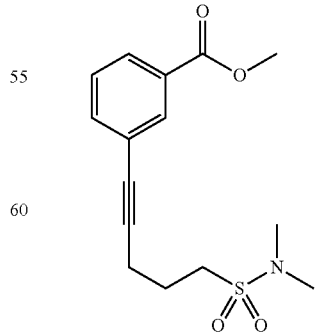

A solution of 5-(3-(methoxycarbonyl)phenyl)pent-4-yne-1-sulfonic acid (1.9 g, 6.39 mmol) in dry DCM (30 mL) and dry DMF (2 drops) was treated with oxalyl dichloride (7.0 ml, 83.18 mmol) in 3 portions. The reaction was stirred at rt until judged complete by LCMS analysis. The volatiles were removed in vacuo and the residue was placed under nitrogen and redissolved in dry THF (10 mL) then treated with dimethylamine (2.0 M in THF) (32.0 ml, 63.9 mmol). The reaction mixture was stirred at it until complete by LCMS then partitioned between EtOAc (100 mL) and 10% aq. citric acid (100 mL). The aqueous layer was extracted with EtOAc (2×100 mL) before the combined organic extracts were washed sequentially with 10% aq. citric acid ((50 mL), sat. aq. sodium bicarbonate (50 mL), water (50 mL) and brine (50 mL) then dried (MgSO$_4$), filtered and concentrated in vacuo. Purification was achieved by chromatography (10-50% EtOAc in iso-hexanes) to give methyl 3-(5-(N,N-dimethylsulfamoyl)pent-1-yn-1-yl)benzoate (1.6 g, 76% yield) as a pale yellow free-flowing oil.

δ($^1$H) DMSO-d$_6$: 1.90-1.95 (2H, m), 2.61 (2H, t, J=7.1 Hz), 2.79 (6H, s), 3.14-3.22 (2H, m), 3.86 (3H, s), 7.52 (1H, dt, J=0.9, 7.6 Hz), 7.65-7.73 (1H, m), 7.89-7.95 (2H, m) ppm.

MS(ES+) m/z 310 (M+H).

3-(5-(N,N-dimethylsulfamoyl)pent-1-yn-1-yl)benzoic acid

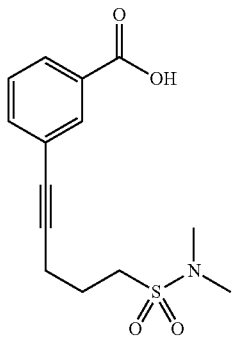 [SMILES: CN(C)S(=O)(=O)CCCC#Cc1cccc(C(=O)O)c1]

To a solution of methyl 3-(5-(N,N-dimethylsulfamoyl) pent-1-yn-1-yl)benzoate (1.60 g, 4.86 mmol) in THF (10 mL) was added a solution of lithium hydroxide (0.23 g, 9.72 mmol) in water (6 mL). The reaction mixture was stirred at it until judged complete by LC-MS then the volatiles were removed in vacuo. The residue as diluted with water (10 mL) and acidified to pH 1 with 1 N HCl (aq.). The resulting white precipitate was collected by filtration and washed with water (2×10 mL), dried by suction for 15 min then in a vacuum oven (40° C.) for 18 h to give 3-(5-(N,N-dimethylsulfamoyl) pent-1-yn-1-yl)benzoic acid (1.27 g, 87% yield) as a white solid.

δ($^1$H) DMSO-d$_6$: 1.87-2.02 (2H, m), 2.61 (2H, t, J=7.0 Hz), 2.79 (6H, s), 3.13-3.25 (2H, m), 7.49 (1H, dt, J=0.8, 7.6 Hz), 7.65 (1H, td, J=1.5, 7.7 Hz), 7.86-7.94 (2H, m), 13.16 (1H, s) ppm.

MS(ES+) m/z 296 (M+H).

(R)-methyl 2-(3-(5-(N,N-dimethylsulfamoyl)pent-1-yn-1-yl)benzamido)propanoate VSN 81

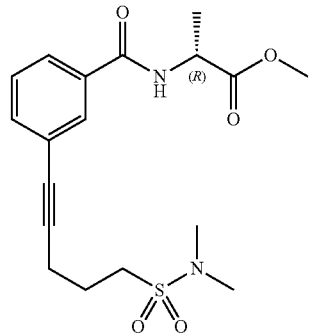

Using the general procedure described for amide coupling, the reaction of 3-(5-(N,N-dimethylsulfamoyl)pent-1-yn-1-yl)benzoic acid (0.81 g, 2.74 mmol), (R)-methyl 2-aminopropanoate.HCl (0.421 g, 3.02 mmol), DIPEA (1.20 ml, 6.86 mmol) and HATU (1.20 g, 3.15 mmol) in dry DCM (20 mL) after purification by chromatography (10-100% EtOAc in iso-hexanes) gave the title compound (R)-methyl 2-(3-(5-(N,N-dimethylsulfamoyl)pent-1-yn-1-yl)benzamido)propanoate (1.0 g, 93% yield) as a yellow oil δ($^1$H) DMSO-d$_6$: 1.40 (3H, d, J=7.3 Hz), 1.96 (2H, dd, J=6.2, 13.9 Hz), 2.62 (2H, t, J=7.1 Hz), 2.79 (6H, s), 3.12-3.24 (2H, m), 3.64 (3H, s), 4.47 (1H, qn, J=7.2 Hz), 7.47 (1H, t, J=7.7 Hz), 7.58 (1H, d, J=7.7 Hz), 7.83 (1H, d, J=7.9 Hz), 7.93 (1H, s), 8.87 (1H, d, J=7.0 Hz) ppm.

δ($^{13}$C) DMSO-d$_6$: 16.66, 17.53, 22.20, 37.07, 45.52, 48.28, 51.89, 80.70, 89.86, 122.92, 127.25, 128.76, 130.11, 133.94, 134.07, 165.40, 173.04 ppm.

MS(ES+) m/z 381 (M+H).

(R,Z)-methyl 2-(3-(5-(N,N-dimethylsulfamoyl)pent-1-en-1-yl)benzamido)propanoate VSN 85

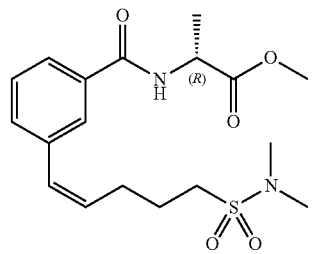

Following the general procedure for the Lindlar reduction, the hydrogenation of (R)-methyl 2-(3-(5-(N,N-dimethylsulfamoyl)pent-1-yn-1-yl)benzamido)propanoate (0.50 g, 1.31 mmol) after separation by column chromatography (0-2% MeOH in DCM) then repurification by column chromatography (10% EtOAc in DCM) and prep. HPLC (30% MeCN in water, acidic) gave the title compound (R,Z)-methyl 2-(3-(5-(N,N-dimethylsulfamoyl)pent-1-en-1-yl) benzamido)propanoate (0.13 g, 24% yield @ 95% purity) as a colourless oil.

δ($^1$H) DMSO-d$_6$: 1.40 (3H, d, J=7.3 Hz), 1.77-1.87 (2H, m), 2.43 (2H, dq, J=1.9, 7.4 Hz), 2.74 (6H, s), 3.03-3.09 (2H, m), 3.65 (3H, s), 4.48 (1H, qn, J=7.3 Hz), 5.75 (1H, td,

J=7.2, 11.7 Hz), 6.52 (1H, td, J=1.9, 11.7 Hz), 7.44-7.49 (2H, m), 7.75-7.78 (2H, m), 8.80 (1H, d, J=6.9 Hz) ppm.

δ($^{13}$C) DMSO-d$_6$: 16.73, 22.86, 26.78, 37.09, 45.79, 48.29, 51.91, 125.82, 127.68, 128.35, 128.96, 131.35, 132.13, 133.80, 136.94, 166.17, 173.18 ppm.

MS(ES+) m/z 383 (M+H).

(R,Z)-2-(3-(5-(N,N-dimethylsulfamoyl)pent-1-en-1-yl)benzamido)propanoic acid VSN 86

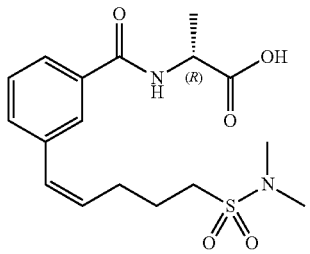

Following the general procedure for saponification, the reaction of (R,Z)-methyl 2-(3-(5-(N,N-dimethylsulfamoyl) pent-1-en-1-yl)benzamido)propanoate (0.075 g, 0.20 mmol) with lithium hydroxide (9.4 mg, 0.39 mmol) gave (R,Z)-2-(3-(5-(N,N-dimethylsulfamoyl)pent-1-en-1-yl)benzamido) propanoic acid (68 mg, 89% yield) as a white solid.

δ($^1$H) DMSO-d$_6$: 1.40 (3H, d, J=7.4 Hz), 1.75-1.85 (2H, m), 2.39-2.48 (2H, m), 2.75 (6H, s), 3.02-3.11 (2H, m), 4.36-4.47 (1H, m), 5.76 (1H, td, J=7.2, 11.7 Hz), 6.53 (1H, br d, J=11.7 Hz), 7.44-7.51 (2H, m), 7.76-7.79 (2H, m), 8.70 (1H, d, J=7.2 Hz), 12.57 (1H, br s) ppm.

δ($^{13}$C) DMSO-d$_6$: 16.89, 22.87, 26.81, 37.11, 45.79, 48.18, 125.81, 127.69, 128.32, 129.02, 131.24, 132.09, 134.06, 136.91, 166.06, 174.25 ppm.

MS(ES+) m/z 369 (M+H).

Synthesis of VSN 82, 87 and 88 methyl 3-(5-(2-oxopyridin-1(2H)-yl)pent-1-yn-1-yl) benzoate

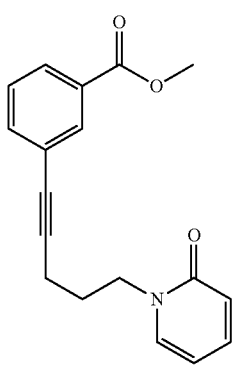 [SMILES: COC(=O)c1cccc(C#CCCCn2ccccc2=O)c1]

A suspension of methyl 3-(5-((methylsulfonyl)oxy)pent-1-yn-1-yl)benzoate (1.15 g, 3.88 mmol), pyridin-2(1H)-one (0.41 g, 4.27 mmol) and potassium carbonate (1.07 g, 7.76 mmol) in dry MeCN (12 mL) under nitrogen was heated to 60° C. for 18 h. Then the mixture was allowed to cool to rt before it was partitioned between EtOAc (50 mL) and water (50 mL). The aqueous layer was extracted with EtOAc (2×30 mL) and the combined organic extracts were washed with water (30 mL) and brine (30 mL) then dried (MgSO$_4$), filtered and concentrated in vacuo. Purification was achieved by chromatography (0-100% EtOAc in iso-hexanes) to give the title product methyl 3-(5-(2-oxopyridin-1(2H)-yl)pent-1-yn-1-yl)benzoate (0.63 g, 53.9% yield) as a clear colourless oil.

δ($^1$H) DMSO-d$_6$: 1.93 (2H, qn, J=7.1 Hz), 2.47 (2H, t, J=7.1 Hz), 3.86 (3H, s), 3.97-4.04 (2H, m), 6.21 (1H, dt, J=1.4, 6.7 Hz), 6.35-6.40 (1H, m), 7.39 (1H, ddd, J=2.1, 6.6, 8.9 Hz), 7.47-7.54 (1H, m), 7.66 (1H, td, J=1.5, 7.8 Hz), 7.69 (1H, ddd, J=0.7, 2.1, 6.8 Hz), 7.88-7.91 (2H, m) ppm.

δ($^{13}$C) DMSO-d$_6$: 16.08, 27.39, 30.65, 47.98, 52.30, 79.85, 90.70, 105.18, 119.62, 123.62, 128.50, 129.15, 129.97, 131.74, 135.77, 139.18, 139.84, 161.45, 165.54 ppm.

MS(ES+) m/z 296 (M+H).

3-(5-(2-oxopyridin-1(2H)-yl)pent-1-yn-1-yl)benzoic acid

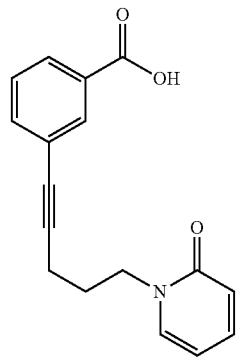 [SMILES: O=C(O)c1cccc(C#CCCCn2ccccc2=O)c1]

To a solution of methyl 3-(5-(2-oxopyridin-1(2H)-yl) pent-1-yn-1-yl)benzoate (0.63 g, 2.13 mmol) in THF (10 mL) was added a solution of lithium hydroxide (0.10 g, 4.27 mmol) in water (3.0 mL). The resulting mixture was stirred at rt for 16 h before the volatiles were removed in vacuo. The residue was then partitioned between 1 N HCl (30 mL) and EtOAc (50 mL) and the aqueous layer was extracted with EtOAc (2×40 mL). The combined organic extracts were washed with water (30 mL) and brine (30 mL) then dried (MgSO$_4$), filtered and concentrated in vauco to give the title compound 3-(5-(2-oxopyridin-1(2H)-yl)pent-1-yn-1-yl) benzoic acid (0.6 g, 98% yield) as an off-white solid.

δ($^1$H) DMSO-d$_6$: 1.93 (2H, qn, J=7.0 Hz), 2.43-2.49 (2H, m), 4.01 (2H, t, J=7.1 Hz), 6.21 (1H, dt, J=1.3, 6.7 Hz), 6.34-6.42 (1H, m), 7.39 (1H, ddd, J=2.1, 6.6, 8.9 Hz), 7.45-7.52 (1H, m), 7.63 (1H, td, J=1.4, 7.7 Hz), 7.69 (1H, dd, J=1.6, 6.7 Hz), 7.85-7.93 (2H, m), 13.15 (1H, s) ppm.

MS(ES+) m/z 282 (M+H).

(R)-methyl 2-(3-(5-(2-oxopyridin-1(2H)-yl)pent-1-yn-1-yl)benzamido)propanoate VSN 82

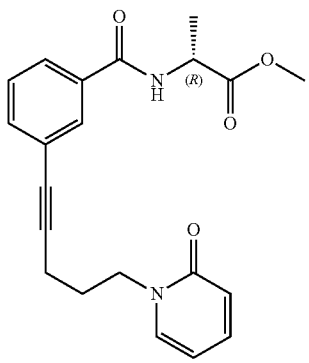

Following the general procedure described for amide coupling, the reaction of 3-(5-(2-oxopyridin-1(2H)-yl)pent-1-yn-1-yl)benzoic acid (0.60 g, 2.13 mmol), (R)-methyl 2-aminopropanoate.HCl (0.30 g, 2.13 mmol), DIPEA (0.37 ml, 2.13 mmol) and HATU (0.81 g, 2.13 mmol) in dry DCM (10 mL) after purification by chromatography (1-5% MeOH in DCM) gave (R)-methyl 2-(3-(5-(2-oxopyridin-1(2H)-yl)pent-1-yn-1-yl)benzamido)propanoate (0.43 g, 53.4% yield) as a viscous colourless oil.

$\delta(^1H)$ DMSO-$d_6$: 1.40 (3H, d, J=7.3 Hz), 1.93 (2H, qn, J=7.1 Hz), 2.44-2.50 (2H, m), 3.64 (3H, s), 3.97-4.05 (2H, m), 4.47 (1H, qn, J=7.2 Hz), 6.22 (1H, dt, J=1.4, 6.7 Hz), 6.36-6.40 (1H, m), 7.40 (1H, ddd, J=2.1, 6.6, 8.9 Hz), 7.46 (1H, t, J=7.8 Hz), 7.57 (1H, td, J=1.3, 7.7 Hz), 7.66-7.73 (1H, m), 7.82 (1H, td, J=1.5, 7.8 Hz), 7.92 (1H, t, J=1.5 Hz), 8.87 (1H, d, J=6.9 Hz) ppm.

$\delta(^{13}C)$ DMSO-$d_6$: 16.05, 16.66, 27.51, 47.99, 48.29, 51.89, 80.35, 90.21, 105.23, 119.63, 123.10, 127.13, 128.68, 130.11, 133.90, 134.09, 139.14, 139.88, 161.44, 165.43, 173.05 ppm.

MS(ES+) m/z 367 (M+H).

(R,Z)-methyl 2-(3-(5-(2-oxopyridin-1(2H)-yl)pent-1-en-1-yl)benzamido)propanoate VSN 87

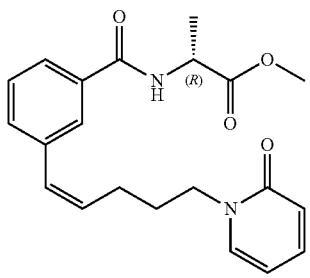

Following the general procedure for the Lindlar reduction, the hydrogenation of (R)-methyl 2-(3-(5-(2-oxopyridin-1(2H)-yl)pent-1-yn-1-yl)benzamido)propanoate (0.30 g, 0.82 mmol) gave the named product along with the fully saturated product (30%) (determined by $^1H$ NMR). Separation by column chromatography (EtOAc) and further purification by prep. HPLC (25% MeCN/water, acidic) gave the title compound (R,Z)-methyl 2-(3-(5-(2-oxopyridin-1(2H)-yl)pent-1-en-1-yl)benzamido)propanoate (87 mg, 28% yield) as a colourless gum. The other component was not isolated.

$\delta(^1H)$ DMSO-$d_6$: 1.41 (3H, d, J=7.3 Hz), 1.79 (2H, qn, J=7.5 Hz), 2.23-2.38 (2H, m), 3.65 (3H, s), 3.83-3.92 (2H, m), 4.49 (1H, qn, J=7.3 Hz), 5.77 (1H, td, J=7.3, 11.7 Hz), 6.14 (1H, dt, J=1.4, 6.7 Hz), 6.33-6.38 (1H, m), 6.51 (1H, br d, J=11.7 Hz), 7.38 (1H, ddd, J=2.1, 6.6, 8.9 Hz), 7.41-7.50 (2H, m), 7.62 (1H, dd, J=1.6, 6.8 Hz), 7.76 (2H, dd, J=1.9, 3.8 Hz), 8.84 (1H, d, J=6.9 Hz) ppm.

$\delta(^{13}C)$ DMSO-$d_6$: 16.76, 25.23, 28.71, 48.16, 48.31, 51.94, 105.14, 119.57, 125.83, 127.67, 128.32, 128.69, 131.30, 132.46, 133.82, 136.97, 139.11, 139.84, 161.38, 166.20, 173.22 ppm.

MS(ES+) m/z 369 (M+H).

R,Z)-2-(3-(5-(2-oxopyridin-1(2H)-yl)pent-1-en-1-yl)benzamido)propanoic acid VSN 88

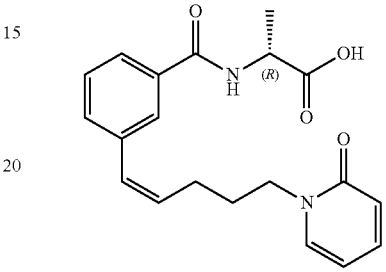

Following the general procedure for saponification, the reaction of (R,Z)-methyl 2-(3-(5-(2-oxopyridin-1(2H)-yl)pent-1-en-1-yl)benzamido)propanoate (40 mg, 0.11 mmol) with lithium hydroxide (5.2 mg, 0.22 mmol) gave (R,Z)-2-(3-(5-(2-oxopyridin-1(2H)-yl)pent-1-en-1-yl)benzamido)propanoic acid (30 mg, 76% yield) as a white solid.

$\delta(^1H)$ DMSO-$d_6$: 1.40 (3H, d, J=7.4 Hz), 1.78 (2H, qn, J=7.5 Hz), 2.25-2.36 (2H, m), 3.83-3.92 (2H, m), 4.42 (1H, qn, J=7.5 Hz), 5.76 (1H, td, J=7.3, 11.7 Hz), 6.13 (1H, dt, J=1.4, 6.7 Hz), 6.32-6.37 (1H, m), 6.50 (1H, br d, J=11.6 Hz), 7.37 (1H, ddd, J=2.1, 6.6, 9.0 Hz), 7.40-7.48 (2H, m), 7.60 (1H, dd, J=1.5, 6.8 Hz), 7.74-7.76 (2H, m), 8.67 (1H, d, J=7.3 Hz), 12.47 (1H, s) ppm.

$\delta(^{13}C)$ DMSO-$d_6$: 16.89, 25.19, 28.66, 48.12, 48.17, 105.08, 119.53, 125.74, 127.60, 128.21, 128.69, 131.11, 132.35, 134.09, 136.89, 139.04, 139.76, 161.34, 166.03, 174.21 ppm.

MS(ES+) m/z 355 (M+H).

Synthesis of VSN 83, 89 and 90 methyl 3-(5-(methylamino)pent-1-yn-1-yl)benzoate

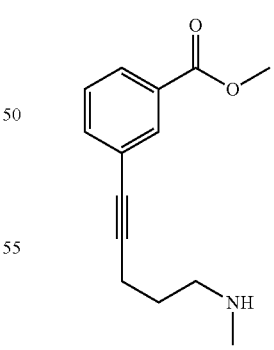

To a solution of methyl 3-(5-((methylsulfonyl)oxy)pent-1-yn-1-yl)benzoate (2.40 g, 8.10 mmol) in dry THF (25.0 mL) was added methanamine (40 wt % in water) (7.01 ml, 81 mmol). The reaction was then stirred at 45° C. until judged complete by LCMS analysis. The reaction mixture was then partitioned between EtOAc (150 mL) and sat. aq. sodium bicarbonate (100 mL) and the aqueous layer was extracted with EtOAc (2×100 mL). The combined organic extracts were washed with water (3×100 mL) and brine (50 mL) then dried (MgSO$_4$), filtered and concentrated in vacuo to give the title product methyl 3-(5-(methylamino)pent-1-yn-1-yl)benzoate (2.0 g, 70.5% yield, 66% purity) as a 2:1 mixture with N-methyl-3-(5-(methylamino)pent-1-yn-1-yl)benzamide. No further purification attempted.

MS(ES+) m/z 232 (M+H).

methyl 3-(5-(N-methylacetamido)pent-1-yn-1-yl)benzoate

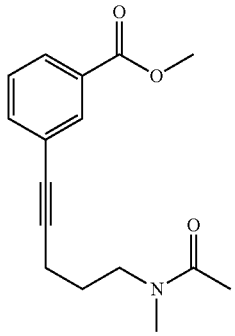 [SMILES: COC(=O)c1cccc(C#CCCCN(C)C(C)=O)c1]

A solution of methyl 3-(5-(methylamino)pent-1-yn-1-yl)benzoate (1.05 g, 4.54 mmol) (66% purity) and DIPEA (1.59 ml, 9.08 mmol) in dry DCM (10 mL) was treated with acetyl chloride (0.48 ml, 6.81 mmol). The reaction mixture was stirred at rt until judged complete by LCMS analysis. The volatiles were then removed in vacuo and the residue was partitioned between EtOAc (50 mL) and 1 N HCl (25 mL) and the aqueous layer was extracted with EtOAc (2×30 mL). The combined organic layers were washed with sat. aq. NaHCO$_3$ (25 mL), water (25 mL) and brine (25 mL) then dried (MgSO$_4$), filtered and concentrated in vacuo to give methyl 3-(5-(N-methylacetamido)pent-1-yn-1-yl)benzoate (1.20 g, 63.8% yield) as a 2:1 mixture with N-methyl-3-(5-(N-methylacetamido)pent-1-yn-1-yl)benzamide.

MS(ES+) m/z 274 (M+H).

3-(5-(N-methylacetamido)pent-1-yn-1-yl)benzoic acid

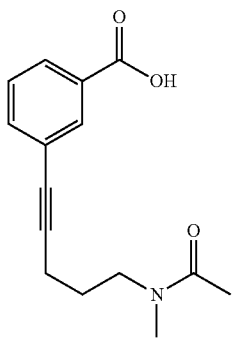 [SMILES: CC(=O)N(C)CCCC#Cc1cccc(C(=O)O)c1]

To a solution of methyl 3-(5-(N-methylacetamido)pent-1-yn-1-yl)benzoate (1.20 g, 4.39 mmol) in THF (15 mL) was added a solution of lithium hydroxide (0.210 g, 8.78 mmol) in water (3.0 mL). The reaction mixture was stirred at rt until judged complete by LCMS. The volatiles were removed in vacuo and the residue was partitioned between EtOAc (20 mL) and water (20 mL). The aqueous layer was extracted with with EtOAc (3×20 mL) then acidified to pH 1 with 1 N HCl and extracted with EtOAc (3×20 mL). The combined organic extracts were washed with water (20 mL) and brine (20 mL) then dried (MgSO$_4$), filtered and concentrated in vacuo to give 3-(5-(N-methylacetamido)pent-1-yn-1-yl)benzoic acid (0.68 g, 56.7% yield) as a viscous brown oil.

δ($^1$H) DMSO-d$_6$: 1.67-1.87 (2H, m), 1.91 (1.5H, s), 1.98 (1.5H, s), 2.41 (1H, t, J=7.1 Hz), 2.45-2.49 (1H, m), 2.80 (1.5H, s), 2.97 (1.5H, s), 3.34-3.46 (2H, m), 7.44-7.53 (1H, m), 7.59-7.66 (1H, m), 7.85-7.94 (2H, m), 12.79 (1H, s) ppm (compound rotomeric hence some resonances are split).

MS(ES+) m/z 260 (M+H).

(R)-methyl 2-(3-(5-(N-methylacetamido)pent-1-yn-1-yl)benzamido)propanoate VSN 83

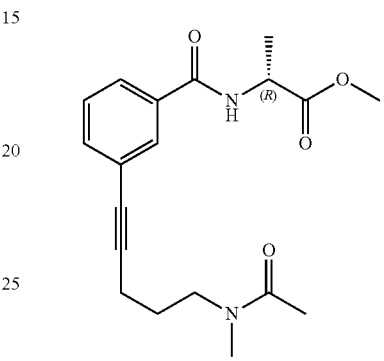

Following the general procedure described for amide coupling, the reaction of 3-(5-(N-methylacetamido)pent-1-yn-1-yl)benzoic acid (0.68 g, 2.49 mmol), (R)-methyl 2-aminopropanoate.HCl (0.35 g, 2.49 mmol), HATU (1.14 g, 2.99 mmol) and DIPEA (1.33 ml, 7.47 mmol) in dry DCM (10 mL) after purification by chromatography (1-3% MeOH in DCM) gave (R)-methyl 2-(3-(5-(N-methylacetamido)pent-1-yn-1-yl)benzamido)propanoate (0.40 g, 45.7% yield) as a pale yellow oil.

δ($^1$H) DMSO-d$_6$ (@ 100° C.): 1.43 (3H, d, J=7.3 Hz), 1.77-1.87 (2H, m), 2.01 (3H, s), 2.43-2.50 (2H, m), 2.94 (3H, s), 3.39-3.48 (2H, m), 3.68 (3H, s), 4.54 (1H, qn, J=7.2 Hz), 7.43 (1H, t, J=7.7 Hz), 7.53 (1H, td, J=1.4, 7.7 Hz), 7.81 (1H, td, J=1.5, 7.8 Hz), 7.89 (1H, t, J=1.5 Hz), 8.50 (1H, br s) ppm.

δ($^{13}$C) DMSO-d$_6$: 15.90, 16.30, 16.66, 21.06, 21.72, 26.07, 26.74, 32.47, 35.81, 45.97, 48.28, 48.82, 51.89, 79.95, 80.31, 90.57, 90.98, 123.07, 123.23, 127.07, 127.13, 128.73, 128.76, 130.01, 130.06, 133.93, 133.95, 134.00, 165.42, 169.31, 169.66, 173.05 ppm. (Note: some peaks are doubled as compound is rotomeric).

MS(ES+) m/z 345 (M+H).

(R,Z)-methyl 2-(3-(5-(N-methylacetamido)pent-1-en-1-yl)benzamido)propanoate VSN 89

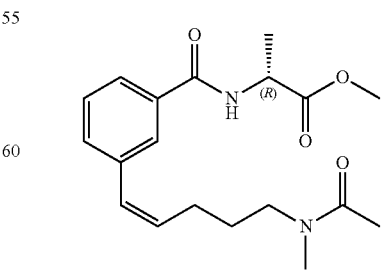

Following the general procedure for the Lindlar reduction, the hydrogenation of (R)-methyl 2-(3-(5-(N-methylacetamido)pent-1-yn-1-yl)benzamido)propanoate (0.32 g, 0.93 mmol) after separation by column chromatography (0-2% MeOH in DCM) and preparative HPLC (20-30% MeCN, acidic) gave the title compound (R,Z)-methyl 2-(3-(5-(N-methylacetamido)pent-1-en-1-yl)benzamido)propanoate (0.16 g, 48% yield) as a colourless oil.

δ($^1$H) DMSO-d$_6$ (@ 100° C.): 1.44 (3H, d, J=7.3 Hz), 1.63-1.75 (2H, m), 1.95 (3H, s), 2.24-2.35 (2H, m), 2.95 (3H, s), 3.25-3.33 (2H, m), 3.68 (3H, s), 4.55 (1H, qn, J=7.2 Hz), 5.77 (1H, td, J=7.3, 11.7 Hz), 6.49 (1H, d, J=11.7 Hz), 7.41-7.49 (2H, m), 7.70-7.80 (2H, m), 8.42 (1H, d, J=5.9 Hz) ppm.

δ($^{13}$C) DMSO-d$_6$: 16.73, 21.04, 21.70, 25.34, 25.54, 26.97, 27.85, 32.53, 35.62, 46.17, 48.30, 49.40, 51.92, 125.73, 125.79, 127.58, 127.61, 128.31, 128.34, 128.60, 131.36, 131.42, 132.77, 133.04, 133.77, 133.79, 137.02, 137.09, 166.18, 166.22, 169.23, 169.50, 173.20 ppm (Note: some peaks are doubled as compound is rotomeric).

MS(ES+) m/z 347 (M+H).

(R,Z)-2-(3-(5-(N-methylacetamido)pent-1-en-1-yl)benzamido)propanoic acid VSN 90

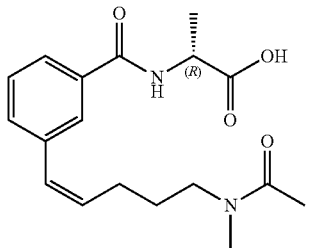

Following the general procedure for saponification, the reaction of (R,Z)-methyl 2-(3-(5-(N-methylacetamido)pent-1-en-1-yl)benzamido)propanoate (0.10 g, 0.289 mmol) with lithium hydroxide (14 mg, 0.58 mmol) gave (R,Z)-2-(3-(5-(N-methylacetamido)pent-1-en-1-yl)benzamido)propanoic acid (85 mg, 86% yield) as a colourless gum.

δ($^1$H) DMSO-d$_6$ (@100° C.): 1.43 (3H, d, J=7.3 Hz), 1.67 (2H, m), 1.95 (3H, s), 2.24-2.35 (2H, m), 2.86 (3H, br s), 3.26-3.34 (2H, m), 4.49 (1H, qn, J=7.3 Hz), 5.77 (1H, td, J=7.3, 11.7 Hz), 6.49 (1H, br d, J=11.6 Hz), 7.40-7.48 (2H, m), 7.71-7.79 (2H, m), 8.26 (1H, m) ppm. Note: No OH observed.

δ($^{13}$C) DMSO-d$_6$: 16.88, 21.05, 21.71, 25.35, 25.54, 26.98, 27.85, 32.55, 35.64, 46.19, 48.17, 49.41, 125.71, 125.77, 127.57, 127.60, 128.26, 128.29, 128.34, 128.64, 131.23, 131.30, 132.71, 132.99, 134.04, 134.05, 136.97, 137.05, 166.07, 166.11, 169.23, 169.50, 174.24 ppm (Note: some peaks are doubled as compound is rotomeric).

MS(ES+) m/z 333 (M+H).

Synthesis of VSN 84, 91 and 92 methyl 3-(5-(N-methylmethylsulfonamido)pent-1-yn-1-yl)benzoate

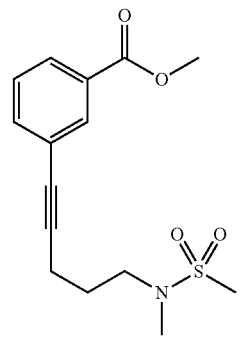 [SMILES: COC(=O)c1cccc(C#CCCCN(C)S(C)(=O)=O)c1]

A solution of methyl 3-(5-(methylamino)pent-1-yn-1-yl)benzoate (1.0 g, 4.32 mmol) (66% purity), DIPEA (1.13 ml, 6.49 mmol) in dry DCM (10 mL) was treated with methanesulfonyl chloride (0.42 ml, 5.40 mmol). The reaction mixture was stirred at rt until judged complete by LCMS analysis. The reaction mixture was partitioned between DCM (50 mL) and 1 N HCl (25 mL). The aq. layer was extracted with DCM (2×30 mL) before the combined organic extracts were washed with water (25 mL) and brine (25 mL) then dried (MgSO$_4$), filtered and concentrated in vacuo to give methyl 3-(5-(N-methylmethylsulfonamido)pent-1-yn-1-yl)benzoate (1.20 g, 59.2% yield) as a 2:1 mixture with N-methyl-3-(5-(N-methylmethylsulfonamido)pent-1-yn-1-yl)benzamide. Carried forward as a mixture.

MS(ES+) m/z 310 (M+H).

3-(5-(N-methylmethylsulfonamido)pent-1-yn-1-yl)benzoic acid

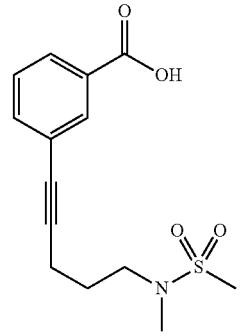 [SMILES: CN(CCCC#Cc1cccc(C(=O)O)c1)S(C)(=O)=O]

To a solution of methyl 3-(5-(N-methylmethylsulfonamido)pent-1-yn-1-yl)benzoate (1.20 g, 3.88 mmol) in THF (15 mL) was added a solution of lithium hydroxide (0.19 g, 7.76 mmol) in water (3.0 mL) The reaction mixture was stirred at rt until judged complete by LCMS. The volatiles were removed in vacuo and the residue was partitioned between EtOAc (20 mL) and water (20 mL). The aq. layer was acidified to pH 1 with 1 N HCl and extracted with EtOAc (3×30 mL). The combined organic extracts were washed with water (30 mL) and brine (30 mL) then dried (MgSO$_4$), filtered and concentrated in vacuo to give 3-(5-(N-methylmethylsulfonamido)pent-1-yn-1-yl)benzoic acid (0.50 g, 42.8% yield) as a pale brown solid.

δ($^1$H) DMSO-d$_6$: 1.81 (2H, qn, J=7.1 Hz), 2.44-2.49 (2H, m), 2.77 (3H, s), 2.88 (3H, s), 3.14-3.22 (2H, m), 7.45-7.52 (1H, m), 7.63 (1H, td, J=1.4, 7.7 Hz), 7.85-7.93 (2H, m), 13.13 (1H, s) ppm.

MS(ES+) m/z 296 (M+H).

(R)-methyl 2-(3-(5-(N-methylmethylsulfonamido)pent-1-yn-1-yl)benzamido)propanoate VSN 84

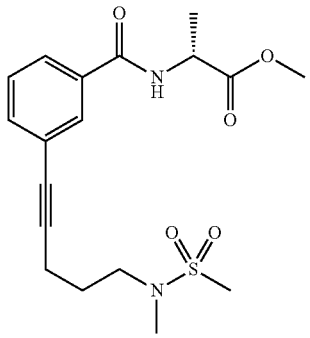 [SMILES: COC(=O)[C@@H](C)NC(=O)c1cccc(C#CCCCN(C)S(C)(=O)=O)c1]

Following the general procedure described for amide coupling, the reaction of 3-(5-(N-methylmethylsulfonamido)pent-1-yn-1-yl)benzoic acid (0.50 g, 1.69 mmol), (R)-methyl 2-aminopropanoate.HCl (0.26 g, 1.86 mmol), HATU (0.74 g, 1.95 mmol) and DIPEA (0.739 ml, 4.23 mmol) in dry DCM (10 mL) after purification by chromatography (30-70% EtOAc in iso-hexanes) gave (R)-methyl 2-(3-(5-(N-methylmethylsulfonamido)pent-1-yn-1-yl)benzamido)propanoate (0.39 g, 57.5% yield) as a pale yellow oil.

δ($^1$H) DMSO-d$_6$: 1.40 (3H, d, J=7.3 Hz), 1.82 (2H, qn, J=7.1 Hz), 2.46-2.49 (2H, m), 2.77 (3H, s), 2.88 (3H, s), 3.18 (2H, t, J=7.0 Hz), 3.64 (3H, s), 4.47 (1H, qn, J=7.1 Hz), 7.46 (1H, t, J=7.8 Hz), 7.56 (1H, td, J=1.3, 7.7 Hz), 7.82 (1H, td, J=1.4, 7.8 Hz), 7.91 (1H, t, J=1.5 Hz), 8.86 (1H, d, J=6.9 Hz) ppm.

δ($^{13}$C) DMSO-d$_6$: 15.92, 16.66, 26.59, 34.54, 34.57, 48.28, 48.60, 51.90, 80.18, 90.62, 123.17, 127.09, 128.73, 130.04, 133.93, 134.04, 165.43, 173.05 ppm.

MS(ES+) m/z 381 (M+H).

(R,Z)-methyl 2-(3-(5-(N-methylmethylsulfonamido)pent-1-en-1-yl)benzamido)propanoate VSN 91

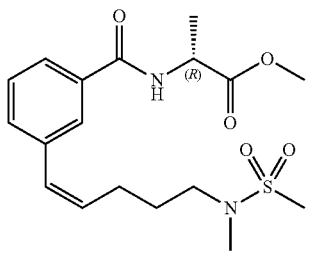

Following the general procedure for the Lindlar reduction, the hydrogenation of (R)-methyl 2-(3-(5-(N-methylmethylsulfonamido)pent-1-yn-1-yl)benzamido)propanoate (0.32 g, 0.84 mmol) gave the named product along with the trans double bond isomer (<5%) and fully saturated product (10%) (determined by $^1$H NMR). Separation by column chromatography (10% EtOAc in DCM) gave the title compound (R,Z)-methyl 2-(3-(5-(N-methylmethylsulfonamido)pent-1-en-1-yl)benzamido)propanoate (0.19 g, 59% yield) as a colourless oil. The other 2 components were not isolated.

δ($^1$H) DMSO-d$_6$: 1.40 (3H, d, J=7.3 Hz), 1.68 (2H, qn, J=7.1 Hz), 2.26-2.35 (2H, m), 2.72 (3H, s), 2.83 (3H, s), 3.03-3.07 (2H, m), 3.64 (3H, s), 4.48 (1H, qn, J=7.2 Hz), 5.77 (1H, td, J=7.3, 11.8 Hz), 6.50 (1H, td, J=1.8, 11.8 Hz), 7.43-7.51 (2H, m), 7.73-7.80 (2H, m), 8.80 (1H, d, J=6.9 Hz) ppm. Note: contaminated with 5-10% trans isomer.

δ($^{13}$C) DMSO-d$_6$: 16.71, 25.23, 27.48, 34.41, 34.48, 48.26, 49.04, 51.87, 125.72, 127.60, 128.27, 128.52, 131.29, 132.66, 133.79, 137.02, 166.16, 173.14 ppm.

MS(ES+) m/z 383 (M+H).

(R,Z)-2-(3-(5-(N-methylmethylsulfonamido)pent-1-en-1-yl)benzamido)propanoic acid VSN 92

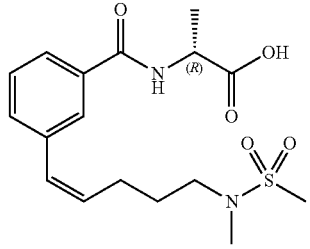

Following the general procedure for saponification, the reaction of (R,Z)-methyl 2-(3-(5-(N-methylmethylsulfonamido)pent-1-en-1-yl)benzamido)propanoate (0.11 g, 0.288 mmol) with lithium hydroxide (14 mg, 0.58 mmol) gave (R,Z)-2-(3-(5-(N-methylmethylsulfonamido)pent-1-en-1-yl)benzamido)propanoic acid (0.1 g, 90% yield) as a white solid. Note: 5% isomerisation to trans double bond under reaction conditions observed.

δ($^1$H) DMSO-d$_6$: 1.43 (3H, d, J=7.3 Hz), 1.72 (2H, qn, J=7.4 Hz), 2.33 (2H, dq, J=1.8, 7.5 Hz), 2.75 (3H, s), 2.81 (3H, s), 3.08-3.14 (2H, m), 4.49 (1H, qn, J=7.3 Hz), 5.78 (1H, td, J=7.3, 11.7 Hz), 6.50 (1H, dd, J=11.7, 1.6 Hz), 7.42-7.47 (2H, m), 7.72-7.78 (2H, m), 8.26 (1H, d, J=6.9 Hz), 12.04 (1H, br s) ppm.

δ($^{13}$C) DMSO-d$_6$: 16.88, 25.27, 27.52, 34.46, 34.48, 48.17, 49.07, 125.74, 127.63, 128.27, 128.59, 131.21, 132.65, 134.05, 137.00, 166.08, 174.24 ppm.

MS(ES+) m/z 369 (M+H).

In Vitro Activity

Compounds were evaluated using a mouse vas deferens preparation [Ward S, Mastriani D, Casiano F and Arnold R (1990) *J Pharmacol Exp Ther* 255:1230-1239]. The mouse vas deferens isolated tissue preparation is used as an in vitro bioassay to assess the actions of compounds on neurotransmission. Electrically-evoked contractions are induced in the preparation and compounds which affect neurotransmission will inhibit these contractions in a concentration related manner. The vas deferens has been widely used to assess the effects of compounds at the cannabinoid CB1 receptor, which is located pre-synaptically. CB1 agonists inhibit electrically-evoked contractions.

Methods

Vasa deferentia were obtained from albino MF1 mice weighing 31-59 g. The tissues were mounted vertically in 4 ml organ baths. They were then subjected to electrical stimulation of progressively greater intensity, followed by an equilibration procedure in which they were exposed to alternate periods of stimulation (2 min) and rest (10 min) until contractions with consistent amplitudes were obtained. These contractions were monophasic and isometric, and were evoked by 0.5 s trains of pulses of 110% maximal voltage (train frequency 0.1 Hz; pulse frequency 5 Hz; pulse duration 0.5 ms).

All drug additions were made to the organ baths after the equilibration period and there was no washout between these additions. Potential antagonist or its vehicle were added to the preparation. This was followed 28 min later by a 2-min period of electrical stimulation, at the end of which the lowest of a series of concentrations of the twitch inhibitors was applied. After a period of rest, the tissues were electrically stimulated for 2 min and then subjected to a further addition of twitch inhibitor. This cycle of drug addition, rest and 2 min stimulation was repeated so as to construct cumulative concentration—response curves. Only one concentration—response curve was constructed per tissue.

Analysis of Data

Inhibition of the electrically-evoked twitch response of the vas deferens has been expressed in percentage terms, and this has been calculated by comparing the amplitude of the twitch response after each addition of a twitch inhibitor with its amplitude immediately before the first addition of the inhibitor. Values for $EC_{50}$, maximal effect ($E_{max}$) and the s.e.m. or 95% confidence limits of these values have been calculated by nonlinear regression analysis using the equation for a sigmoid concentration—response curve (GraphPad Prism).

In Vivo Peripheral $CB_1$ Receptor Activation

Assessment of Spasticity

Further studies were undertaken using cannabinoid knockout mice, including $CB_1$, $CB_2$, VR-1, FAAH and conditional $CB_1$ knockout mice. Spasticity may be induced in ABH (significant spasticity occurs in 50-60% of animals in 80 days after 3-4 disease episodes[1]) or ABH.$CB_1$-/- (significant spasticity occurs in 80-100% of animals in 30-40 days after 1-2 disease episodes). Compounds are injected initially intravenously (to limit first pass effects), i.p. or orally. Spasticity is assessed (n=6-7/group) by resistance to hindlimb flexion using a strain gauge [Baker, D. et al, Nature 2000, 404, 84-87]. Animals serve as their own controls and will be analysed in a pairwise fashion. To reduce the number of animals, effort and expense, following a drug-free period (spasticity returns within 24 h) these animals receive different doses and or vehicle. Low doses of $CB_1$ agonists and CNS active CP55,940, as control, are locally (subcutaneous, intra-muscularly) administered into spastic ABH mice and the lack of activity in a contralateral limb analysed [Fox, A. et al, Pain 2001, 92, 91-100]. Expression of $CB_1$ in the peripheral nervous system, including dorsal root ganglia, a non-CNS site for CB-mediated nociception can be removed using peripherin-Cre transgenic mouse [Zhou, L. et al, FEBS Lett. 2002, 523, 68-72]. These conditional KO mice are maintained on the C57BL/6 background. These mice develop EAE following induction with myelin oligodendrocyte glycoprotein residues 35-55 peptide [Amor, S. et al, J. Immunol. 1994, 153, 4349-4356].

Results

The compounds of the invention inhibited electrically-evoked contractions of the mouse isolated vas deferens in a similar manner to the standard CB1 receptor agonist, WIN55212-2 (Table 1, FIG. 1). Table 1 shows that the potency ($EC_{50}$) of VSN44 is unexpectedly ten-fold greater than for VSN16R (1.42 nM for VSN-44 cf 10.44 nM for VSN-16R). Further results for the vas deferens assay are shown in Table 2 for selected compounds according to the invention.

Figure 3:
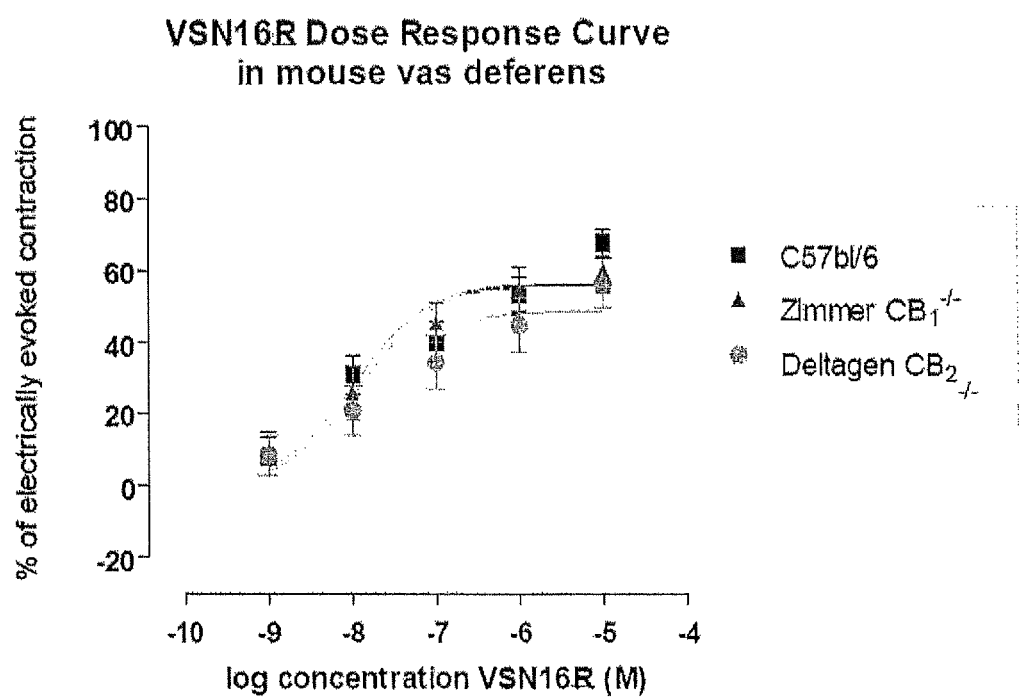
FIG. 3 shows the dose response curve in mouse vas deferens for VSN-16R. The results show that the $EC_{50}$ stays relatively constant across wt, $CB_1$ knock-out and $CB_2$ knock-out.

A VSN-16R dose response curve in mouse vas deferens shows that the $EC_{50}$ stays relatively constant across wild type (10.44 nM), $CB_1$ knock-out (12.66 nM) and $CB_2$ knock-out (17.61 nM); see FIG. 3.

Figure 2:
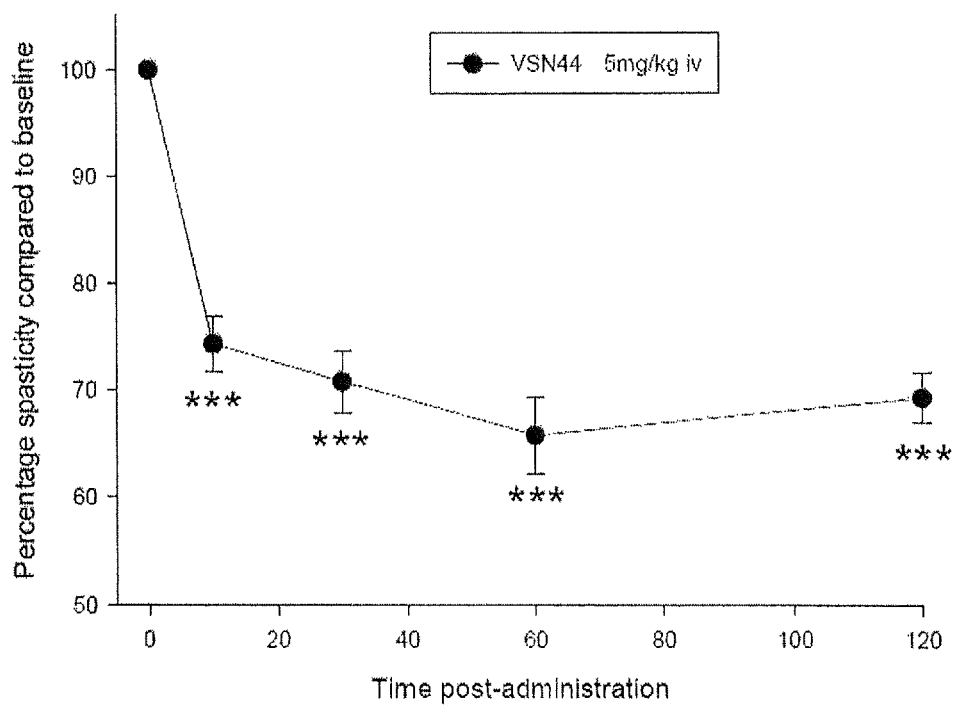
FIG. 2 shows the effect of VNS-44 (5 mg/kg i.v.) on spasticity (% spasticity vs baseline) against time after administration.

FIG. 2 shows the effect of VNS-44 on spasticity (percentage spasticity vs baseline) against time after administration.

CONCLUSIONS

The compounds tested are potent inhibitors of electrically-evoked contractions of the mouse isolated vas deferens. Advantageously, VSN-44 shows at least a 10-fold increase in potency over VSN-16R in the mouse vas deferens study.

Various modifications and variations of the described methods of the invention will be apparent to those skilled in the art without departing from the scope and spirit of the invention. Although the invention has been described in connection with specific preferred embodiments, various modifications of the described modes for carrying out the invention which are obvious to those skilled in chemistry or related fields are intended to be within the scope of the following claims.

TABLE 1

Emax, $pEC_{50}$ ± SEM and $EC_{50}$ values for compound [1] (VSN-44)

| Compound | Emax (%) ± 95% confidence limits | $pEC_{50}$ ± SEM | $EC_{50}$ (nM) |
|---|---|---|---|
| WIN55212-2 | 62 (52-72) | 8.41 ± 0.237 | 3.86 |
| VSN-22R | 43 (28-56) | 8.03 ± 0.367 | 9.42 |
| VSN-44 | 46 (34-58) | 8.85 ± 0.561 | 1.42 |
| VSN16R | 56 (48-64) | −7.98 ± 0.367 | 10.44 |

TABLE 2

Emax, and $EC_{50}$ values for compound selected compounds according to the invention

| Cpd | Structure | Mol Wt | EC50 (nM) | EC50 95% Cls | Emax (%) | Emax 95% Cls |
|---|---|---|---|---|---|---|
| VSN 16R | 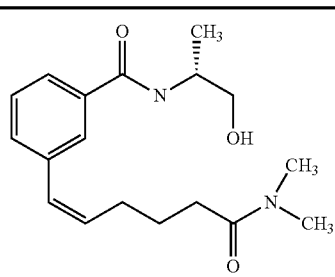 | 318.41952 | 0.7216 | 0.1055-4.94 | 40.71 | 30.1-51.33 |

TABLE 2-continued
Emax, and EC$_{50}$ values for compound selected compounds according to the invention
| Cpd | Structure | Mol Wt | EC50 (nM) | EC50 95% Cls | Emax (%) | Emax 95% Cls |
|---|---|---|---|---|---|---|
| [1] VSN 44R | 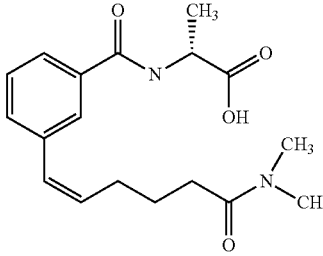 | 332.40298 | 0.006546 | 0.002807-0.01527 | 64.02 | 56.83-71.21 |
| [20] | 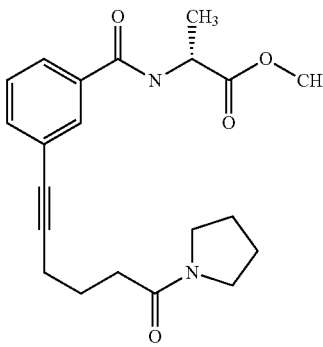 | 370.45237 | 0.4662 | 0.0676-3.2 | 44.73 | 33.83-55.63 |
| [21] | 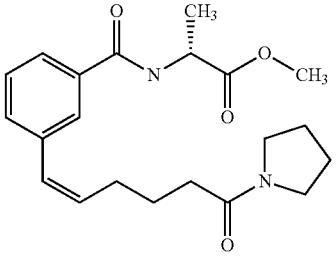 [SMILES: COC(=O)[C@@H](C)NC(=O)c1cccc(/C=C\CCCC(=O)N2CCCC2)c1] | 372.46831 | 0.1617 | 0.04544-0.5754 | 58.31 | 52.45-64.18 |
| [22] | 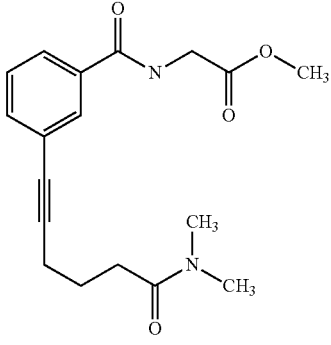 [SMILES: COC(=O)CNC(=O)c1cccc(C#CCCCC(=O)N(C)C)c1] | 330.38704 | 0.1116 | 0.0333-0.3744 | 52.9 | 45.06-60.73 |
| [23] | 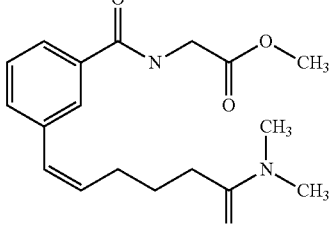 | 332.40298 | 0.02247 | 0.007191-0.0702 | 59.25 | 52.43-66.07 |

TABLE 2-continued

Emax, and EC$_{50}$ values for compound selected compounds according to the invention

| Cpd | Structure | Mol Wt | EC50 (nM) | EC50 95% Cls | Emax (%) | Emax 95% Cls |
|---|---|---|---|---|---|---|
| [15] | 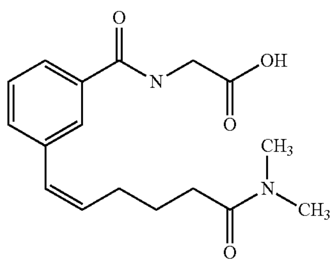 [SMILES: CN(C)C(=O)CCC/C=C\c1cccc(C(=O)NCC(=O)O)c1] | 318.37589 | 0.1024 | 0.04556-0.23 | 53.71 | 48.18-59.23 |
| [24] | 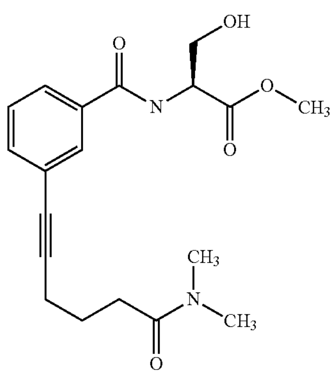 [SMILES: COC(=O)[C@H](CO)NC(=O)c1cccc(C#CCCCC(=O)N(C)C)c1] | 360.41353 | 0.4122 | 0.1221-1.39 | 51.53 | 43.42-59.64 |
| [25] | 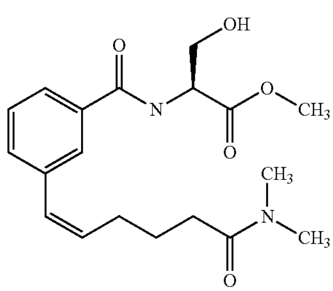 [SMILES: COC(=O)[C@H](CO)NC(=O)c1cccc(/C=C\CCCC(=O)N(C)C)c1] | 362.42947 | 0.3591 | 0.07067-1.83 | 52.86 | 41.81-63.9 |
| [18] | 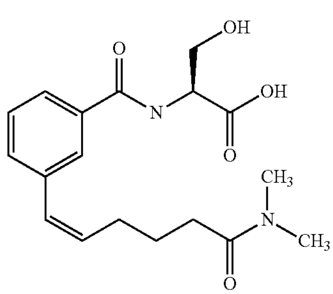 [SMILES: CN(C)C(=O)CCC/C=C\c1cccc(C(=O)N[C@@H](CO)C(=O)O)c1] | 348.40238 | 0.3822 | 0.0931-1.57 | 62.68 | 51.72-73.64 |

TABLE 2-continued

Emax, and EC$_{50}$ values for compound selected compounds according to the invention

| Cpd | Structure | Mol Wt | EC50 (nM) | EC50 95% Cls | Emax (%) | Emax 95% Cls |
|---|---|---|---|---|---|---|
| [27] | 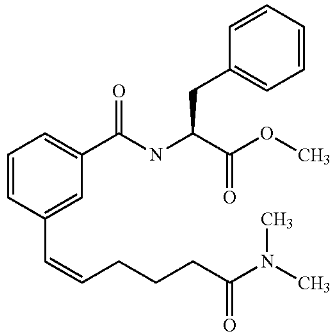 [SMILES: COC(=O)[C@H](Cc1ccccc1)NC(=O)c1cccc(/C=C\CCCC(=O)N(C)C)c1] | 422.52885 | 0.09083 | 0.02804-0.2942 | 55.3 | 47.37-63.24 |
| [17] | 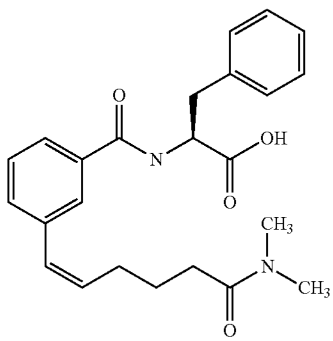 [SMILES: CN(C)C(=O)CCC/C=C\c1cccc(C(=O)N[C@@H](Cc2ccccc2)C(=O)O)c1] | 408.50176 | 0.1397 | 0.03319 | 56.28 | 46.09-66.46 |
| [29] | 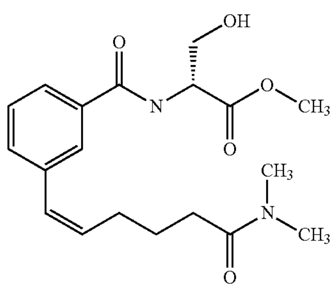 [SMILES: COC(=O)[C@@H](CO)NC(=O)c1cccc(/C=C\CCCC(=O)N(C)C)c1] | 362.42947 | 0.04555 | 0.01725-0.1203 | 62 | 55.16-68.84 |
| [14] | 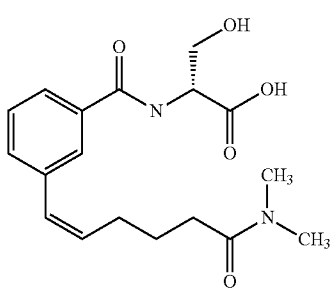 [SMILES: CN(C)C(=O)CCC/C=C\c1cccc(C(=O)N[C@H](CO)C(=O)O)c1] | 348.40238 | 0.1244 | 0.04403-0.3513 | 58.47 | 50.49-66.44 |

TABLE 2-continued

Emax, and EC$_{50}$ values for compound selected compounds according to the invention

| Cpd | Structure | Mol Wt | EC50 (nM) | EC50 95% Cls | Emax (%) | Emax 95% Cls |
|---|---|---|---|---|---|---|
| [30] | 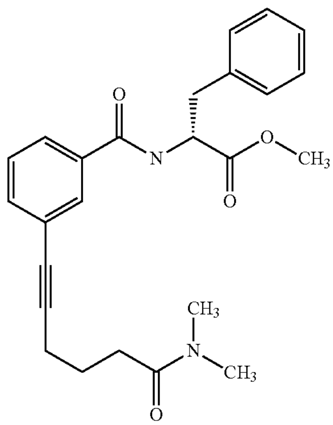 [SMILES: COC(=O)[C@@H](Cc1ccccc1)NC(=O)c1cccc(C#CCCCC(=O)N(C)C)c1] | 420.51291 | 0.06135 | 0.02416-0.1558 | 46.32 | 40.88-51.76 |
| [31] | 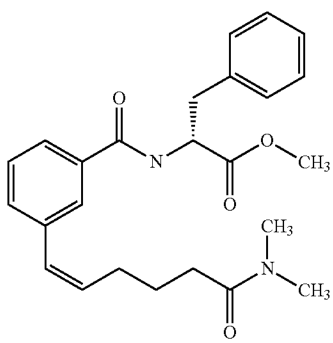 [SMILES: COC(=O)[C@@H](Cc1ccccc1)NC(=O)c1cccc(/C=C\CCCC(=O)N(C)C)c1] | 422.52885 | 0.01224 | 0.002949-0.05084 | 46.99 | 38.74-55.24 |
| [16] | 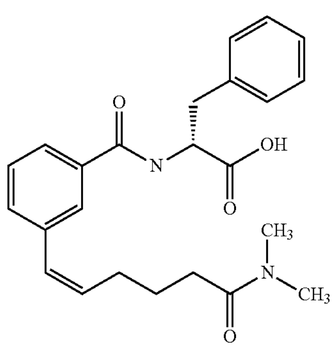 [SMILES: CN(C)C(=O)CCC/C=C\c1cccc(C(=O)N[C@H](Cc2ccccc2)C(=O)O)c1] | 408.50176 | 0.00604 | 0.003016-0.0121 | 73.88 | 68.35-79.4 |
| [32] | 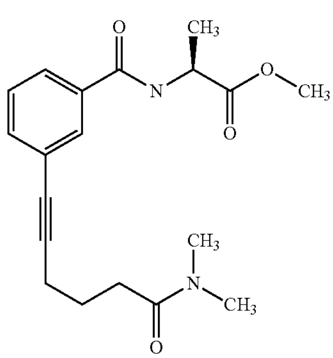 [SMILES: COC(=O)[C@H](C)NC(=O)c1cccc(C#CCCCC(=O)N(C)C)c1] | 344.41413 | 0.01312 | 0.002865-0.06007 | 54.57 | 45.07-64.07 |

TABLE 2-continued

Emax, and EC$_{50}$ values for compound selected compounds according to the invention

| Cpd | Structure | Mol Wt | EC50 (nM) | EC50 95% Cls | Emax (%) | Emax 95% Cls |
|---|---|---|---|---|---|---|
| [33] | 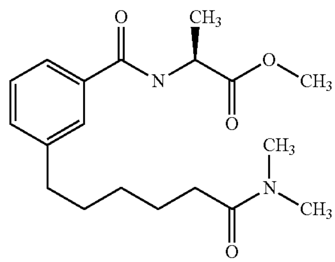 [SMILES: COC(=O)[C@H](C)NC(=O)c1cccc(CCCCCC(=O)N(C)C)c1] | 348.446 | | | | |
| [4] | 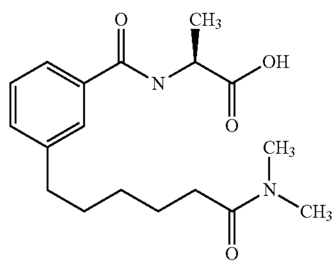 [SMILES: C[C@H](NC(=O)c1cccc(CCCCCC(=O)N(C)C)c1)C(=O)O] | 334.4189 | | | | |
| [34] | 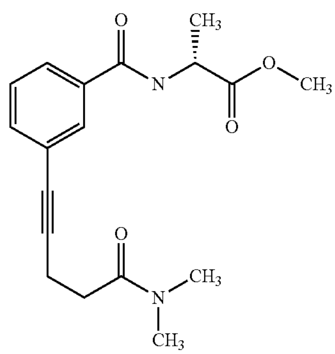 [SMILES: COC(=O)[C@@H](C)NC(=O)c1cccc(C#CCCC(=O)N(C)C)c1] | 330.387 | | | | |
| [35] | 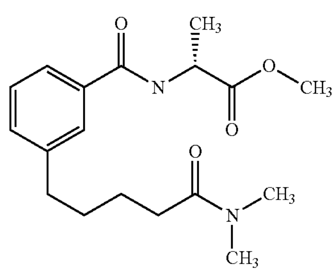 [SMILES: COC(=O)[C@@H](C)NC(=O)c1cccc(CCCCC(=O)N(C)C)c1] | 334.4189 | | | | |
| [36] | 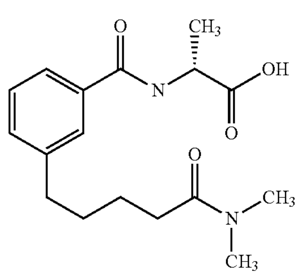 [SMILES: C[C@@H](NC(=O)c1cccc(CCCCC(=O)N(C)C)c1)C(=O)O] | 320.3918 | | | | |

TABLE 2-continued

Emax, and EC$_{50}$ values for compound selected compounds according to the invention

| Cpd | Structure | Mol Wt | EC50 (nM) | EC50 95% Cls | Emax (%) | Emax 95% Cls |
|---|---|---|---|---|---|---|
| [37] | 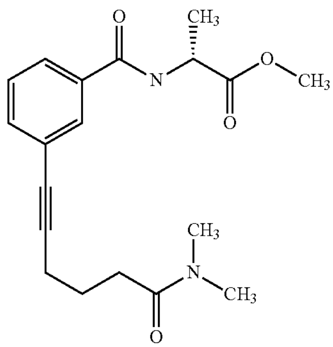 [SMILES: COC(=O)[C@@H](C)NC(=O)c1cccc(C#CCCCC(=O)N(C)C)c1] | 344.4141 | | | | |
| [38] | 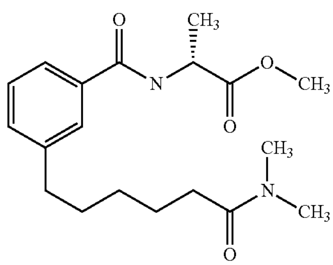 [SMILES: COC(=O)[C@@H](C)NC(=O)c1cccc(CCCCCC(=O)N(C)C)c1] | 348.446 | | | | |
| [11] | 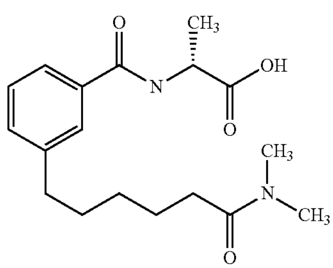 [SMILES: C[C@@H](NC(=O)c1cccc(CCCCCC(=O)N(C)C)c1)C(=O)O] | 334.4189 | | | | |
| [39] | 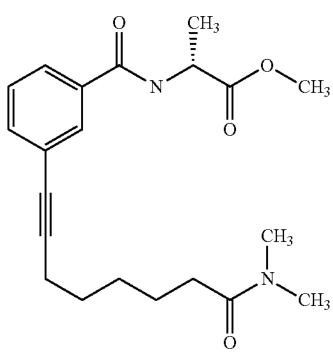 [SMILES: COC(=O)[C@@H](C)NC(=O)c1cccc(C#CCCCCCC(=O)N(C)C)c1] | 372.4683 | | | | |
| [40] | 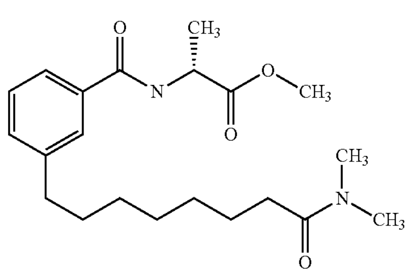 [SMILES: COC(=O)[C@@H](C)NC(=O)c1cccc(CCCCCCCC(=O)N(C)C)c1] | 376.5002 | | | | |

TABLE 2-continued

Emax, and EC50 values for compound selected compounds according to the invention

| Cpd | Structure | Mol Wt | EC50 (nM) | EC50 95% Cls | Emax (%) | Emax 95% Cls |
|---|---|---|---|---|---|---|
| [13] | 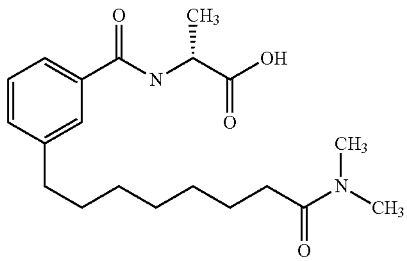 [SMILES: C[C@@H](NC(=O)c1cccc(CCCCCCCC(=O)N(C)C)c1)C(=O)O] | 362.4731 | | | | |
| [41] | 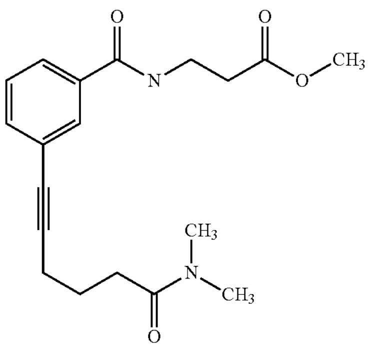 [SMILES: COC(=O)CCNC(=O)c1cccc(C#CCCCC(=O)N(C)C)c1] | 344.4141 | | | | |
| [42] | 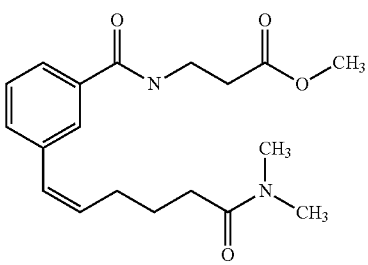 [SMILES: COC(=O)CCNC(=O)c1cccc(/C=C\CCCC(=O)N(C)C)c1] | 346.4301 | | | | |
| [5] | 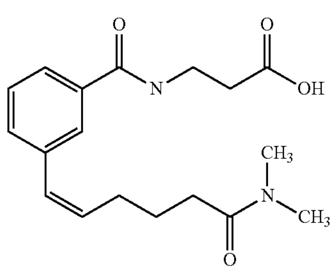 [SMILES: CN(C)C(=O)CCC/C=C\c1cccc(C(=O)NCCC(=O)O)c1] | 332.403 | | | | |
| [43] | 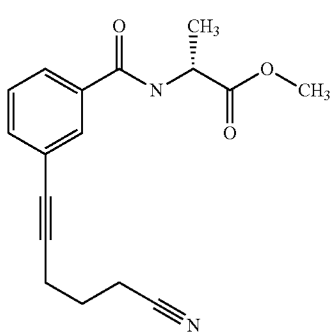 [SMILES: COC(=O)[C@@H](C)NC(=O)c1cccc(C#CCCCC#N)c1] | 298.3446 | | | | |

TABLE 2-continued

Emax, and EC$_{50}$ values for compound selected compounds according to the invention

| Cpd | Structure | Mol Wt | EC50 (nM) | EC50 95% Cls | Emax (%) | Emax 95% Cls |
|---|---|---|---|---|---|---|
| [44] | 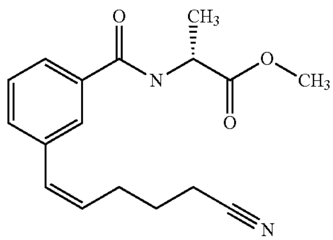 [SMILES: COC(=O)[C@@H](C)NC(=O)c1cccc(/C=C\CCCC#N)c1] | 300.3606 | | | | |
| [6] | 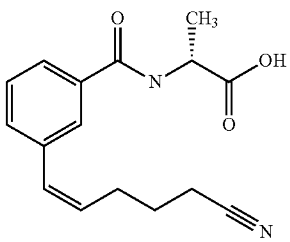 [SMILES: C[C@@H](NC(=O)c1cccc(/C=C\CCCC#N)c1)C(=O)O] | 286.3335 | | | | |
| [45] | 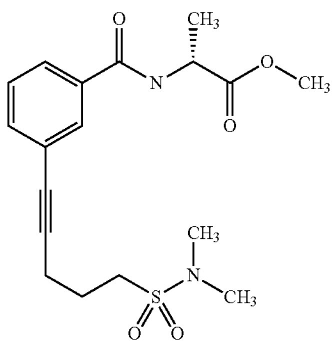 [SMILES: COC(=O)[C@@H](C)NC(=O)c1cccc(C#CCCCS(=O)(=O)N(C)C)c1] | 380.4664 | | | | |
| [46] | 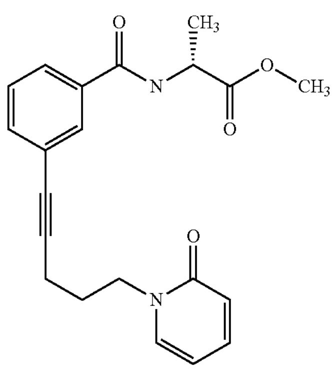 [SMILES: COC(=O)[C@@H](C)NC(=O)c1cccc(C#CCCCn2ccccc2=O)c1] | 366.4205 | | | | |
| [47] | 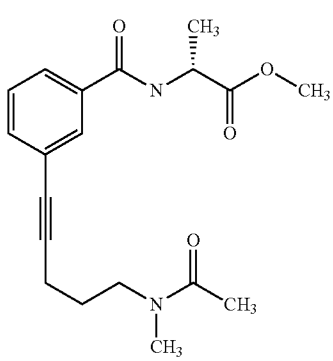 [SMILES: COC(=O)[C@@H](C)NC(=O)c1cccc(C#CCCCN(C)C(C)=O)c1] | 344.4141 | | | | |

TABLE 2-continued

Emax, and EC$_{50}$ values for compound selected compounds according to the invention

| Cpd | Structure | Mol Wt | EC50 (nM) | EC50 95% Cls | Emax (%) | Emax 95% Cls |
|---|---|---|---|---|---|---|
| [48] | 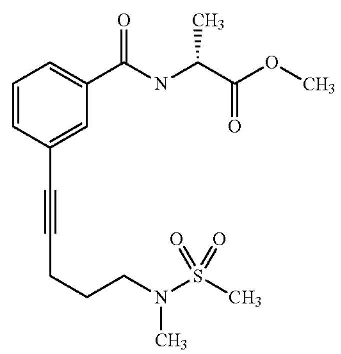 [SMILES: COC(=O)[C@@H](C)NC(=O)c1cccc(C#CCCCN(C)S(C)(=O)=O)c1] | 380.4664 | | | | |
| [49] | 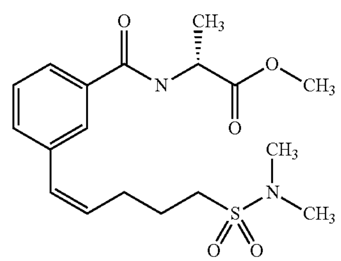 [SMILES: COC(=O)[C@@H](C)NC(=O)c1cccc(/C=C\CCCS(=O)(=O)N(C)C)c1] | 382.4823 | | | | |
| [3] | 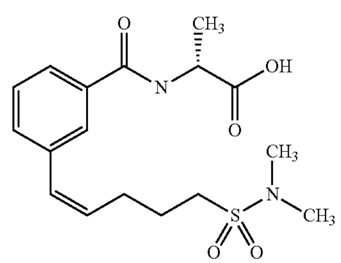 [SMILES: C[C@@H](NC(=O)c1cccc(/C=C\CCCS(=O)(=O)N(C)C)c1)C(=O)O] | 368.4552 | | | | |
| [50] | 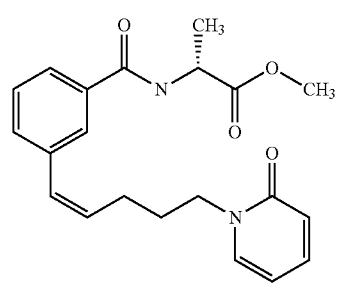 [SMILES: COC(=O)[C@@H](C)NC(=O)c1cccc(/C=C\CCCn2ccccc2=O)c1] | 368.4364 | | | | |
| [51] | 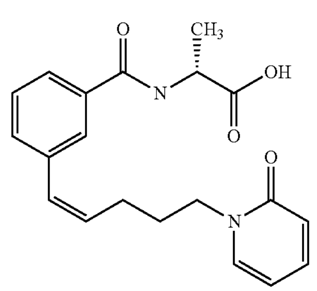 [SMILES: C[C@@H](NC(=O)c1cccc(/C=C\CCCn2ccccc2=O)c1)C(=O)O] | 354.4093 | | | | |

TABLE 2-continued

Emax, and EC₅₀ values for compound selected compounds according to the invention

| Cpd | Structure | Mol Wt | EC50 (nM) | EC50 95% Cls | Emax (%) | Emax 95% Cls |
|---|---|---|---|---|---|---|
| [52] | 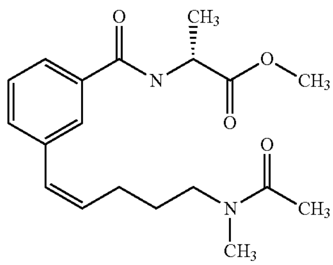 [SMILES: COC(=O)[C@@H](C)NC(=O)c1cccc(/C=C\CCCN(C)C(C)=O)c1] | 346.4301 | | | | |
| [53] | 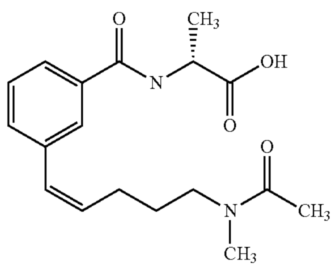 | 332.403 | | | | |
| [54] | 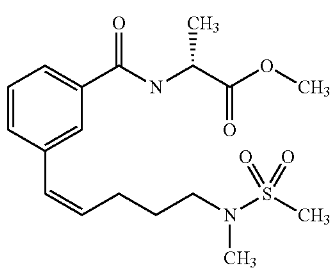 | 382.4823 | | | | |
| [55] | 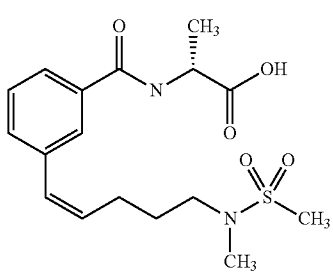 | 368.4552 | | | | |

The invention claimed is:

1. A compound of formula I, or a pharmaceutically acceptable salt thereof,

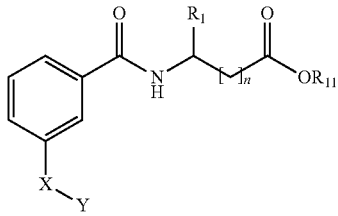

I wherein:
n is 0 or 1;
R$^1$ is selected from H, alkyl and aralkyl, wherein said alkyl and aralkyl groups may be optionally substituted by one or more OH groups;
X is a group selected from
—C≡C—(CH2)p-;
—C(R$^5$)═C(R$^6$)—(CH$_2$)$_q$—; and
—C(R$^5$)(R$^6$)C(R$^7$)(R$^8$)—(CH$_2$)$_r$—;
where each of R$^5$, R$^6$, R$^7$ and R$^8$ is independently H or unsubstituted alkyl, and each of p, q, and r is independently 1, 2, 3, 4 or 5;
Y is a group selected from:
CN;
COOR$^2$;
CONR$^3$R$^4$;
SO$_2$NR$^9$R$^{10}$;
NR$^{12}$COR$^{13}$;
NR$^{14}$SO$_2$R$^{15}$; and
a heterocyclic group selected from oxadiazolyl, thiazolyl, iso-thiazolyl, oxazolyl, iso-oxazolyl, pyrazolyl and imidazolyl;
where each of R$^2$, R$^3$ and R$^4$ is independently H or unsubstituted alkyl;
or R$^3$ and R$^4$ are linked, together with the nitrogen to which they are attached, to form an unsubstituted 5 or 6-membered heterocycloalkyl or an unsubstituted heterocycloalkenyl group, said heterocycloalkyl or heterocycloalkenyl group optionally containing one or more further groups selected from O, N, CO and S, and where each of R$^9$, R$^{10}$, R$^{11}$, R$^{12}$, R$^{13}$, R$^{14}$ and R$^{15}$ is independently H or unsubstituted alkyl.

2. A compound according to claim 1 wherein R1 is selected from H, Me, Et, $^n$Pr, $^i$Pr, CH$_2$-phenyl, CH$_2$-[4-(OH)-phenyl], CH$_2$OH, CH(OH)CH$_3$, CH(CH$_3$)CH$_2$CH$_3$ and CH$_2$CH(CH$_3$)$_2$.

3. A compound according to claim 1 wherein Y is selected from CN, CON(Me)$_2$, CONHMe, CONHEt, SO$_2$N(Me)$_2$, N(Me)COMe, N(Me)SO$_2$Me, CO-piperidinyl, CO-pyrrolidinyl, oxadiazolyl and thiazolyl, more preferably, CON(Me)$_2$.

4. A compound according to claim 1 wherein X— is cis —C(R$^5$)═C(R$^6$)—(CH$_2$)$_q$— and q is 2, 3 or 4.

5. A compound according to claim 4 wherein X is —CH═CH—(CH$_2$)$_q$— and q is 2 or 3.

6. A compound according to claim 1 wherein X is —C(R$^5$)(R$^6$)C(R$^7$)(R$^8$)—(CH$_2$)$_r$— and r is 2, 3 or 4.

7. A compound according to claim 6 wherein X is —CH2-CH2-(CH2)r- and r is 2 or 3.

8. A compound according to claim 1 which is of formula Ia, or a pharmaceutically acceptable salt thereof,

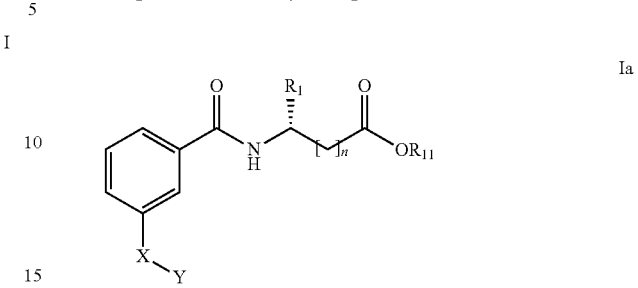

Ia wherein R1, R11, X, Y and n are as defined in claim 1.

9. A compound according to claim 1 which is of formula Ib, or a pharmaceutically acceptable salt thereof,

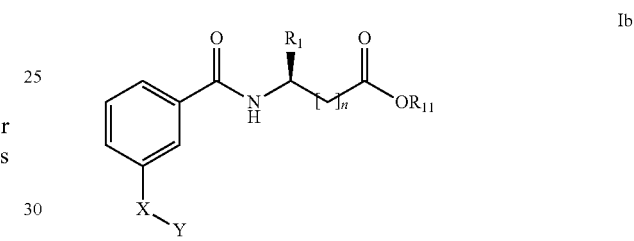

Ib wherein R$^1$, R$^{11}$, X, Y and n are as defined in claim 1.

10. A compound according any claim 1 wherein n is 0.

11. A compound according any claim 1 wherein R1 is Me.

12. A compound according to claim 8 wherein n is 0, R1 is Me and X is —CH═CH—(CH2)3- or —CH2-CH2-(CH2)3-.

13. A compound according to claim 1 wherein n is 1 and R1 is H.

14. A compound which is selected from the following:

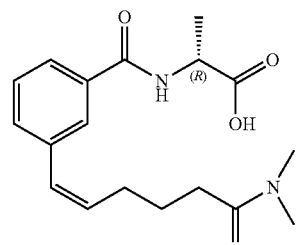

[1]

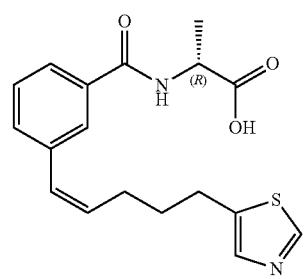

[2]

99
-continued
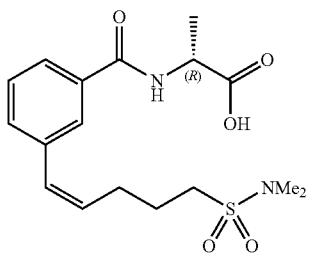
[3]
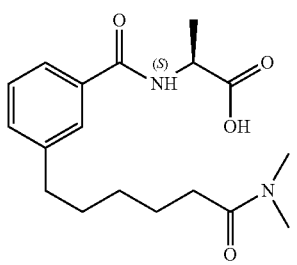
[4]
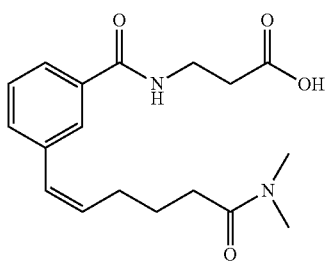
[5]
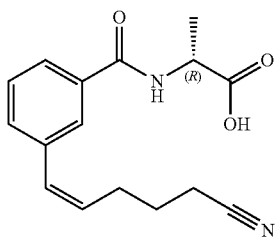
[6]
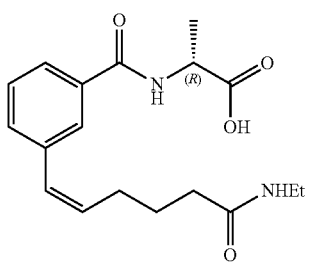
[7]
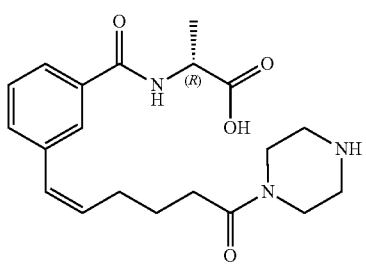
[8]
100
-continued
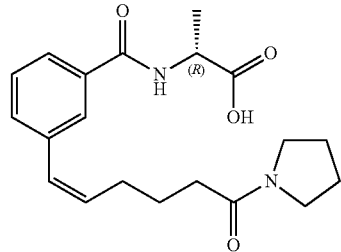
[9]
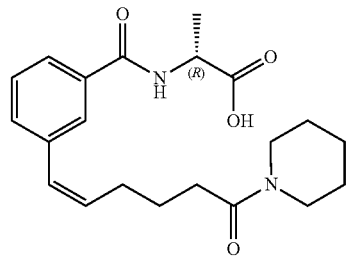
[10]
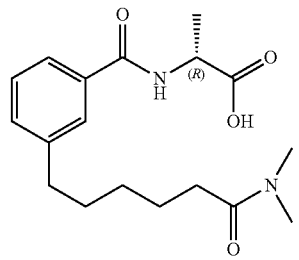
[11]
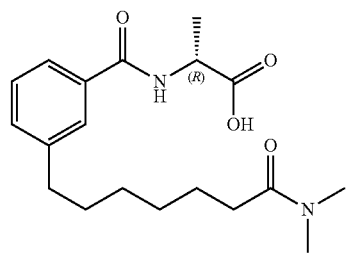
[12]
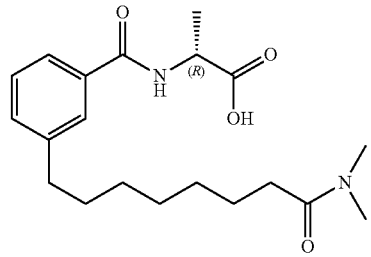
[13]
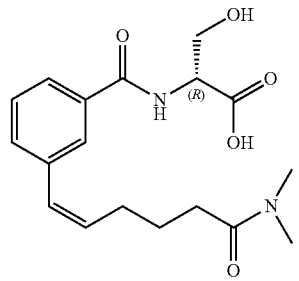
[14]

| 101 | 102 |
|---|---|
| -continued | -continued |
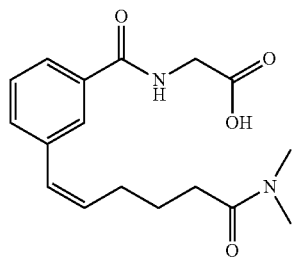
[15]
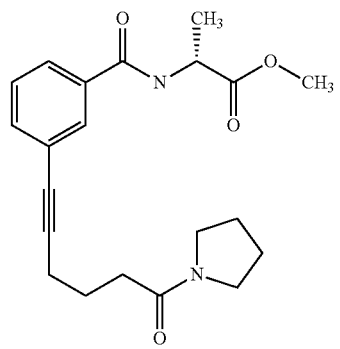
[20]
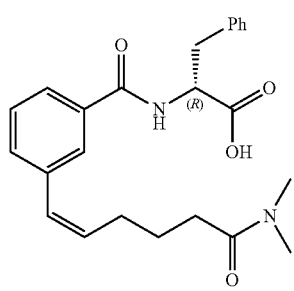
[16]
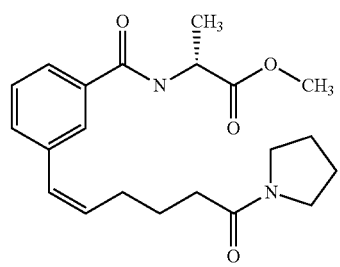
[21]
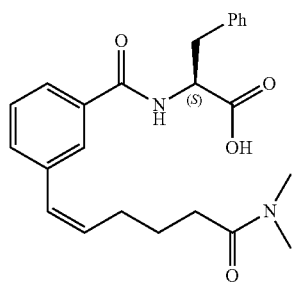
[17]
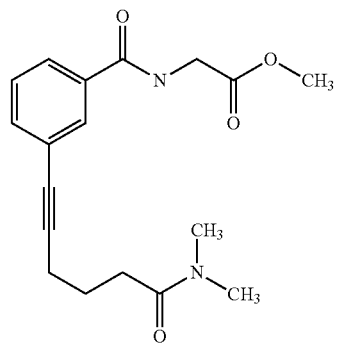
[22]
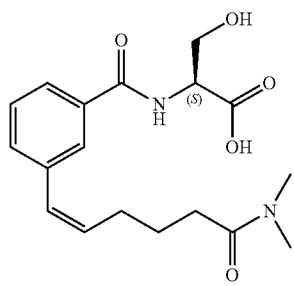
[18]
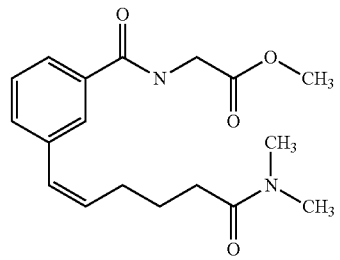
[23]
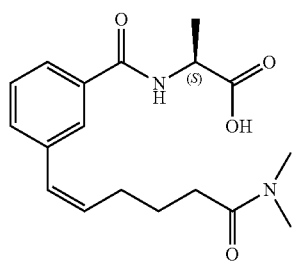
[19]
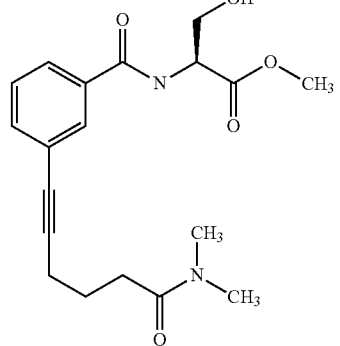
[24]

103
-continued
[25]
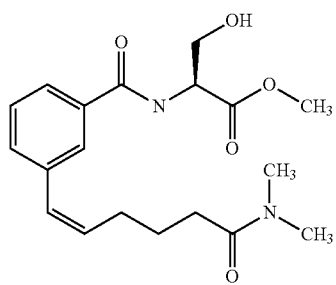
[26]
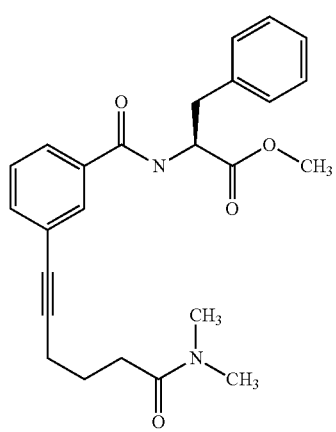
[27]
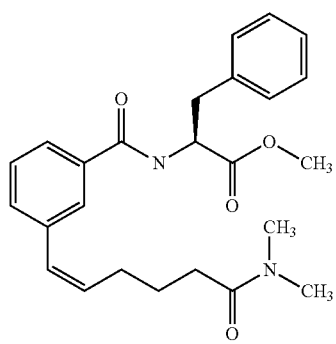
[28]
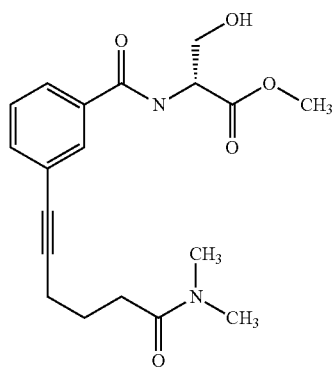
104
-continued
[29]
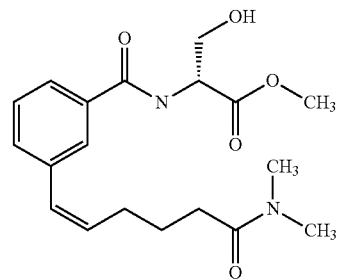
[30]
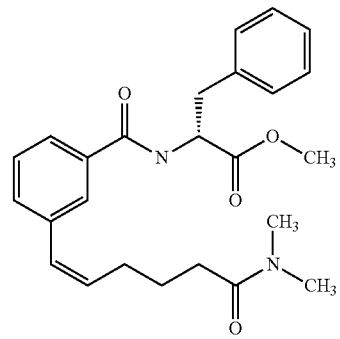
[31]
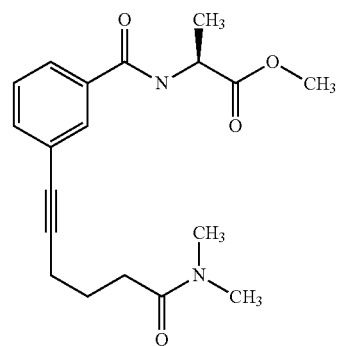
[32]

[33]
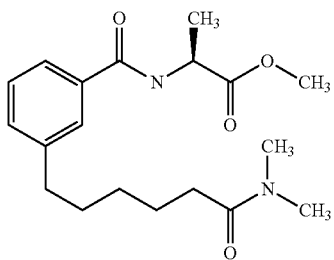
[34]
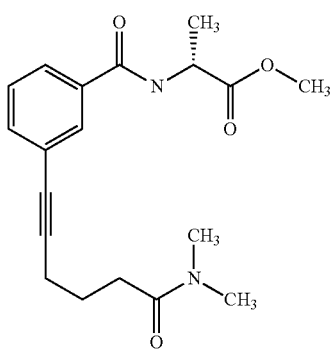
[35]
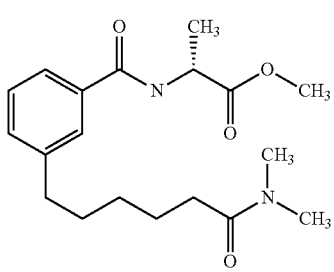
[36]
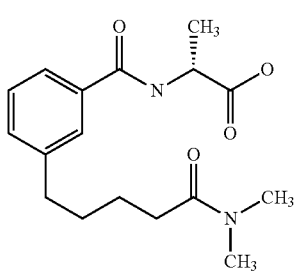
[37]
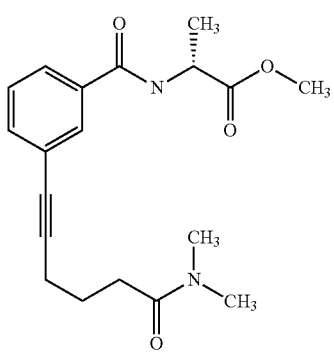
[38]
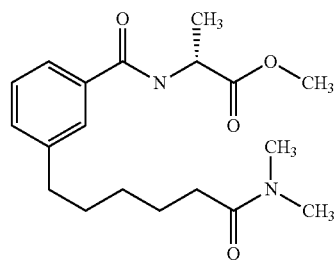
[39]
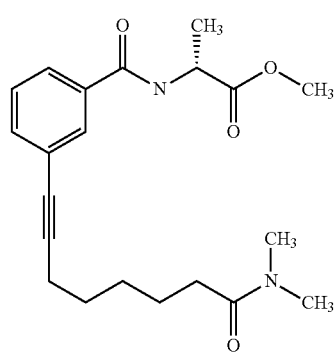
[40]
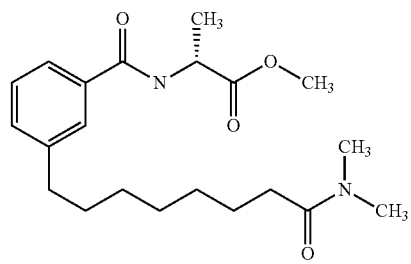
[41]
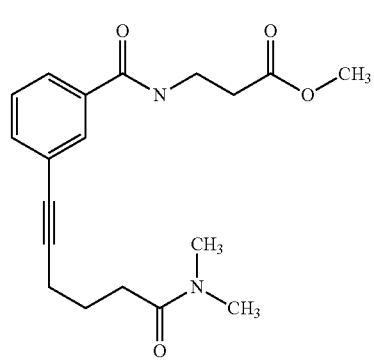
[42]
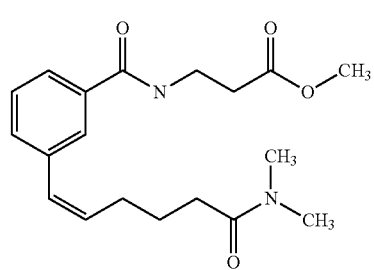

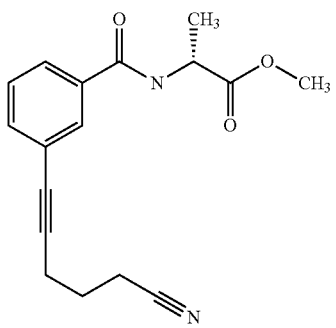
[43]
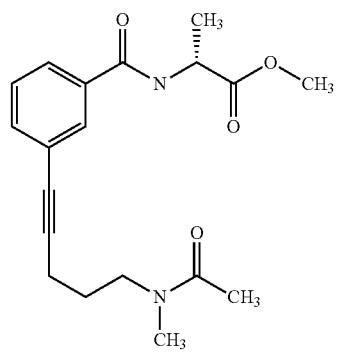
[47]
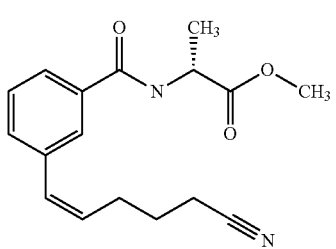
[44]
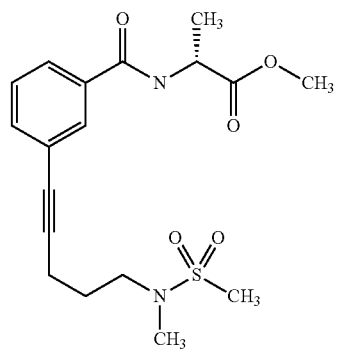
[48]
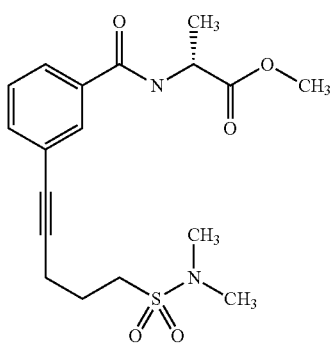
[45]
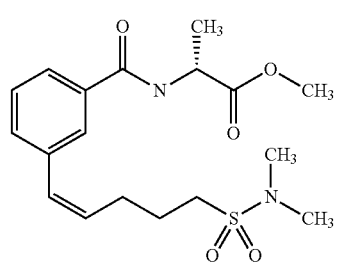
[49]
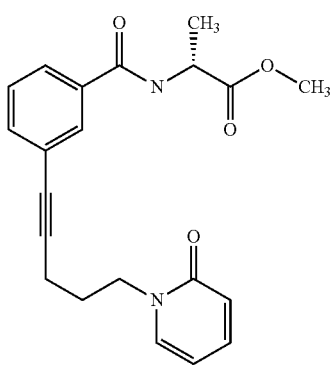
[46]
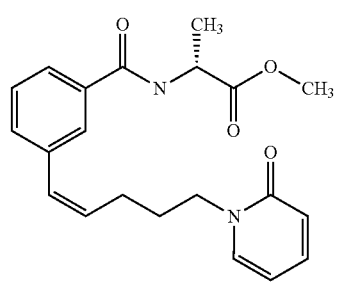
[50]
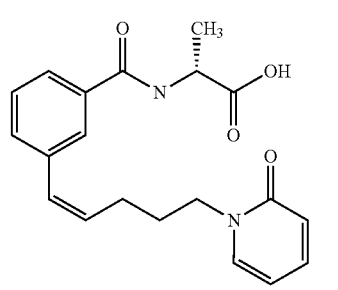
[51]

-continued

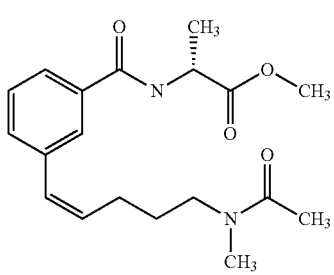

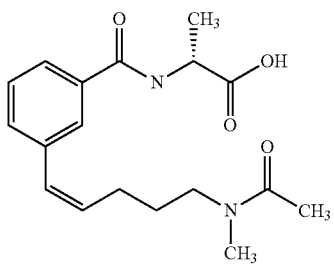 [SMILES: CC(=O)N(C)CCC/C=C\c1cccc(C(=O)N[C@H](C)C(=O)O)c1]

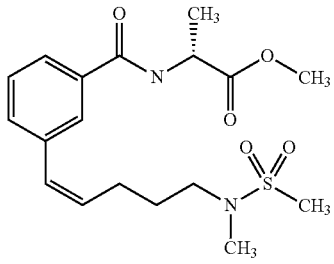 [SMILES: COC(=O)[C@@H](C)NC(=O)c1cccc(/C=C\CCCN(C)S(C)(=O)=O)c1]

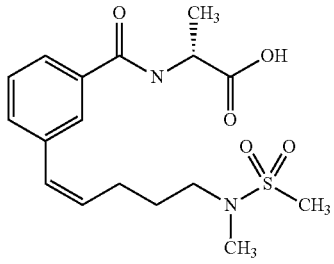 [SMILES: C[C@@H](NC(=O)c1cccc(/C=C\CCCN(C)S(C)(=O)=O)c1)C(=O)O]

and pharmaceutically acceptable salts, and enantiomers thereof.

15. A compound according to claim 1 which is of the formula [1], or a pharmaceutically acceptable salt thereof:

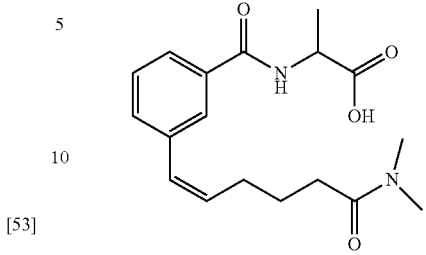

[1]

16. A compound according to claim 1 which is of the formula [1a] or formula [1b], or a pharmaceutically acceptable salt thereof:

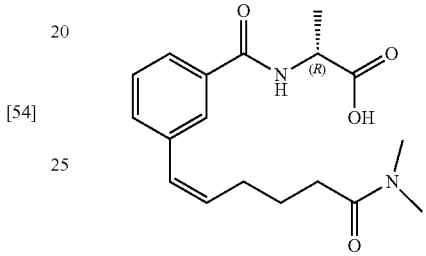

[1a]

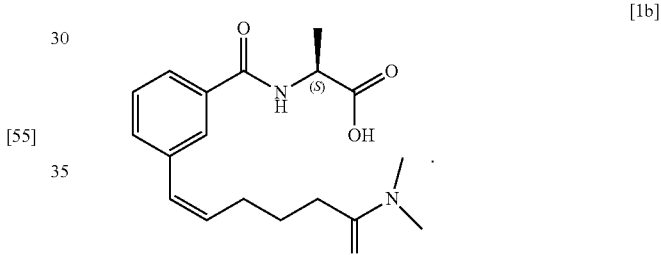

[1b]

17. A pharmaceutical composition comprising a compound according to claim 1 admixed with a pharmaceutically acceptable diluent, excipient or carrier.

18. A process for preparing a compound of formula I as defined in claim 1 which is of formula (VIII), wherein $R^1$ and n are as defined in claim 1, said process comprising the steps of:

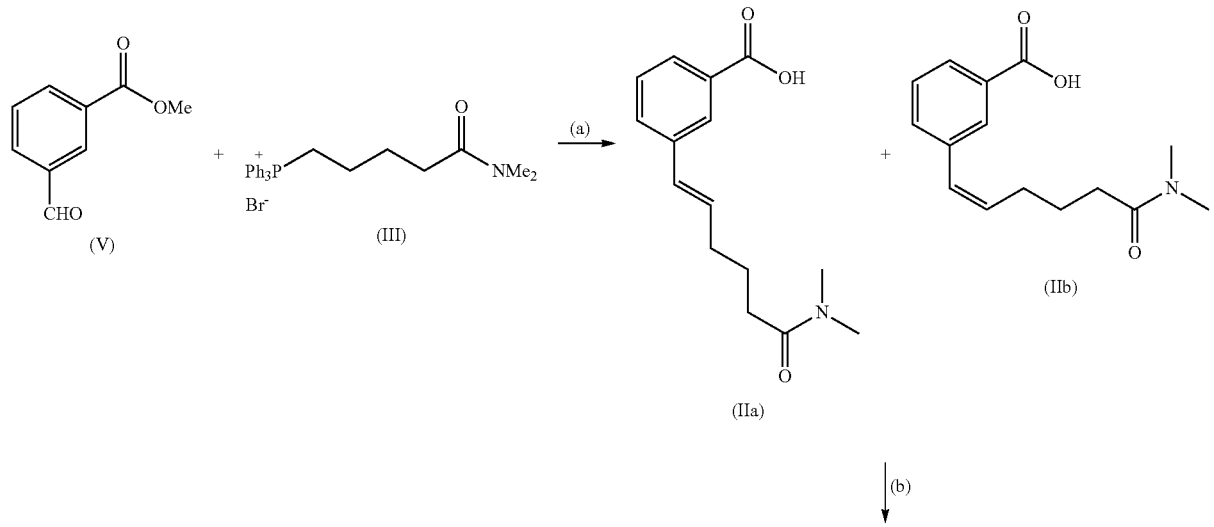

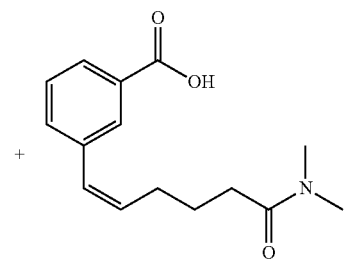

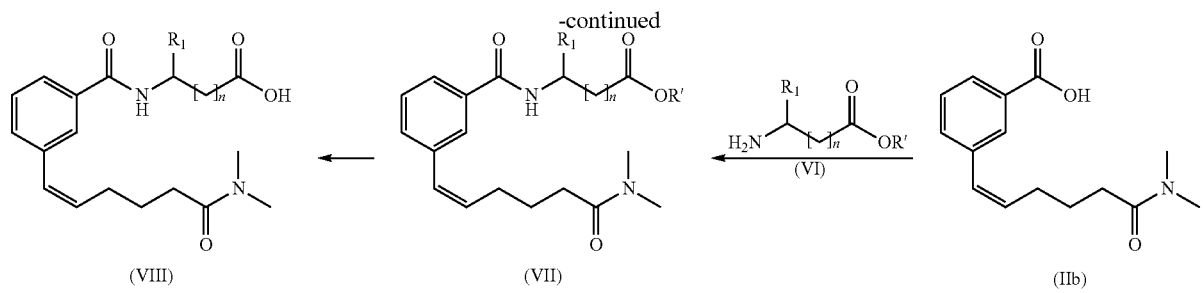

-continued

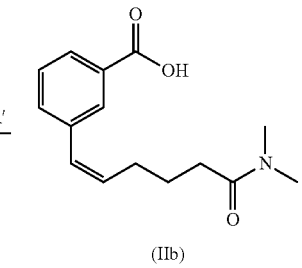

(i) coupling a compound of formula (V) with a compound of formula (III) to form a mixture comprising compounds of formulae (IIa) and (IIb);
(ii) separating said compound of formula (IIb) from the mixture obtained in step (i);
(iii) treating the compound of formula (IIb) obtained in step (ii) with a compound of formula (VI), where $R^1$ and n are as defined in claim 1, and R' is alkyl, to form a compound of formula (VII); and
(iv) converting said compound of formula (VII) to a compound of formula (VIII).

19. A process for preparing a compound of formula I as defined in claim 1 which is of formula (VIII), wherein $R^1$ and n are as defined in claim 1, said process comprising the steps of:

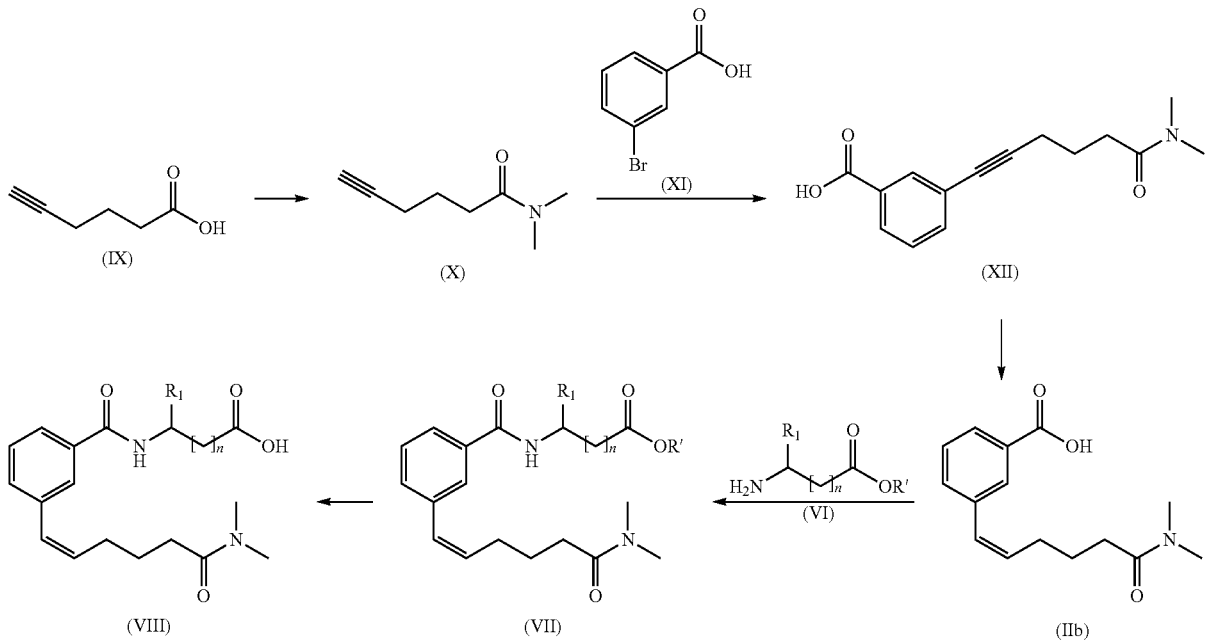

(i) treating a compound of formula (IX) with dimethylamine to form a compound of formula (X);
(ii) reacting said compound of formula (X) with a compound of formula (XI) to form a compound of formula (XII);
(iii) hydrogenating said compound of formula (XII) to form a compound of formula (IIb);
(iv) treating said compound of formula (IIb) with a compound of formula (VI), where $R^1$ and n are as defined in claim 1, and R' is alkyl, to form a compound of formula (VII); and
(v) converting said compound of formula (VII) to a compound of formula (VIII).

* * * * *